United States Patent
Beardsley et al.

(10) Patent No.: US 11,246,950 B2
(45) Date of Patent: Feb. 15, 2022

(54) COMBINATION CANCER IMMUNOTHERAPY WITH PENTAAZA MACROCYCLIC RING COMPLEX

(71) Applicant: Galera Labs, LLC, Creve Coeur, MO (US)

(72) Inventors: Robert A. Beardsley, University City, MO (US); Jeffery L. Keene, St. Louis, MO (US); Dennis P. Riley, Chesterfield, MO (US)

(73) Assignee: GALERA LABS, LLC, Creve Coeur, MO (US)

( * ) Notice: Subject to any disclaimer, the term of this patent is extended or adjusted under 35 U.S.C. 154(b) by 278 days.

(21) Appl. No.: 16/604,872

(22) PCT Filed: Apr. 13, 2018

(86) PCT No.: PCT/US2018/027588
§ 371 (c)(1),
(2) Date: Oct. 11, 2019

(87) PCT Pub. No.: WO2018/191676
PCT Pub. Date: Oct. 18, 2018

(65) Prior Publication Data
US 2020/0376148 A1    Dec. 3, 2020

Related U.S. Application Data

(60) Provisional application No. 62/485,061, filed on Apr. 13, 2017, provisional application No. 62/572,377, filed on Oct. 13, 2017.

(51) Int. Cl.
| | | |
|---|---|---|
| *A61K 51/04* | (2006.01) | |
| *A61P 35/00* | (2006.01) | |
| *A61K 35/17* | (2015.01) | |
| *A61K 39/00* | (2006.01) | |
| *A61K 39/395* | (2006.01) | |

(52) U.S. Cl.
CPC .......... *A61K 51/0482* (2013.01); *A61K 35/17* (2013.01); *A61K 39/0011* (2013.01); *A61K 39/3955* (2013.01); *A61P 35/00* (2018.01)

(58) Field of Classification Search
CPC ................ A61K 51/0482; A61K 35/17; A61K 39/0011; A61K 39/3955; A61P 35/00
See application file for complete search history.

(56) References Cited

U.S. PATENT DOCUMENTS

| | | |
|---|---|---|
| 3,930,867 A | 1/1976 | Bigelow |
| 4,001,212 A | 1/1977 | Richman |
| 4,702,998 A | 10/1987 | Tanaka et al. |
| 5,096,724 A | 3/1992 | Zenner et al. |
| 5,610,293 A | 3/1997 | Riley et al. |
| 5,637,578 A | 6/1997 | Riley et al. |
| 5,874,421 A | 2/1999 | Riley et al. |
| 5,976,498 A | 11/1999 | Newumann et al. |
| 6,040,330 A | 3/2000 | Hausheer et al. |
| 6,084,093 A | 7/2000 | Riley et al. |
| 6,177,419 B1 | 1/2001 | Campbell et al. |
| 6,180,620 B1 | 1/2001 | Salvemini |
| 6,204,259 B1 | 3/2001 | Riley et al. |
| 6,214,817 B1 | 4/2001 | Riley et al. |
| 6,245,758 B1 | 6/2001 | Stern et al. |
| 6,395,725 B1 | 5/2002 | Salvemini |
| 6,525,041 B1 | 2/2003 | Neumann et al. |

(Continued)

FOREIGN PATENT DOCUMENTS

| | | |
|---|---|---|
| CN | 103906756 | 7/2014 |
| EP | 0524161 | 1/1993 |

(Continued)

OTHER PUBLICATIONS

Fretland et al., Superoxide Dismutase (SOD) Modulates Acetic Acid-Induced Colitis in Rodents, Gastroenterology, 1991, 100: A581 1991.

Gryglewski et al., Superoxide Anion is involved in the breakdown of Endothelium-Derived Vascular Relaxing Factor, Nature, 1986, 320: 454-456 1986.

(Continued)

*Primary Examiner* — Robert S Cabral
(74) *Attorney, Agent, or Firm* — Bryan Cave Leighton Paisner LLP

(57) ABSTRACT

A method of treating a cancer in a mammalian subject afflicted with the cancer, includes administering to the subject an immune checkpoint inhibitor, and administering to the subject a pentaaza macrocyclic ring complex corresponding to the formula (I) below, prior to, concomitantly with, or after administration of the immune checkpoint inhibitor, to increase the response of the cancer to the immune checkpoint inhibitor.

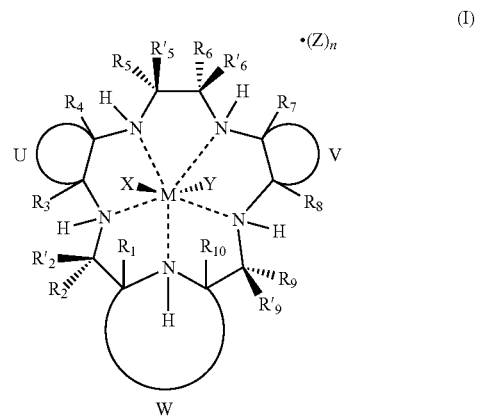

14 Claims, 16 Drawing Sheets

(56) References Cited

U.S. PATENT DOCUMENTS

| | | |
|---|---|---|
| 6,916,799 B2 | 7/2005 | Fridovich et al. |
| 7,407,645 B2 | 8/2008 | Neumann et al. |
| 7,445,641 B1 | 11/2008 | Ornberg et al. |
| 7,981,421 B2 | 7/2011 | Zhou et al. |
| 8,263,568 B2 | 9/2012 | Slomczynska et al. |
| 8,444,856 B2 | 5/2013 | Slomczynska et al. |
| 8,808,545 B2 | 8/2014 | Slomczynska et al. |
| 9,149,483 B2 | 10/2015 | Keene et al. |
| 9,855,279 B2 | 1/2018 | Rothstein et al. |
| 10,597,415 B2 | 3/2020 | Keene et al. |
| 2002/0072512 A1 | 6/2002 | Salvemini |
| 2002/0128248 A1 | 9/2002 | Salvemini |
| 2003/0050297 A1 | 3/2003 | Crapo |
| 2004/0132706 A1 | 7/2004 | Salvemini |
| 2004/0219138 A1 | 11/2004 | Salvemini |
| 2005/0101581 A1 | 5/2005 | Reading et al. |
| 2005/0171198 A1 | 8/2005 | Salvemini |
| 2005/0175580 A1 | 8/2005 | Salvemini |
| 2005/0222250 A1 | 10/2005 | Rezvani |
| 2006/0089710 A1 | 4/2006 | Ornberg et al. |
| 2006/0140953 A1 | 6/2006 | Newell et al. |
| 2006/0199792 A1 | 9/2006 | Groves et al. |
| 2006/0223808 A1 | 10/2006 | Chackalamannil et al. |
| 2008/0269185 A1 | 10/2008 | Rothstein et al. |
| 2008/0318917 A1 | 12/2008 | Salvemini et al. |
| 2009/0131377 A1 | 5/2009 | Salvemini |
| 2009/0221622 A1 | 9/2009 | Teja et al. |
| 2009/0257979 A1 | 10/2009 | Beigelman et al. |
| 2010/0304415 A1 | 12/2010 | Slomczynska et al. |
| 2011/0136756 A1 | 6/2011 | Keene et al. |
| 2013/0079317 A1 | 3/2013 | Keene et al. |
| 2014/0142065 A1 | 5/2014 | Che et al. |
| 2017/0044193 A1 | 2/2017 | Keene et al. |
| 2018/0237462 A1 | 8/2018 | Keene et al. |
| 2019/0151331 A1 | 5/2019 | Beardsley et al. |
| 2019/0209524 A1 | 7/2019 | Beardsley et al. |

FOREIGN PATENT DOCUMENTS

| | | |
|---|---|---|
| EP | 0598753 | 3/1998 |
| EP | 2760874 | 8/2014 |
| EP | 3388082 | 10/2018 |
| JP | H06509566 | 10/1994 |
| JP | 2002506445 | 2/2002 |
| JP | 2002534382 | 10/2002 |
| JP | 2003509423 | 3/2003 |
| JP | 2004517113 | 6/2004 |
| JP | 2011513333 | 4/2011 |
| JP | 2011516610 | 5/2011 |
| JP | 2014526562 | 10/2014 |
| RU | 2313368 | 9/2011 |
| WO | 1991010645 | 7/1991 |
| WO | 1993002090 | 2/1993 |
| WO | 1994015925 | 7/1994 |
| WO | 95028968 | 11/1995 |
| WO | 1996039396 | 12/1996 |
| WO | 97006830 | 2/1997 |
| WO | 98058636 | 12/1998 |
| WO | 00072893 | 12/2000 |
| WO | 01019823 | 3/2001 |
| WO | 200158458 | 8/2001 |
| WO | 2002053142 | 7/2002 |
| WO | 2002058686 | 8/2002 |
| WO | 2002071054 | 9/2002 |
| WO | 2002100395 | 12/2002 |
| WO | 2003024434 | 3/2003 |
| WO | 2005042718 | 5/2005 |
| WO | 2006078713 | 7/2006 |
| WO | 2006083508 | 8/2006 |
| WO | 2007139897 | 12/2007 |
| WO | 2008027547 | 3/2008 |
| WO | 2008045559 | 4/2008 |
| WO | 2009111294 | 9/2009 |
| WO | 2009134616 | 11/2009 |
| WO | 2009143454 | 11/2009 |
| WO | 2011113019 | 9/2011 |
| WO | 2013048965 | 4/2013 |
| WO | 2017027728 | 2/2017 |
| WO | 2017192740 | 11/2017 |
| WO | 2018191676 | 10/2018 |

OTHER PUBLICATIONS

Bannister et al., Aspects of the structure, function, and applications of Superoxide Dismutase, CRC Critical Reviews in Biochemistry, 1987, 22(2): 111-180 1987.

Newton et al., Synthesis and characterization of the Mn(II) complex of [15]aneN.sub.5, J. Coord. Chem., 1988, 19: 265-277 1988.

Bradshaw et al., A simple crab-like cyclization procedure to prepare polyaza-crowns and cyclams with one or two unsubstitute macroring Nitrogen atoms or with a Hydroxy group, J. Heterocyclic Chem, 1989, 26: 1431-1435 1989.

Krakowiak et al., Preparation of Triaza-, Tetraaza- and Peraza-Crown Compounds containing Aminoalkyl Side Groups or Unsubstituted Rin Nitrogen Atoms, J. Org. Chem, 1990, 55(10): 3364-3368 1990.

Riley et al., Stopped-flow Kinetic Analysis for Monitoring superoxide decay in aqueous systems, Analystical Biochemistry, 1991, 196: 344-349 1991.

Weiss et al., Catalytic efficacies of agents that dismutate superoxide, J. Cell. Biochem., 1991, Supplement 15C: 216 1991.

Eldor et al., Perturbation of endothelial functions by ionizing irradiation: effects on prostaglandins, chemoattractants and mitogens, Semin Thromb Hemost, 1989, 15(2): 215-225 1989.

Escribano et al., Aerosol Orgotein (Ontosein) for the Prevention of Radiotherapy-Induced Adverse Effects in Head and Neck Cancer Patients: A feasibility study, Neoplasma, 2002, 49(3): 201-209 2002.

Gridley et al., Chapter 16, Therapeutic Application of Superoxide Dismutase (SOD) (Salvemini and Cuzzocrea, eds.), 2004, 1-20 2004.

Guo et al., Prevention of Radiation-Induced Oral Cavity Mucositis by Plasmid/Liposome Delivery of the Human Manganese Superoxide Dismutase (SOD2) Transgene, Radiat. Red., 2003, 159(3): 361-370 2003.

Knox, et al., Chemotherapy-induced oral mucositis. Prevention and Management, Drugs Aging, 2000, 17(4): 257-267 2000.

Leussink et al., Pathways of Proximal Tubular Cell Death in Bismuth Nephrotoxicity, Toxicol. Appl. Pharmacol., 2002, 180(2): 100-109 2002.

Orrell, R.W., AEOL-10150 (Aeolus), Current Opinion Investig. Drugs, 2006, 7(1): 70-80 2006.

Peterson, D. E. Research advances in oral mucositis. Current Opinion Oncol., 1999, 11(4): 261-266 1999.

Plevova, P. Prevention and treatment of chemotherapy- and radiotherapy-induced oral mucositis: a review. Oral Oncol. 1999; 35(5): 453-470 1999.

Salvemini et al., Amelioration of Joint Disease in a Rat Model of Collagen-Induced Arthritis by M40403, a Superoxide Dismutase Mimetic, Arthritis & Rheumatism, 2001, 44: 2909-2921 2001.

Slikkerveer et al., Pharmacokinetics and Toxicity of Bismuth Compounds, Med. Toxicol. Adverse Drug Exp, 1989, 4(5): 303-323 1989.

Sonis, Oral Mucositis in Cancer Therapy, Support. Oncol., 2004, 2 (supple.3): 3-8 2004.

Sonis et al., Mitigating Effects of Interleukin 11 on Consecutive Courses of 5-Fiuorouracil-Induced Ulcerative Mucositis in Hamsters, Cytokine, 1997, 9(8): 605-612 1997.

Ahmad et al., Mitochondrial $O_2$ and $H_2O_2$ Mediate Glucose Deprivation-induced Cytotoxicity and Oxidative Stress in Human Cancer Cells, J. Bio. Chem, 2005, 280(6): 4254-4263 2005.

Sonis et al., Transforming Growth Factor- B3 Mediated Modulation of Cell Cycling and Attenuation of 5-Fiuorouracil Induced Oral Mucositis, Oral Oncol., 1997, 33(1): 47-54 1997.

Sonis et al., Defining Mechanisms of action of interleukin-11 on the progression of radiation-induced oral mucositis in hamsters, Oral Oncology, 2000, 36(4): 373-381 2000.

(56) References Cited

OTHER PUBLICATIONS

Cuzzocrea et al., C. Tempol, a membrane-permeable radical scavenger, reduces dinitrobenzene sulfonic acid-induced colitis, Eur J Pharmacol., 2000, 406:127-137 2001.
Murphy et al., Efficacy of superoxide dismutase mimetic M40403 in attenuating radiation-induced oral mucosisis in hamsters, Clin. Can. Res., 2008, 14(13):4292-4297 2008.
Goodman & Gilman's The Pharmacological Basis of Therapeutics, 10th Edition, McGraw Hill, 1996 1996.
Suenderhauf et al., A Physiologically Based Pharmacokinetic Model of the Minipig: Data Compilation and Model Implementation, Pharm Res., 2013, 30(1): 1-15 2013.
Cuzzocrea et al., Protective effects of M40401, a selective superoxide dismutase mimetic, on zymosan-induced nonseptic shock, Crit. Care Med., 2004, 21(1): 157-167 2004.
Cuzzocrea et al., Reduction in the development of Cerulein-induced acute pancreatitis by treatment with M40401, a new selective superoxide dismutase mimetic, Shock, 2004, 22(3): 254-261 2004.
Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015) 2015.
Cotton et al., Advanced Inorganic Chemistry, Chapter 5, "Coordination Compounds", 2nd revised edn., Interscience Publishers, 1966, 139 1966.
Cotton et al., Advanced Inorganic Chemistry, Chapter 2, "Coordination Compounds", 2nd revised edn., Interscience Publishers, 1966, 35-36, 45-49 1966.
Wang et al., Evidence of d-phenylglycine as delivering tool for improving I-dopa absorption, J. Biomed. Sci., 2010, 17: 71-79 2010.
Wikipedia, Cefalexin, retrieved Nov. 2, 2016, from en.wikipedia.org/wiki/Cefalexin, 6 pages 2016.
Hironaka et al., Quantitative Evaluation of PEPT1 Contribution to Oral Absorption of Cephalexin in Rats, Pharm. Res., 2009, 26(1): 40-50 2009.
Knütter et al., Transport of Angiotensin-Converting Enzyme Inhibitors by H+/Peptide Transporters Revisited, J. Pharma. Exp. Thera., 2008, 327(2): 432-441 2008.
Patent Cooperation Treaty, International Search Report for PCT/US2016/046599, dated Nov. 17, 2016, 5 pages Nov. 17, 2016.
Park et al., Facility case volume and outcomes for intensity-modulated radiotherapy in head and neck cancer, Department of Therapeutic Radiology, Yale School of Medicine, 1 pg. Sep. 26, 2016.
Boero et al., Importance of Radiation Oncologist Experience Among Patients With Head-and-Neck Cancer Treated With Intensity-Modulated Radiation Therapy, Journal of Clinical Oncology, 2016, 34(7): 684-696 Mar. 1, 2015.
Ferreira et al., Effect of radiotherapy delay in overall treatment time on local control and survival in head and neck cancer: Review of the literature, Reports of Practical Oncology and Radiotherapy, 2015, 20: 328-339 May 24, 2015.
Anderson et al., Phase 1b Trial of Superoxide Dismutase Mimetic GC4419 to Reduce Chemoradiotherapy-induced Oral Mucositis in Patients with Oral Cavity or Oropharyngeal Carcinoma, Multidisciplinary Head and Neck Cancer Symposium, Scottsdale, Arizona, 17 pgs Feb. 18, 2016.
Hussan et al., A review on recent advances of enteric coating, Journal of Pharmacy, 2012, 2(6): 5-11 2012.
Strickley, R. G., Solubilizing Excipience in Oral and Injectable Formulations, Pharmaceutical Research, 2004, 21 (2): 201-230 2004.
Keene, J. L., Declaration under 37 C.F.R. 1.132 May 14, 2014.
Salvemini et al., Pharmacological manipulation of the in ammatory cascade by the superoxide dismutase mimetic, M40403, British Journal of Pharmacology, 2001, 132: 815-827 2001.

Masini et al., Reduction of antigen-induced respiratory abnormalities and airway inflammation in sensitized guinea pigs by a superoxide dismutase mimetic, Free Radical Biology & Medicine, 2005, 39: 520-531 2005.
Salvemini et al., Superoxide Dismutase Mimetics, Pulmonary Pharmocology & Therapeutics, 2002, 15: 439-447 2002.
Weiss et al., Manganese-based Superoxide Dismutase Mimetics Inhibit Neutrophil Infiltration in Vivo, Journal of Biological Chemistry, 1996, 271(42): 26149-26156 1996.
Udipi et al., Modification of inflammatory response to implated biomedical materials in vivo by surface bound superoxide dismutase mimics, Journal of Biomedical Materials Research, 1999, 1-12 1999.
Cuzzocrea et al., Protective effects of M40403, a superoxide dismutase mimetic, in a rodent model of colitis, European Journal of Pharmacology, 2001, 432: 79-89 2001.
Salvemini et al., Protective effects of superoxied dismutase mimetic nd peroxynitrite decomposition catalyst in endotoxin-indueced intestinal damage, 1999, British Journal of Pharmacology, 127(3):685-692 1999.
Jin et al., Clinical Observation on Superoxide Dismutase in Respect of Resistance to Skin Damage Resulting from Radiation, Chinese Journal of Radiological Health, 1993, 2(3): 137 1993.
Zhou et al., Experimental Study on Superoxide Dismutase for Prophylaxis and Treatment of Inflammatory Damage to Mouth Mucosa in Animals, West China Journal of Stomatology, 1996, 14(2) 1996.
Kasten et al., Potentiation of Nitric Oxide-Mediated Vascular Relaxation by SC52608, a Superoxide Dismustas Mimic, 1995.
Patent Cooperation Treaty, International Search Report for PCT/US2018/018407, 6 pages Sep. 17, 2018.
Tabata et al., Ion-Pair Extraction of Metalloporphyrins into Acetonitrile for Determination of Copper(II), Anal. Chem., 68: 758-762 1996.
Mazzucotelli, et al., Determination of trace amounts of Metalloprotein Species in Marine Mussel Samples by High Performance Liquid Chromatography with Inductively Coupled Plasma Atomic Emission Spectrometric Detection, Analyst., 116:605-608 1991.
Furuya et al., Determination of Pheophytinatoiron(III) Chlorides by Reverse Phase High Performance Liquid Chromatography, Analytical Sciences, 3: 353-357 1987.
Zhang et al., Quantitative determination of SC-68328 in dog plasma using flow injection and tandem mass spectroscopy, Journal of Mass Spectrometry, 35(3): 354-360 2000.
Sakai et al., Liquid-Chromatographic Separation and Determination of Coproporphyrins I & III in Urine, Clinical Chemistry, 29(2): 350-353 1983.
Riley, Functional Mimics of Supeoxide Dismutase Enzymes and Therapeutic Agents, Chem. Rev., 2572-2587 1999.
Berge et al., Pharmaceutical Salts, J. Pharm. Sci., 66: 1-19 1977.
European Patent Office, European Search Report issued for EP 10179542, 4 pages Aug. 5, 2011.
European Patent Office, Extended European Search Report for 16835928.9, publication 3334744, 10 pgs. Feb. 4, 2019.
Cornwell et al., Glyceryl monocaprylate/caprate as a moderate skin penetration enhancer, International Journal of Pharmaceutics, 171:243-255 1998.
Eurasian Patent Office, Search Report for 201892510, 1 page May 28, 2019.
European Patent Office, Extended Search Report for EP App. 18215666.1, 12 pages Jul. 19, 2019.
Di Paolo et al., Reduced development of experimental periodontitis by treatment with M40403, a superoxide dismutase mimetic, European Journal of Pharmacology, 51: 151-157 2005.
McFadden et al., M40403, a superoxide dismutase mimetic, protects cochlear hair cells from gentamicin, but not cisplatin toxicity, Toxicology and Applied Pharmacology, 186: 46-54 2003.
European Patent Office, Extended Search Report for EP App. 17793268.8, 8 pages Nov. 29, 2019.
Fath et al., Enhancement of Carboplatin-Mediated Lung Cancer Cell Killing by Simultaneous Disruption of Glutathione and Thioredoxin Metabolism, Clinical Cancer Research, 17(19): 6206-6217 2011.
Jungwirth et al., Anticancer Activity of Metal Complexes: Involvement, Antioxidants & Redox Signaling, 15(4): 1085-1127 2011.

(56) References Cited

OTHER PUBLICATIONS

Cao et al., Mechanisms of ferroptosis, Cell. Mol. Life Sci., 2016, 11:2195-2209 2016.
Rodman III, et al., Enhancement of Radiation Response in Breast Cancer Stem Cells by Inhibition of Thioredoxin and Glutathione Dependent Metabolism, Radiat Res., 2016, 186(4): 385-395 2016.
Raj et al., Selective killing of cancer cells by a small molecule targeting the stress response to ROS, Nature, 475: 231-234 2016.
Samlowski et al., Evaluation of a Superoxide Dismutase Mimetic as an Adjunct to Interleukin 2 Based Cancer Therapy, Madame Curie Report, 230-249 2006.
Samlowski et al., A nonpeptidyl mimic of superoxide dismutase, M40403, inhibits dose-limiting hypotension associated with interleukin-2 and increases its antitumor effects, Nature Medicine, 9:750-755 2003.
Sishc et al., Superoxide dismutase mimetic GC4419 protects against radiation induced lung fibrosis, exhibits antitumor effects, and enhances radiation induced cell killing, 1 pg 2015.
Sishc et al., Superoxide dismutase mimetic GC4419 sensitizes non-small cell lung cancer tumors to high dose per fraction radiation and ameliorates radiation induced lung fibrosis, 1 pg 2016.
Scarbrough, P.M., Inhibitors of glucose and hydroperoxide metabolism potentiate 17AAG-induced cancer cell killing via metabolic oxidative stress, University of Iowa Theses and Dissertations 2011.
Sobhakumari et al., Susceptibility of Human Head and Neck Cancer Cells to Combined Inhibition of Glutathione and Thioredoxin Metabolism, PLOS, 7(10): e48175, 10 pgs 2012.
Patent Cooperation Treaty, International Search Report for PCT/US2017/049960, 5pgs. Feb. 21, 2019.
Fritz et al., Intravenous vitamin C and cancer: A systematic review, Integrative Cancer Therapies, 13(4): 280-300 2014.
McConnell et al., Ascorbate combination therapy: New tool in the anticancer toolbox?, Science Translational Medicine, 6(222): 1-3 2014.
Patent Cooperation Treaty, International Search Report for PCT/US2019/016071, 4pgs. May 14, 2019.
Mapuskar et al., Mitochondrial Superoxide Increases Age-Associated Susceptability of Human Dermal Fibroblasts to Radiation and Chemotherapy, Cancer Research, 77(18): 5054-5067 2017.
European Patent Office, Extended Search Report for EP App. 17847659.4, 12 pages Mar. 6, 2020.
Salvemini et al., Reply to Role of manganese superoxide dismutase in cancer, Nature Medicine, 9(9): 1103-1103 Sep. 1, 2003.
Tovmasyan et al., Radiation-Mediated tumor growth inhibition is significantly enhanced with redox-active compounds that cycle with ascorbate, Antioxidants and Redox Signaling, 29(13): 1196-1214 Nov. 1, 2018.
Riley et al., Toward the rational design of superoxide dismutase mimics: mechanistic studies for the elucidation of substituent effects on the catalytic activity of macrocyclic manganese(II) complexes, JACS, 1997, 119(28): 6522-6528.
Salvemini et al., A nonpeptidyl mimic of superoxide dismutase with therapeutic activity in rats, Science, 1999, 286: 304-306 1999.
Sishc et al., The radioprotector GC4419 ameliorates radiation induced lung fibrosis while enhancing the response of non-small cell lung cancer tumors to high dose per fraction radiation exposures, American Association of Cancer Research, 1 pg. 2018.
Sichc et al. The superoxide dismutase mimetic GC4419 enhances tumor killing when combined with stereotactic ablative radition, BioRxiv Mar. 11, 2020.
Zhu et al. Lysine 68 acetylation directs MnSOD as a tetrameric detoxification complex versus a monomeric tumor promoter, Nature Communications Jun. 3, 2019.
European Patent Office, Extended European Search Report for 20168046.96, 16 pages Oct. 16, 2020.
Jiang et al., Role of IL-2 in cancer immunotherapy, Oncoimmunology, 5(6);E1163462 Apr. 25, 2016.
Lasry et al., Inflammatory networks underlying colorectal cancer, Nature Immunology, 17(3):230-240 Feb. 16, 2016.
Mikirova et al., Effect of high-dose intravenous vitamin C on inflammation in cancer patients, Journal of Translational Medicine, 10(189): 2 pages 2012.
Riley et al., Manganese Macrocyclic Ligand Complexes as Mimics of Superoxide Dismutase, J. Am. Chem. Soc. 116: 387-388 1994.
Pannala et al., Mechanistic Characterization of the Thioredoxin System in the Removal of Hydrogen Peroxide, Free Radic Biol Med., 78:42-55 2015.
Kelso et al., A Mitochondria-Targeted Macrocyclic Mn(II) Superoxide Dismutase Mimetic, Chemistry & Biology, 19: 1237-1246 2012.
European Patent Office, Extended European Search Report issued for App. No. 17166668.8, 11 pages Sep. 27, 2017.
Sindoni et al., Combination of immune checkpoint inhibitors and radiotherapy: Review of the literature, Critical Reviews in Oncology/Hematology, 2017, 113: 63-70 2017.
Pardoll, D. M., The blockade of immune checkpoints in cancer immunotherapy, Nat Rev Cancer, 2012. 12(4): 252-264 Mar. 22, 2012.
Patent Cooperation Treaty, International Search Report for PCT/US2018/027588, 5 pages Aug. 27, 2018.
Park et al., Synthesis and SOD activity of manganese complexes of pentaaza macrocycles containing amino-and guanidino-auxiliary, Bulletin of the Korean Chemical Society, 32(10): 3787-3789 2011.
Wagner, B. A., et al., Myeloperoxidase is involved in $H_2O_2$-induced apoptosis of HL-60 human leukemia cells, J. Biol. Chem, 2000, 272(29), 22461-9.
Chen, Q., et al., Pharmacologic ascorbic acid concentrations selectively kill cancer cells: action as a pro-drug to deliver hydrogen peroxide to tissues, PNAS, 2005, 102(38), 13604-9.
Rodriguez, et al., Mitochondrial or cytosolic catalase reverses the MnSOD-dependent inhibition of proliferation by enhancing respiratory chain activity, net ATP production, and decreasing the steady state levels of $H_2O_2$, Free Rad. Bio. & Med.
Alexandre, J., et al., Novel Action of Paclitaxel against Cancer Cells: Bystander Effect Mediated by Reactive Oxygen Species, Cancer Research, 2007, 67(8), 3512-3517.
Muscoli, C., et al., On the selectivity of superoxide dismutase mimetics and its importance in pharmacological studies, British Journal of Pharmacology, 2003, 140(3), 445-460.
Sawyer, D. T. et al., How super is superoxide?, Acc. Chem. Res., 1981, 14, 393-400.
Li, S., et al., The Role of Cellular Glutathione Peroxidase Redox Regulation in the Suppression of Tumor Cell Growth by Manganese Superoxide Dismutase, Cancer Res., 2000, 60(14), 3927-3939.
Buettner, G. R., et al., A New Paradigm: Manganese Superoxide Dismutase Influences the Production of $H_2O_2$ in Dells and Thereby Their Biological State, Free Radical Biology and Medicine, 2006, 41(8), 1338-50.
Day, B. J., Catalase and glutathione peroxidase mimics, Biochem Pharmacol, 2009, 77(3), 285-296.
Day, B. J. et al., Manganic Porphyrins Possess Catalase Activity and Protect Endothelial Cells against Hydrogen Peroxide-Mediated Injury, Arch. Biochem. & Biophysics, 1997, 347(2), 256-262.
Oberley, L. W., Mechanism of the tumor suppressive effect of MnSOD overexpression, Biomedicine & Pharmacotherapy, 2005, 59, 143-48 Mar. 19, 2005.
Rocklage et al., Manganese(II) N ,N'-Dipyridoxylethylenediamine-N ,N'-diacetate 5,5'- Bis(phosphate). Synthesis and Characterization of a Paramagnetic Chelate for Magnetic Resonance Imaging Enhancement, Inorg. Chem., 1989, 28, 477-485 Sep. 29, 1988.
European Patent Office, Extended Search Report issued for 12835035. 2, dated Mar. 9, 2015.
Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.
McCarthy, A., Metaphore Pharmaceuticals, Chemistry & Biology, 2003, 10(12): 1139-1140.
MacArthur et al., Modulation of serum cytokine levels by a novel superoxide dismutase mimetic, M40401, in an *Escherichia coli* model of septic shock: Correlation with preserved circulating catecholamines, Crit. Care Med., 2003, 31(1): 237245.

(56) References Cited

OTHER PUBLICATIONS

Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.

Salvemini et al., Nonpeptidyl mimetics of superoxide dismutase in clinical therapies for diseases, Cell and Mol Life Sci, 2000, 57: 1489-1492.

MacArthur et al., Inactivation of catecholamines by superoxide gives new insights on the pathogenesis of septic shock, PNAS, 2000, 97(17): 9753-9758.

Riley, P.A., Free radicals in biology: oxidative stress and the effects of ionizing radiation, Int. J. Radiat. Biol, 1994, 65(1): 27-33.

Shimizu et al., Neurprotection against hypoxia-ischemia in neonatal rat brain by novel superoxide dismutase mimetics, Neuroscience Letters, 2003, 346: 41-44.

Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.

Fike et al., Reactive oxygen species from NADPH oxidase contribute to altered pulmonary vascular responses in piglets with chronic hypoxia-induced pulmonary hypertension, 2008, 295(5): L881-L888.

Batinic-Haberle et al., The ortho effect makes manganese(III) meso-tetrakis(N-methylpyridinium-2-yl)porphyrin a powerful and potentially useful superoxide dismutase mimic, J Biol Chem, 1998, 273: 24521-24528.

Batinic-Haberle et al., Pure MnTBAP selectively scavenges peroxynitrite over superoxide:, Free Radic Biol Med, 2009, 46:192-201.

Day et al., Metalloporphyrins are potent inhibitors of lipid peroxidation, Free Radic Biol Med, 1999, 26: 730-736.

Day et al., A metalloporphyrin superoxide dismutase mimetic protects against paraquat-induced endothelial cell injury, in vitro, J Pharmacol Exp Ther, 1995, 275: 1227-1232.

Ferrer-Sueta et al., Reactions of Manganese Porphyrins with Peroxynitrite and Carbonate Radical Anion, J Biol Chem, 2003, 278: 27432-27438.

Kachadourian et al., Flavin-dependent antioxidant properties of a new series of meso-N,N'-dialkyl-imidazolium substituted manganese(III) porphyrins, Biochem Pharmacol, 2004, 67:77-85.

Szabo et al., Evaluation of the relative contribution of nitric oxide and peroxynitrite to the suppression of mitochondrial respiration in immunostimulated macrophages using a manganese, FEBS Letters, 1996, 381:82-86.

Murphy et al., Efficacy of Superoxide Dismutase Mimetic M40403 in Attenuating Radiation-Induced Oral Mucositis in Hamsters, Clin Cancer Res, 2008, 14(13): 4292-4297.

Salvemini et al., A nonpeptidyl mimic of superoxide dismutase with therapeutic activity in rats, Science, 1999, 286: 304-306.

Thompson et al., The manganese superoxide dismutase mimetic, M40403, protects adult mice from lethal total body irradiation, Free Radical Research, 2010; 44(5): 529-540.

Tuder et al., Oxidative stree and apoptosis interative and cause emphsema due to vascular endothelial growth factor receptor blockade, Am. J. Respir. Cell Mol. Biol., 2003, 29: 88-97.

Patent Cooperation Treaty, International Search Report issued for PCT/US2012/056921 dated Feb. 22, 2013, 5 pages.

Simic et al., Oxygen radicals in biology and medicine, Basic Life Sciences, 1988, vol. 49, Plenum Press, New York and London.

Weiss et al., Catalytic Efficacies of agents that dismutate superoxide, 1991, J. Cell, Biochem, Suppl. 15C, 216 Abstract C110.

Petkau, Scientific basis for the clinical use of superoxide dismutase, 1986, Cancer Treat. Rev. 13, 17.

McCord, Superoxide dismutase: Rationale for use in ruperfusion injury and inflammation, 1986, J. Free Radicals Biol. Med, 2, 307.

Bannister et al.. Aspects of the structure, function, and applications of superoxide dismutase, 1987, Crit. Rev. Biochem., 22, 111.

Gryglewski et al., Superoxide anion is involved in the breakdown of endothelium-derived vascular relaxing factor, 1986, Nature, 320, 454-456.

Palmer et al., Nitric oxide release accounts for the biological activity of endothelium derived relaxing factor, 1987, Nature, 327, 523-526.

Samlowski et al., A nonpeptidyl mimic of superoxide dismutase, M40403, inhibits does-limiting hyptension associated with interleukin-2 and increases its antitumor effects, 2003, Nature Medicine, 9, 750-755.

Riley et al., Structure-activity studies and the design of synthetic superoxide dismutase (SOD) mimetics as therapeutics, 2006, Advances in Inorganic Chemistry, 59, 233-263.

Riley et al., Synthesis, characterization, and stability of manganese(II) C-Substituted 1, 4, 7, 10, 12-Pentaazacyclopentadecane complexes exhibity superoxide dismutase activity, J. Inorg. Chem. 1996, 35: 5213-5231.

Salvemini et al., M40403: Superoxied dismutase mimic, Drugs of the Future, 2000, 25(10): 1027-1033.

Salvemini et al., SOD Mimetics are coming of age, Nature Reviews, 2002, 1: 367-374.

Aykin-Burns et al., Increased levels of superoxide and H2O2 mediate the differential susceptibility of cancer cells versus normal cells to glucose deprivation, Biochem J., 2009, 418: 29-37 2009.

COMBINATION CANCER IMMUNOTHERAPY WITH PENTAAZA MACROCYCLIC RING COMPLEX

The present disclosure generally relates to combination therapies for cancer treatment, including administration of a pentaaza macrocyclic ring complex in combination with an immunotherapy treatment.

Transition metal-containing pentaaza macrocyclic ring complexes having the macrocyclic ring system corresponding to Formula A have been shown to be effective in a number of animal and cell models of human disease, as well as in treatment of conditions afflicting human patients.

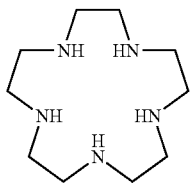

FORMULA A

For example, in a rodent model of colitis, one such compound, GC4403, has been reported to very significantly reduce the injury to the colon of rats subjected to an experimental model of colitis (see Cuzzocrea et al., *Europ. J. Pharmacol.*, 432, 79-89 (2001)).

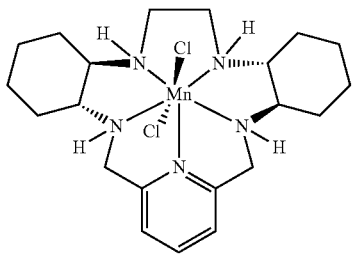

(4403)

GC4403 has also been reported to attenuate the radiation damage arising both in a clinically relevant hamster model of acute, radiation-induced oral mucositis (Murphy et al., *Clin. Can. Res.*, 14(13), 4292 (2008)), and lethal total body irradiation of adult mice (Thompson et al., *Free Radical Res.*, 44(5), 529-40 (2010)). Similarly, another such compound, GC4419, has been shown to attenuate VEGFr inhibitor-induced pulmonary disease in a rat model (Tuder, et al., *Am. J. Respir. Cell Mol. Biol.*, 29, 88-97 (2003)). Additionally, another such compound, GC4401 has been shown to provide protective effects in animal models of septic shock (S. Cuzzocrea, et. al., *Crit. Care Med.*, 32(1), 157 (2004) and pancreatitis (S. Cuzzocrea, et. al., *Shock*, 22(3), 254-61 (2004)).

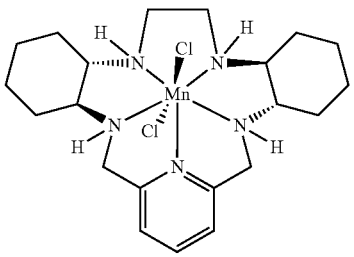

(4419)

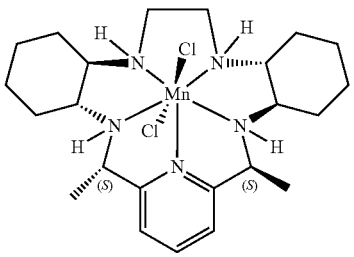

(4401)

Certain of these compounds have also been shown to possess potent anti-inflammatory activity and prevent oxidative damage in vivo. For example, GC4403 has been reported to inhibit inflammation in a rat model of inflammation (Salvemini, et. al., *Science*, 286, 304 (1999)), and prevent joint disease in a rat model of collagen-induced arthritis (Salvemini et al., *Arthritis & Rheumatism*, 44(12), 2009-2021 (2001)). Yet others of these compounds, MdPAM and MnBAM, have shown in vivo activity in the inhibition of colonic tissue injury and neutrophil accumulation into colonic tissue (Weiss et al., *The Journal of Biological Chemistry*, 271(42), 26149-26156 (1996)). In addition, these compounds have been reported to possess analgesic activity and to reduce inflammation and edema in the rat-paw carrageenan hyperalgesia model, see, e.g., U.S. Pat. No. 6,180,620.

Compounds of this class have also been shown to be safe and effective in the prevention and treatment of disease in human subjects. For example, GC4419 has been shown to reduce oral mucositis in head-and-neck cancer patients undergoing chemoradiation therapy (Anderson, C., *Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC)*, Oral Mucositis Research Workshop, MASCC/ISOO Annual Meeting on Supportive Care in Cancer, Copenhagen, Denmark (Jun. 25, 2015)).

In addition, transition metal-containing pentaaza macrocyclic ring complexes corresponding to this class have shown efficacy in the treatment of various cancers. For example, certain compounds corresponding to this class have been provided in combination with agents such as paclitaxel and gemcitabine to enhance cancer therapies, such as in the treatment of colorectal cancer and lung cancer (non-small cell lung cancer) (see, e.g., U.S. Pat. No. 9,998, 893) The 4403 compound above has also been used for treatment in in vivo models of Meth A spindle cell squamous carcinoma and RENCA renal carcinoma (Samlowski et al., *Nature Medicine*, 9(6), 750-755 (2003), and has also been used for treatment in in vivo models of spindle-cell squamous carcinoma metastasis (Samlowski et al., *Madame Curie Bioscience Database (Internet)*, 230-249 (2006)). The 4419 compound above has also been used in combination with cancer therapies such as cisplatin and radiation therapy to enhance treatment in in vivo models (Sishc et al., poster for Radiation Research Society (2015)).

Various cancer immunotherapies have also been developed that recruit the immune system to attack cancer cells to provide treatment. For example, recent immunotherapies have included the administration of immune checkpoint inhibitors, which help the immune system bypass the "checks" that may otherwise inhibit full activation and/or attack of the immune system against cancer cells. The drug ipilimunab is an example of such an immune checkpoint inhibitor, and has been approved for treatment of melanoma (Cameron et al., *Ipilimumab; First Global Approval*, Drugs (2011) 71(8), 1093-1094).

However, a need remains for enhanced methods for cancer treatment that provide improved efficacy in the killing of cancer cells.

Briefly, therefore, aspects of the present disclosure are directed to a method wherein a transition metal pentaaza-macrocyclic ring complex is administered to a patient prior to, concomitantly with, or after an inhibitor of immune response checkpoint inhibitor therapy for cancer, increasing the response of the tumors to the checkpoint inhibitor dose.

Another aspect of the present disclosure is directed to a method wherein a transition metal pentaaza-macrocyclic ring complex is administered to a patient prior to, concomitantly with or after an adoptive T-cell transfer therapy for cancer, increasing the response of the tumors to the adoptive T-cell transfer treatment.

Another aspect of the present disclosure is directed to a method wherein a transition metal pentaaza-macrocyclic ring complex is administered to a patient prior to, concomitantly with or after a therapeutic vaccine, increasing the response of the tumors to the therapeutic vaccine.

Another aspect of the present disclosure is directed to a method wherein a transition metal pentaaza-macrocyclic ring complex is administered to a patient prior to, concomitantly with or after a immunologic treatment for cancer, including those comprised of a compound, a composition, a device, or a procedure, increasing the response of the tumors to the immunologic treatment.

Another aspect of the present disclosure is directed to a method wherein a transition metal pentaaza-macrocyclic ring complex is administered to a patient suffering from a viral infection or other infectious disease, alone or in combination with one or more of an immune response checkpoint inhibitor, a T-cell transfer therapy, a therapeutic vaccine.

Another aspect of the present disclosure is directed to a method wherein a transition metal pentaaza-macrocyclic ring complex is administered to a patient for the purpose of increasing numbers of CD4+ or CD8+ T-cells, producing or increasing an immune response to a tumor or a viral infection.

Among the various aspects of the present disclosure, therefore, is method of treating a cancer in a mammalian subject afflicted with the cancer, the method including administering to the subject an immune checkpoint inhibitor, and administering to the subject a pentaaza macrocyclic ring complex corresponding to the formula (I) below, prior to, concomitantly with, or after administration of the immune checkpoint inhibitor, to increase the response of the cancer to the immune checkpoint inhibitor:

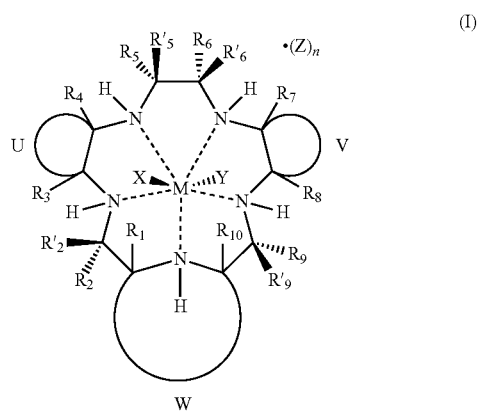

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

According to yet another aspect of the present disclosure, a method of treating a cancer in a mammalian subject afflicted with the cancer includes administering to the subject an adoptive T-cell transfer therapy, and administering to the subject a pentaaza macrocyclic ring complex corresponding to the formula (I) below, prior to, concomitantly with, or after the adoptive T-cell transfer therapy, to increase the response of the cancer to the adoptive T-cell transfer therapy,

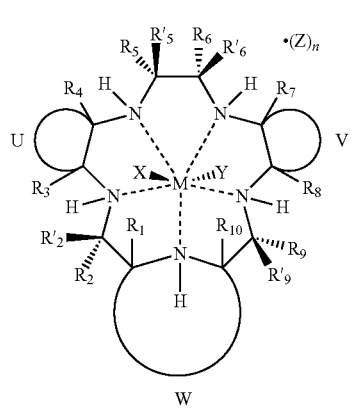 (I)

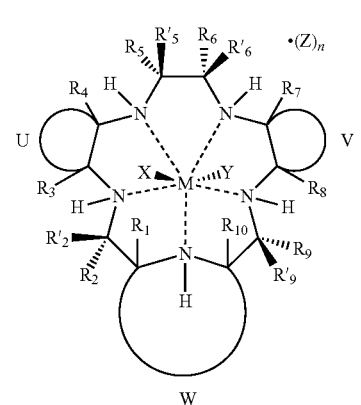 (I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

According to yet another aspect of the disclosure, a method of treating a cancer in a mammalian subject afflicted with the cancer includes administering to the subject a cancer vaccine, and administering to the subject a pentaaza macrocyclic ring complex corresponding to the formula (I) below, prior to, concomitantly with, or after administration of the cancer vaccine, to increase the response of the cancer to the cancer vaccine, wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

According to yet another aspect of the disclosure, a method of treating a viral infection in a mammalian subject in need thereof includes administering to the subject at least one of an immune checkpoint inhibitor, an adoptive T-cell transfer therapy, and a cancer vaccine, and administering to the subject a pentaaza macrocyclic ring complex corresponding to the formula (I) below, prior to, concomitantly with, or after administration of the at least one immune checkpoint inhibitor, adoptive T-cell transfer therapy, and cancer vaccine, to increase the effectiveness of the at least one immune checkpoint, adoptive T-cell transfer therapy, and cancer vaccine in treating the viral infection,

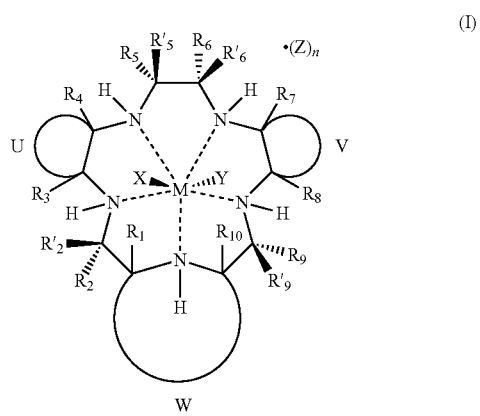 (I)

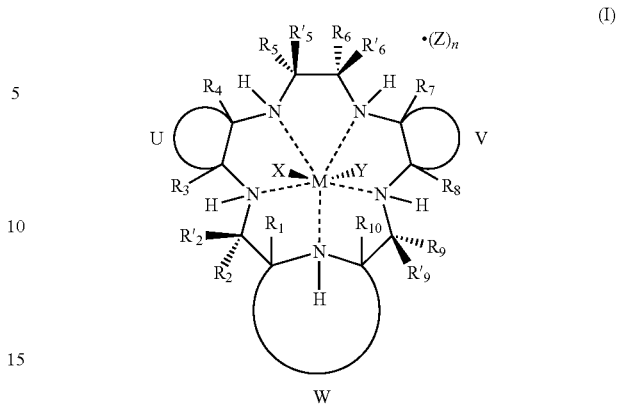 (I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

According to yet another aspect of the present disclosure, a kit for treating cancer includes at least one of an immune checkpoint inhibitor, T-cells for an adoptive T-cell transfer therapy, and a cancer vaccine, and a pentaaza macrocyclic ring complex according to formula (I), wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Other objects and features will be in part apparent and in part pointed out hereinafter.

ABBREVIATIONS AND DEFINITIONS

Figure 1:
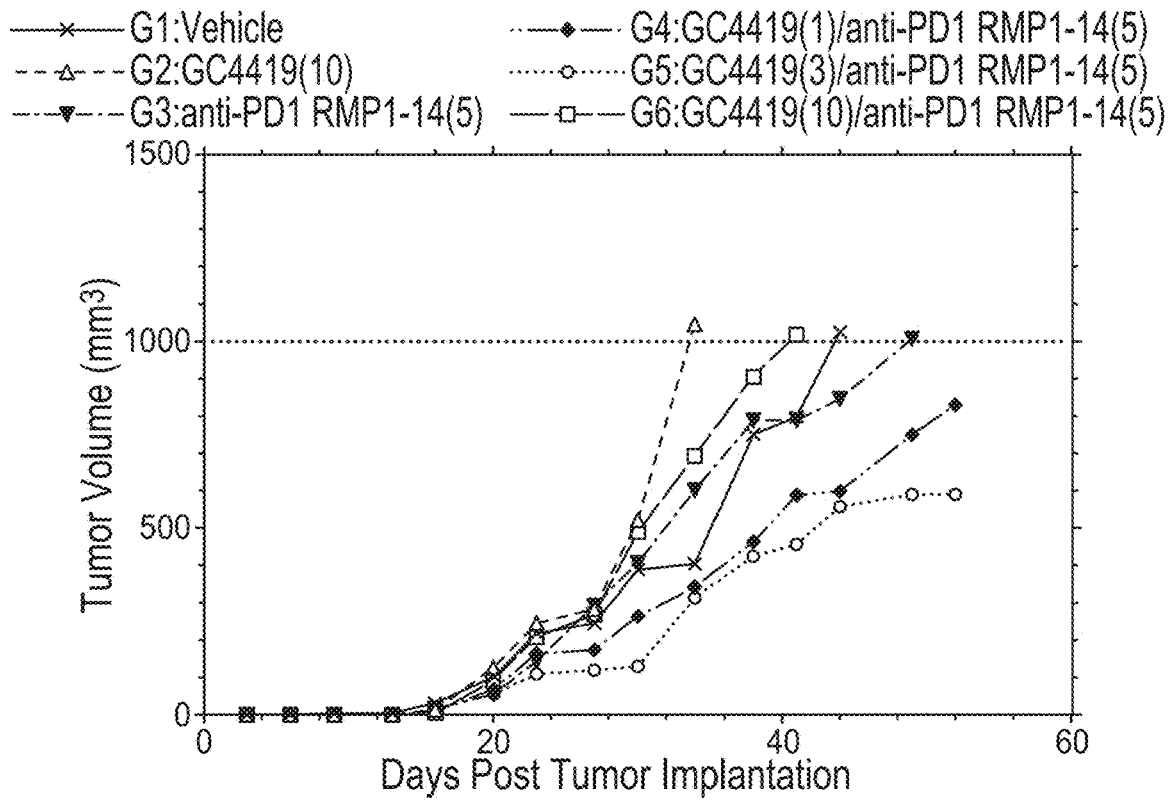
FIG. 1 shows median tumor volumes over a duration of treatment in a colon 26 cancer model using GC4419 and anti-PD1.
Figure 2:
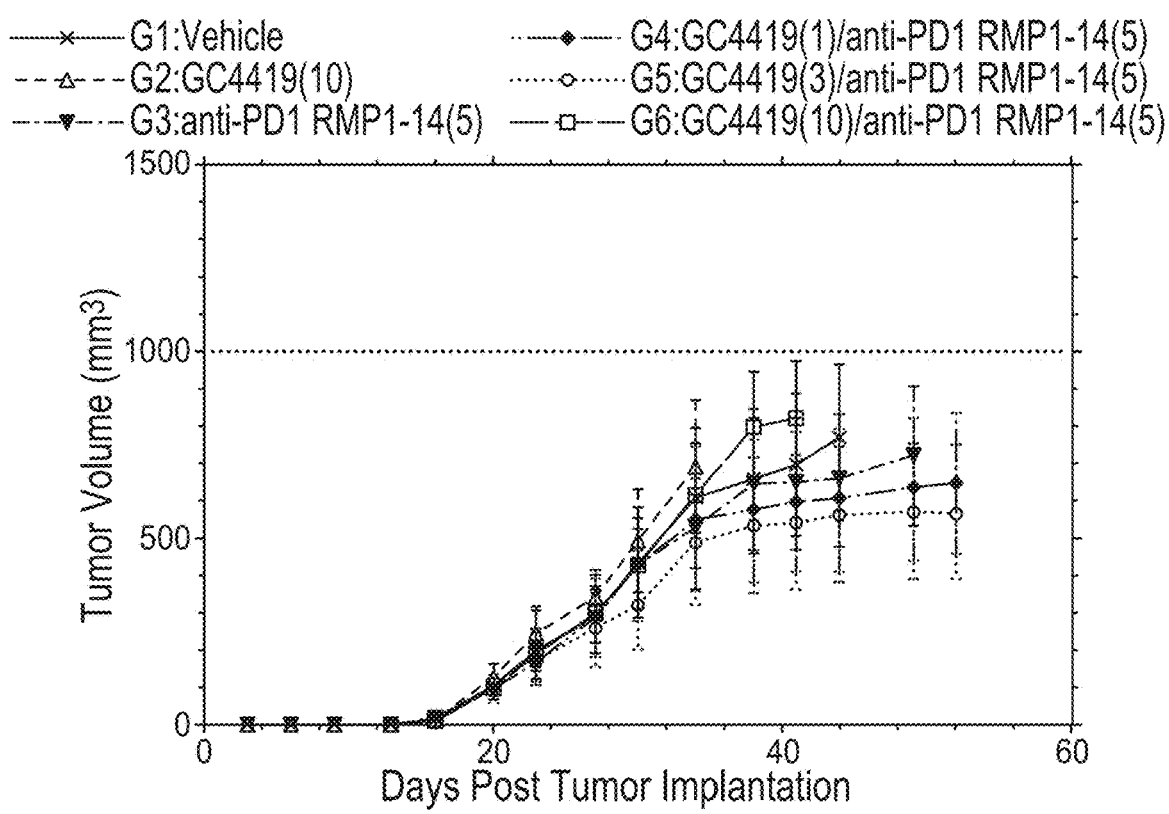
FIG. 2 shows mean tumor volumes over a duration of treatment in a colon 26 cancer model using GC4419 and anti-PD1.

The following definitions and methods are provided to better define the present invention and to guide those of ordinary skill in the art in the practice of the present invention. Unless otherwise noted, terms are to be understood according to conventional usage by those of ordinary skill in the relevant art.

"Acyl" means a —COR moiety where R is alkyl, haloalkyl, optionally substituted aryl, or optionally substituted heteroaryl as defined herein, e.g., acetyl, trifluoroacetyl, benzoyl, and the like.

"Acyloxy" means a —OCOR moiety where R is alkyl, haloalkyl, optionally substituted aryl, or optionally substituted heteroaryl as defined herein, e.g., acetyl, trifluoroacetyl, benzoyl, and the like.

"Alkoxy" means a —OR moiety where R is alkyl as defined above, e.g., methoxy, ethoxy, propoxy, or 2-propoxy, n-, iso-, or tert-butoxy, and the like.

"Alkyl" means a linear saturated monovalent hydrocarbon moiety such as of one to six carbon atoms, or a branched saturated monovalent hydrocarbon moiety, such as of three to six carbon atoms, e.g., $C_1$-$C_6$ alkyl groups such as methyl, ethyl, propyl, 2-propyl, butyl (including all isomeric forms), pentyl (including all isomeric forms), and the like.

Moreover, unless otherwise indicated, the term "alkyl" as used herein is intended to include both "unsubstituted alkyls" and "substituted alkyls," the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$," when used in conjunction with a chemical moiety, such as alkyl and aralkyl, is meant to include groups that contain from x to y carbons in the chain. For example, the term $C_{x-y}$ alkyl refers to substituted or unsubstituted saturated hydrocarbon groups, including straight chain alkyl and branched chain alkyl groups that contain from x to y carbon atoms in the chain.

"Alkylene" means a linear saturated divalent hydrocarbon moiety, such as of one to six carbon atoms, or a branched saturated divalent hydrocarbon moiety, such as of three to six carbon atoms, unless otherwise stated, e.g., methylene, ethylene, propylene, 1-methylpropylene, 2-methylpropylene, butylene, pentylene, and the like.

"Alkenyl" a linear unsaturated monovalent hydrocarbon moiety, such as of two to six carbon atoms, or a branched saturated monovalent hydrocarbon moiety, such as of three to six carbon atoms, e.g., ethenyl (vinyl), propenyl, 2-propenyl, butenyl (including all isomeric forms), pentenyl (including all isomeric forms), and the like.

"Alkaryl" means a monovalent moiety derived from an aryl moiety by replacing one or more hydrogen atoms with an alkyl group.

"Alkenylcycloalkenyl" means a monovalent moiety derived from an alkenyl moiety by replacing one or more hydrogen atoms with a cycloalkenyl group.

"Alkenylcycloalkyl" means a monovalent moiety derived from a cycloalkyl moiety by replacing one or more hydrogen atoms with an alkenyl group.

"Alkylcycloalkenyl" means a monovalent moiety derived from a cycloalkenyl moiety by replacing one or more hydrogen atoms with an alkyl group.

"Alkylcycloalkyl" means a monovalent moiety derived from a cycloalkyl moiety by replacing one or more hydrogen atoms with an alkyl group.

"Alkynyl" means a linear unsaturated monovalent hydrocarbon moiety, such of two to six carbon atoms, or a branched saturated monovalent hydrocarbon moiety, such as of three to six carbon atoms, e.g., ethynyl, propynyl, butynyl, isobutynyl, hexynyl, and the like.

"Alkoxy" means a monovalent moiety derived from an alkyl moiety by replacing one or more hydrogen atoms with a hydroxy group.

"Amino" means a —$NR^aR^b$ group where $R^a$ and $R^b$ are independently hydrogen, alkyl or aryl.

"Aralkyl" means a monovalent moiety derived from an alkyl moiety by replacing one or more hydrogen atoms with an aryl group.

"Aryl" means a monovalent monocyclic or bicyclic aromatic hydrocarbon moiety of 6 to 10 ring atoms e.g., phenyl or naphthyl.

"Cycle" means a carbocyclic saturated monovalent hydrocarbon moiety of three to ten carbon atoms.

"Cycloalkyl" means a cyclic saturated monovalent hydrocarbon moiety of three to ten carbon atoms, e.g., cyclopropyl, cyclobutyl, cyclopentyl, or cyclohexyl, and the like.

"Cycloalkylalkyl" means a monovalent moiety derived from an alkyl moiety by replacing one or more hydrogen atoms with a cycloalkyl group, e.g., cyclopropylmethyl, cyclobutylmethyl, cyclopentylethyl, or cyclohexylethyl, and the like.

"Cycloalkylcycloalkyl" means a monovalent moiety derived from a cycloalkyl moiety by replacing one or more hydrogen atoms with a cycloalkyl group.

"Cycloalkenyl" means a cyclic monounsaturated monovalent hydrocarbon moiety of three to ten carbon atoms, e.g., cyclopropenyl, cyclobutenyl, cyclopentenyl, or cyclohexenyl, and the like.

"Cycloalkenylalkyl" means a monovalent moiety derived from an alkyl moiety by replacing one or more hydrogen atoms with a cycloalkenyl group, e.g., cyclopropenylmethyl, cyclobutenylmethyl, cyclopentenylethyl, or cyclohexenylethyl, and the like.

"Ether" means a monovalent moiety derived from an alkyl moiety by replacing one or more hydrogen atoms with an alkoxy group.

"Halo" means fluoro, chloro, bromo, or iodo, preferably fluoro or chloro.

"Heterocycle" or "heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heteroaryl" means a monovalent monocyclic or bicyclic aromatic moiety of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

"Nitro" means $—NO_2$.

"Organosulfur" means a monovalent moiety a —SR group where R is hydrogen, alkyl or aryl.

"Substituted alkyl," "substituted cycle," "substituted phenyl," "substituted aryl," "substituted heterocycle," and "substituted nitrogen heterocycles" means an alkyl, cycle, aryl, phenyl, heterocycle or nitrogen-containing heterocycle, respectively, optionally substituted with one, two, or three substituents, such as those independently selected from alkyl, alkoxy, alkoxyalkyl, halo, hydroxy, hydroxyalkyl, or organosulfur.

"Thioether" means a monovalent moiety derived from an alkyl moiety by replacing one or more hydrogen atoms with an —SR group wherein R is alkyl.

As used herein, (i) the compound referred to herein and in the Figures as compound 401, 4401 or GC4401 is a reference to the same compound, (ii) the compound referred to herein and in the Figures as compound 403, 4403 or GC4403 is a reference to the same compound, (iii) the compound referred to herein and in the Figures as compound 419, 4419 or GC4419 is a reference to the same compound, and (iv) the compound referred to herein and in the Figures as compound 444, 4444 or GC4444 is a reference to the same compound.

DETAILED DESCRIPTION

Aspects of the present disclosure are directed to the treatment of cancer by administration of a pentaaza macrocyclic ring complex according to Formula (I), described below, in combination with an immunotherapeutic agent, to a subject suffering from cancer, to enhance response of the cancer to the immunotherapeutic agent.

In general, the immunotherapeutic agent may be an agent that is capable of stimulating or otherwise facilitating attack of the immune system on cancer cells or other cells. Examples of suitable immunotherapeutic agents can include, for example, immune checkpoint inhibitors, adoptive T-cell transfer therapy materials, and cancer vaccines. By providing the pentaaza macrocyclic ring complex in combination with the immunotherapeutic agent, it has been discovered that immune system activity can be enhanced to impart improved treatment of cancer in a subject suffering therefrom.

Accordingly, in one embodiment, aspects of the present disclosure comprise a method of treating a cancer in a mammalian subject by administering an immune checkpoint inhibitor, and a pentaaza macrocyclic ring complex corresponding to the formula (I) below. In yet another embodiment, aspects of the present disclosure comprise a method of treating a cancer in a mammalian subject by administering an adoptive T-cell transfer therapy, and a pentaaza macrocyclic ring complex corresponding to formula (I) below. In yet another embodiment, aspects of the present disclosure comprise a method of treating cancer in a mammalian subject by administering a cancer vaccine, and a pentaaza macrocyclic ring complex corresponding to formula (i) below. In yet another embodiment, a method of treatment of a viral infection by any of a checkpoint inhibitor, adoptive T-cell transfer, and cancer vaccine, can be enhanced by providing the pentaaza macrocyclic ring complex in combination with the treatment. Accordingly, the combination therapy can impart benefits in the treatment of cancer and viral infections, such as by facilitating the immunotherapeutic effects of the immunotherapeutic agent being provided as a part of the combination.

Transition Metal Pentaaza Macrocyclic Ring Complex

In one embodiment, the pentaaza macrocyclic ring complex corresponds to the complex of Formula (I):

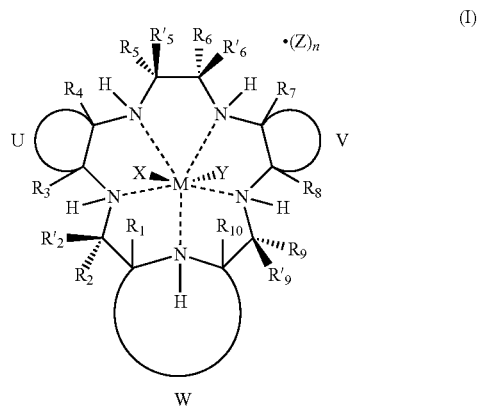

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

As noted above in connection with the pentaaza macrocyclic ring complex of Formula (I), M is $Mn^{2+}$ or $Mn^{3+}$. In one particular embodiment in which the pentaaza macrocyclic ring complex corresponds to Formula (I), M is $Mn^{2+}$. In another particular embodiment in which the pentaaza macrocyclic ring complex corresponds to Formula (I), M is $Mn^{3+}$.

In the embodiments in which one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are hydrocarbyl, for example, suitable hydrocarbyl moieties include, but are not limited to alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl. In one embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, or heterocyclyl. More preferably in this embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl (e.g., $C_1$-$C_6$ alkyl, more typically $C_1$-$C_4$ alkyl). Thus, for example, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ may be independently hydrogen, methyl, ethyl, propyl, or butyl (straight, branched, or cyclic). In one preferred embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl.

In one preferred embodiment in which the pentaaza macrocyclic ring complex corresponds to Formula (I), $R_1$, $R_2$, $R'_2$, $R_3$, $R_4$, $R_5$, $R'_5$, $R_7$, $R_8$, $R_9$, $R'_9$, and $R_{10}$ are each hydrogen and one of $R_6$ and $R'_6$ is hydrogen and the other of $R_6$ and $R'_6$ is methyl. In this embodiment, for example, $R_1$, $R_2$, $R'_2$, $R_3$, $R_4$, $R_5$, $R'_5$, $R_6$, $R_7$, $R_8$, $R_9$, $R'_9$, and $R_{10}$ may each be hydrogen while $R'_6$ is methyl. Alternatively, for example, $R_1$, $R_2$, $R'_2$, $R_3$, $R_4$, $R_5$, $R'_5$, $R'_6$, $R_7$, $R_8$, $R_9$, $R'_9$, and $R_{10}$ may each be hydrogen while $R_6$ is methyl. In another preferred embodiment in which the pentaaza macrocyclic ring complex corresponds to Formula (I), $R_1$, $R_3$, $R_4$, $R_5$, $R'_5$, $R'_6$, $R_7$, $R_8$, and $R_{10}$ are each hydrogen, one of $R_2$ and $R'_2$ is hydrogen and the other of $R_2$ and $R'_2$ is methyl, and one of $R_9$ and $R'_9$ is hydrogen and the other of $R_9$ and $R'_9$ is methyl. In this embodiment, for example, $R_1$, $R'_2$, $R_3$, $R_4$, $R_5$, $R'_5$, $R_7$, $R_8$, $R_9$, and $R_{10}$ may each be hydrogen while $R_2$ and $R'_9$ are methyl. Alternatively, for example, $R_1$, $R_2$, $R_3$, $R_4$, $R_5$, $R'_5$, $R_7$, $R_8$, $R'_9$, and $R_{10}$ may each be hydrogen while $R'_2$ and $R_9$ are methyl. In another embodiment in which the pentaaza macrocyclic ring complex corresponds to Formula (I), $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

In certain embodiments the U and V moieties are independently substituted or unsubstituted fused cycloalkyl moieties having 3 to 20 ring carbon atoms, more preferably 4 to 10 ring carbon atoms. In a particular embodiment, the U and V moieties are each trans-cyclohexanyl fused rings.

In certain embodiments the W moiety is a substituted or unsubstituted fused heteroaromatic moiety. In a particular embodiment, the W moiety is a substituted or unsubstituted fused pyridino moiety. Where W is a substituted fused pyridino moiety, for example, the W moiety is typically substituted with a hydrocarbyl or substituted hydrocarbyl moiety (e.g., alkyl, substituted alkyl) at the ring carbon atom positioned para to the nitrogen atom of the heterocycle. In a one preferred embodiment, the W moiety is an unsubstituted fused pyridino moiety.

As noted above, X and Y represent suitable ligands which are derived from any monodentate or polydentate coordinating ligand or ligand system or the corresponding anion thereof (for example benzoic acid or benzoate anion, phenol or phenoxide anion, alcohol or alkoxide anion). For example, X and Y may be selected from the group consisting of halo, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities. In one embodiment, X and Y if present, are independently selected from the group consisting of halo, nitrate, and bicarbonate ligands. For example, in this embodiment, X and Y, if present, are halo ligands, such as chloro ligands.

Furthermore, in one embodiment X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(═O)$R_{13}$ where $X_5$ is NH or O, and $R_{13}$ is C1-C18 alkyl, substituted or unsubstituted aryl or C1-C18 aralkyl, or —$OR_{14}$, where $R_{14}$ is C1-C18 alkyl, substituted or unsubstituted aryl or C1-C18 aralkyl, or together with $X_4$ is (═O); and each $X_4$ is independently hydrogen or together with $X_3$ is (═O).

In yet another embodiment, X and Y are independently selected from the group consisting of charge-neutralizing anions which are derived from any monodentate or polydentate coordinating ligand and a ligand system and the corresponding anion thereof; or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

In the pentaaza macrocyclic ring complex corresponding to Formula (I), Z is a counterion (e.g., a charge-neutralizing anion), wherein n is an integer from 0 to 3. In general, Z may correspond to counterions of the moieties recited above in connection for X and Y.

In combination, among certain preferred embodiments are pentaaza macrocyclic ring complexes corresponding to Formula (I) wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl;

U and V are each trans-cyclohexanyl fused rings;

W is a substituted or unsubstituted fused pyridino moiety;

X and Y are ligands; and

Z, if present, is a charge-neutralizing anion.

More preferably in these embodiments, M is $Mn^{2+}$; $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl; U and V are each trans-cyclohexanyl fused rings; W is an unsubstituted fused pyridino moiety; and X and Y are independently halo ligands (e.g., fluoro, chloro, bromo, iodo). Z, if present, may be a halide anion (e.g., fluoride, chloride, bromide, iodide).

In yet another embodiment, the pentaaza macrocyclic ring complex is represented by formula (II) below:

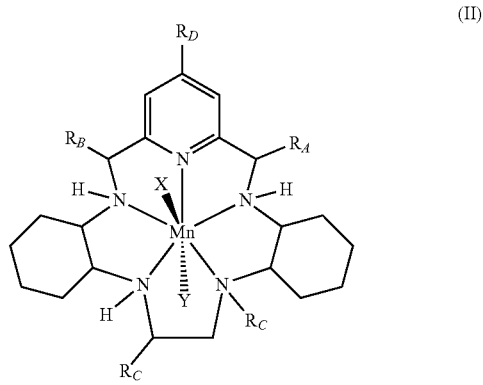

(II)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —N($OR_{11}$)($R_{12}$), —P(O)($OR_{11}$)($OR_{12}$), —P(O)($OR_{11}$)($R_{12}$), and —OP(O)($OR_{11}$)($OR_{12}$), wherein $R_{11}$ and $R_{12}$ are independently hydrogen or alkyl.

Furthermore, in one embodiment, the pentaaza macrocyclic ring complex is represented by formula (III) or formula (IV):

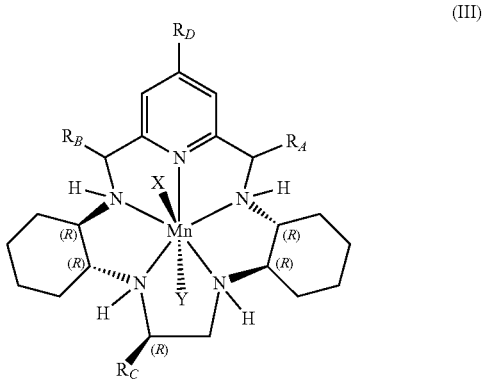

(III)

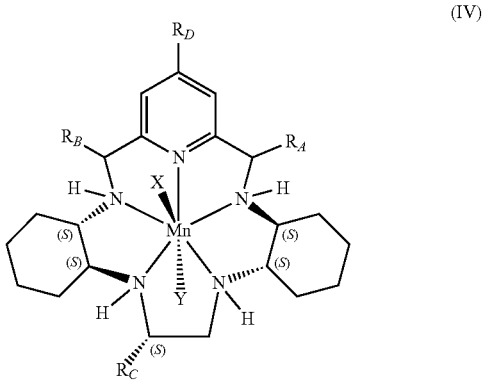

(IV)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

In yet another embodiment, the pentaaza macrocyclic ring complex is a compound represented by a formula selected from the group consisting of formulae (V)-(XVI):

(V)

(VI)

(VII)

(VIII)

(IX)

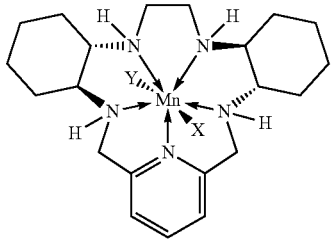

(X)

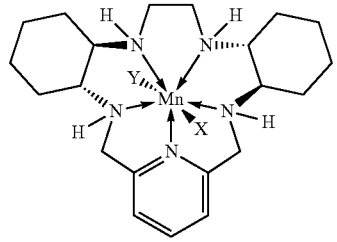

(XI)

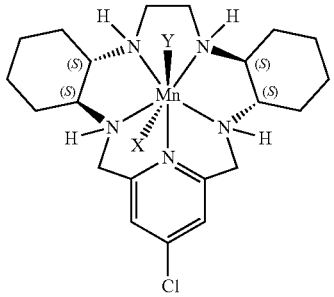

(XII)

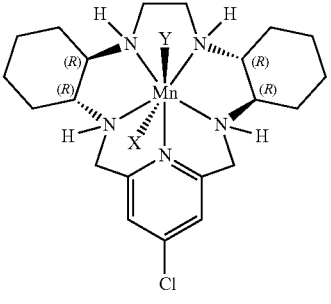

(XIII)

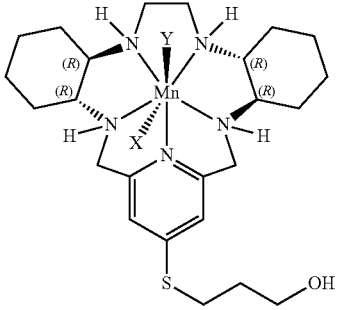

-continued

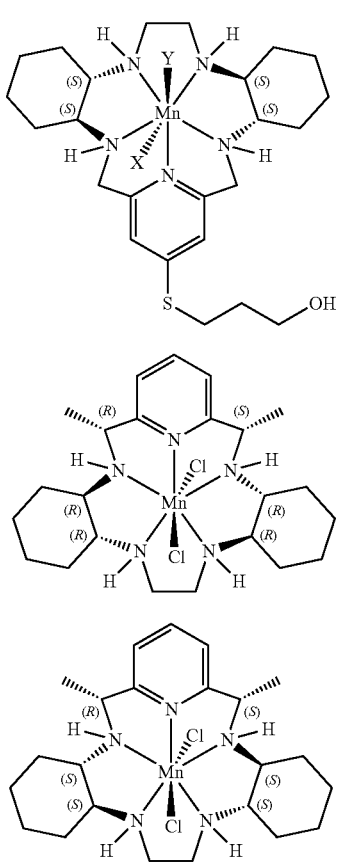

(XIV)

(XV)

(XVI)

In one embodiment, X and Y in any of the formulas herein are independently selected from the group consisting of fluoro, chloro, bromo and iodo anions. In yet another embodiment, X and Y in any of the formulas herein are independently selected from the group consisting of alkyl carboxylates, aryl carboxylates and arylalkyl carboxylates. In yet another embodiment, X and Y in any of the formulas herein are independently amino acids.

In one embodiment, the pentaaza macrocyclic ring complex has the following Formula (IA):

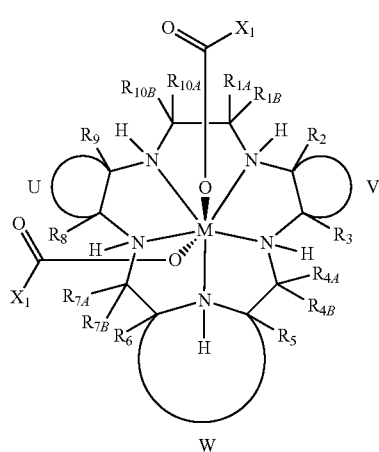

(IA)

wherein

M is $Mn^{2+}$ or $Mn^{3+}$;

$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen, hydrocarbyl, substituted hydrocarbyl, heterocyclyl, an amino acid side chain moiety, or a moiety independently selected from the group consisting of —$OR_{11}$, —$NR_{11}R_{12}$, —$COR_{11}$, —$C_2R_{11}$, —C(=O)$NR_{11}R_{12}$, —$SR_{11}$, —$SOR_{11}$, —$SO_2R_{11}$, —$SO_2NR_{11}R_{12}$, —$N(OR_{11})(R_{12})$, —P(=O)($OR_{11}$)($OR_{12}$), —P(=O)(O $R_{11}$)($R_{12}$), and —OP(=O)($OR_{11}$)($OR_{12}$), wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_5$ and $R_6$ attached to the carbon atoms which are both part of the heterocycle and the macrocycle are absent; wherein each $X_1$ is independently substituted or unsubstituted phenyl or —C(—$X_2$)(—$X_3$)(—$X_4$);

each $X_2$ is independently substituted or unsubstituted phenyl or alkyl;

each $X_3$ is independently hydrogen, hydroxyl, alkyl, amino, —$X_5$C(=O)$R_{13}$ where $X_5$ is NH or O, and $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl, or together with $X_4$ is (=O);

each $X_4$ is independently hydrogen or together with $X_3$ is (=O); and the bonds between the transition metal M and the macrocyclic nitrogen atoms and the bonds between the transition metal M and the oxygen atoms of the axial ligands —OC(=O)$X_1$ are coordinate covalent bonds.

In one embodiment, within Formula (IA), and groups contained therein, in one group of compounds $X_1$ is —C(—$X_2$)(—$X_3$)(—$X_4$) and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph |  | =O ($X_3$ and $X_4$ in combination) |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ |  | =O ($X_3$ and $X_4$ in combination) |

Furthermore, within embodiment (IA), and groups contained therein, in one group of compounds $X_1$ is $C(-X_2)(-X_3)(-X_4)$, and $X_3$ is $-X_5C(=O)R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | NHC(=O)$R_{13}$ | H |
| 2 | Ph | OC(=O)$R_{13}$ | H |
| 3 | $CH_3$ | NHC(=O)$R_{13}$ | H |
| 4 | $CH_3$ | OC(=O)$R_{13}$ | H | where $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl.

In one embodiment, the pentaaza macrocyclic ring complex corresponding to Formula (IA) is one of the complexes Formula (IE), such as $(IE_{R1})$, $(IE_{S1})$, $(IE_{R2})$, $(IE_{S2})$, $(IE_{R3})$, or $(IE_{S3})$:

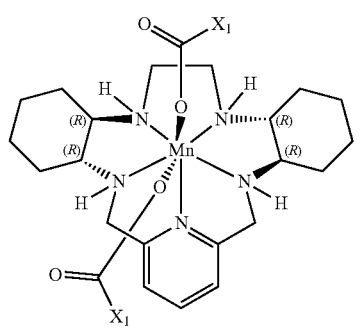

$(IE_{R1})$

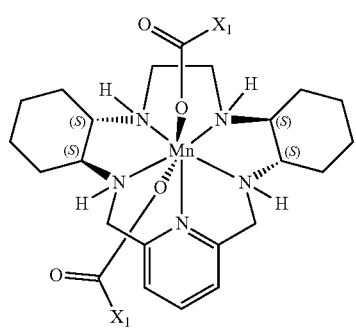

$(IE_{S1})$

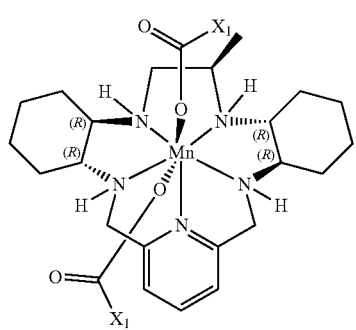

$(IE_{R2})$

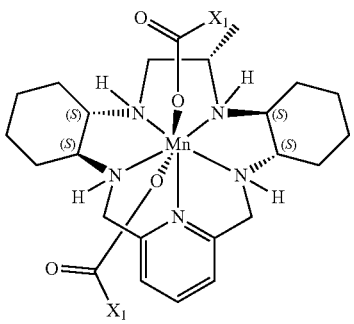

$(IE_{S2})$

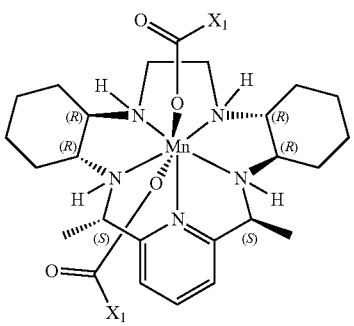

$(IE_{R3})$ $(IE_{S3})$ wherein
M is $Mn^{+2}$ or $Mn^{+3}$;
each $X_1$ is independently substituted or unsubstituted phenyl or $-C(X_2)(X_3)(X_4)$;
each $X_2$ is independently substituted or unsubstituted phenyl, methyl, ethyl, or propyl;
each $X_3$ is independently hydrogen, hydroxyl, methyl, ethyl, propyl, amino, or together with $X_4$ is =O;
each $X_4$ is independently hydrogen or together with $X_3$ is =O; and
the bonds between the manganese and the macrocyclic nitrogen atoms and the bonds between the manganese and the oxygen atoms of the axial ligands $-OC(O)X_1$ are coordinate covalent bonds.

In one embodiment, each $X_1$ is $-C(X_2)(X_3)(X_4)$ and each $-C(X_2)(X_3)(X_4)$ corresponds to any of combinations 1 to 9 appearing in the table for Formula (IA) above.

In yet another embodiment, the X and Y in pentaaza macrocyclic ring complex of Formula (I) correspond to the ligands in Formulas (IA) or (IE). For example, X and Y in the complex of Formula (I) may correspond to $-O-C(O)-X_1$, where $X_1$ is as defined for the complex of Formula (IA) and (IE) above.

In one embodiment, pentaaza macrocyclic ring complexes corresponding to Formula (I) (e.g., of Formula (I) or any of the subsets of Formula (I) corresponding to Formula (II)-(XIV), (IA) and (IE)), can comprise any of the following structures:
(4419)
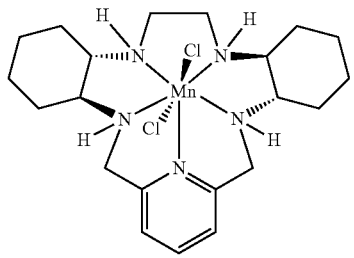
(4403)
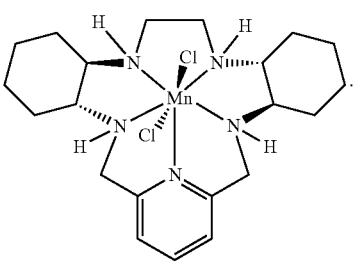
(4401)
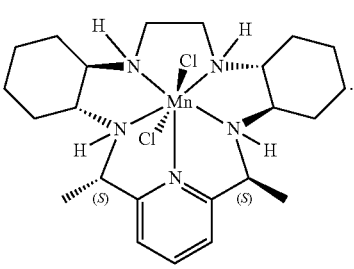
GC4444
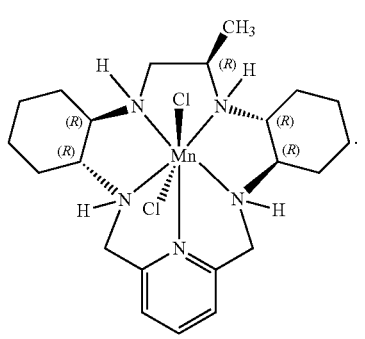
GC4702
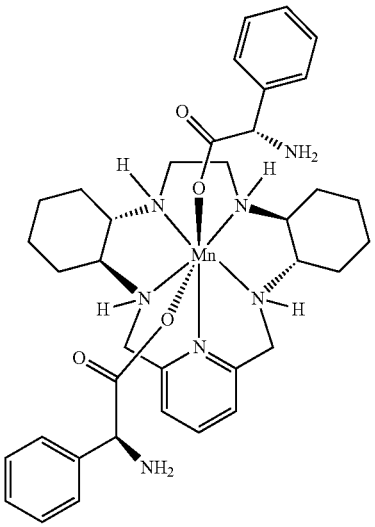
GC4711
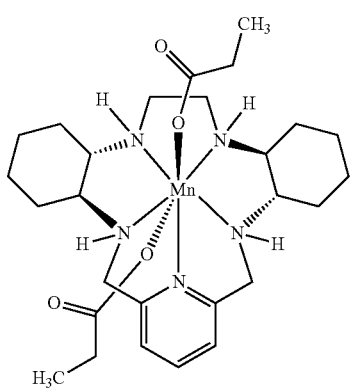
In one embodiment, pentaaza macrocyclic ring complexes for use in the methods and compositions described herein include those corresponding to Formulae (2), (3), (4), (5), (6), and (7):
2
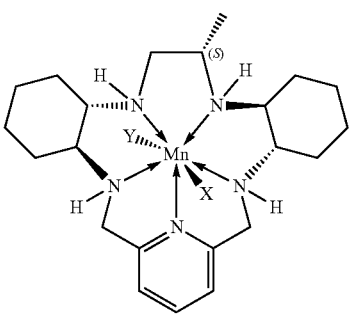

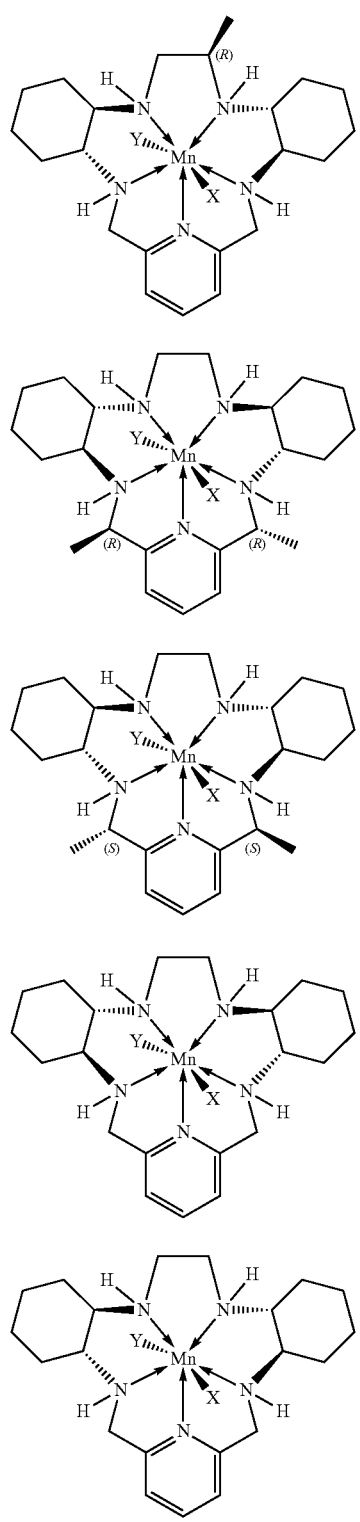

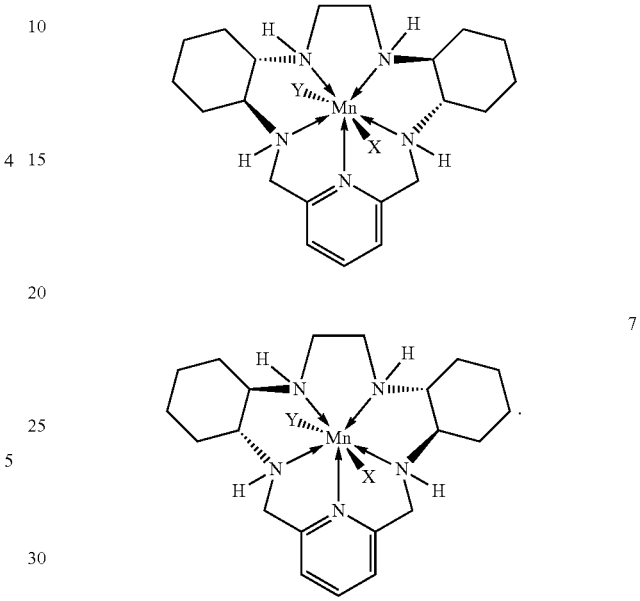

halo, such as chloro. Alternatively, X and Y may be ligands other than chloro, such as any of the ligands described above.

In another embodiment, the pentaaza macrocyclic ring complex corresponds to Formula (6) or Formula (7):

The chemical structures of 6 (such as the dichloro complex form described, for example, in Riley, D. P., Schall, O. F., 2007, Advances in Inorganic Chemistry, 59: 233-263) and of 7 herein (such as the dichloro complex form of 7), are identical except that they possess mirror image chirality; that is, the enantiomeric structures are non-superimposable.

For example, the pentaaza macrocyclic ring complex may correspond to at least one of the complexes below:

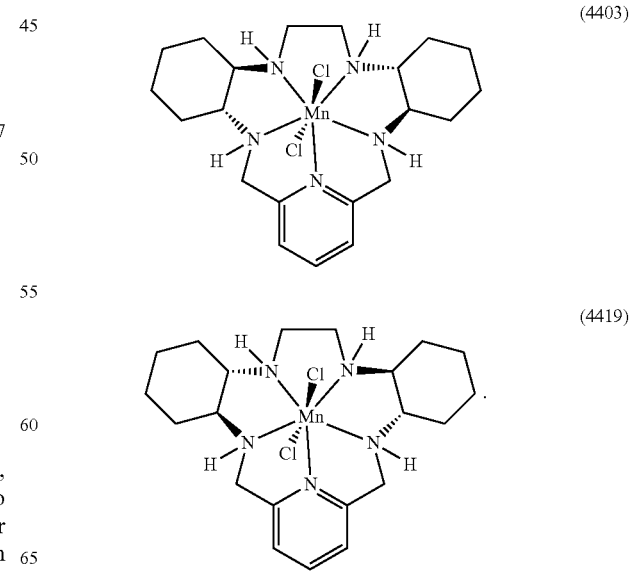

wherein X and Y in each of Formulae (2), (3), (4), (5), (6), and (7) are independently ligands. For example, according to one embodiment, the pentaaza macrocyclic ring complex for use in the methods and compositions described herein include those corresponding to Formulae (2), (3), (4), (5), (6), and (7) with X and Y in each of these formulae being In yet another embodiment, the pentaaza macrocyclic ring complex may correspond to at least one of the complexes below, and/or an enantiomer thereof:

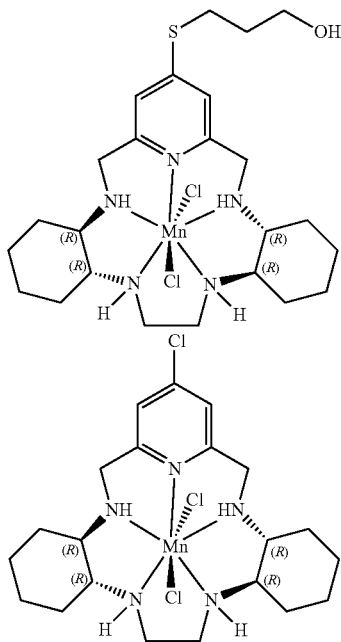

In one embodiment, the enantiomeric purity of the pentaaza macrocyclic ring complex is greater than 95%, more preferably greater than 98%, more preferably greater than 99%, and most preferably greater than 99.5%. As used herein, the term "enantiomeric purity" refers to the amount of a compound having the depicted absolute stereochemistry, expressed as a percentage of the total amount of the depicted compound and its enantiomer. In one embodiment, the diastereomeric purity of the pentaaza macrocyclic ring complex is greater than 98%, more preferably greater than 99%, and most preferably greater than 99.5%. As used herein, the term "diastereomeric purity" refers to the amount of a compound having the depicted absolute stereochemistry, expressed as a percentage of the total amount of the depicted compound and its diastereomers. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC). Similarly, enantiomeric purity can be determined by any analytical method capable of quantitatively distinguishing between a compound and its enantiomer. Examples of suitable analytical methods for determining enantiomeric purity include, without limitation, optical rotation of plane-polarized light using a polarimeter, and HPLC using a chiral column packing material.

In one embodiment, a therapeutically effective amount of the pentaaza macrocyclic ring complex may be an amount sufficient to provide a peak plasma concentration of at least 0.1 µM when administered to a patient. For example, in one embodiment, the pentaaza macrocyclic ring complex may be administered in an amount sufficient to provide a peak plasma concentration of at least 1 µM when administered to a patient. In yet another embodiment, the pentaaza macrocyclic ring complex may be administered in an amount sufficient to provide a peak plasma concentration of at least 10 µM when administered to a patient. Generally, the pentaaza macrocyclic ring complex will not be administered in an amount that would provide a peak plasma concentration greater than 40 µM when administered to a patient. For example, the pentaaza macrocyclic ring complex may be administered in an amount sufficient to provide a peak plasma concentration in the range of from 0.1 µM to 40 µM in a patient. As another example, the pentaaza macrocyclic ring complex may be administered in an amount sufficient to provide a peak plasma concentration in the range of from 0.5 µM to 20 µM in a patient. As another example, the pentaaza macrocyclic ring complex may be administered in an amount sufficient to provide a peak plasma concentration in the range of from 1 µM to 10 µM in a patient.

In yet another embodiment, a dose of the pentaaza macrocyclic ring complex that is administered per kg body weight of the patient may be at least 0.1 mg/kg, such as at least 0.2 mg/kg. For example, the dose of the pentaaza macrocyclic ring complex that is administered per kg body weight of the patient may be at least 0.5 mg/kg. As another example, the dose of the pentaaza macrocyclic ring complex that is administered per kg body weight of the patient may be at least 1 mg/kg. In another example, the pentaaza macrocyclic compound that is administered per kg body weight may be at least 2 mg/kg, such as at least 3 mg/kg, and even at least about 15 mg/kg, such as at least 24 mg/kg and even at least 40 mg/kg. Generally, the dose of the pentaaza macrocyclic ring complex that is administered per kg body weight of the patient will not exceed 1000 mg/kg. For example the dose of the pentaaza macrocyclic ring complex that is administered per kg body weight of the patient may be in the range of from 0.1 to 1000 mg/kg, such as from 0.2 mg/kg to 40 mg/kg, such as 0.2 mg/kg to 24 mg/kg, and even 0.2 mg/kg to 10 mg/kg. As another example, the dose of the pentaaza macrocyclic ring complex that is administered per kg body weight may be in a range of from 1 mg/kg to 1000 mg/kg, such as from 3 mg/kg to 1000 mg/kg, and even from 5 mg/kg to 1000 mg/kg, such as 10 mg/kg to 1000 mg/kg. As another example, the dose of the pentaaza macrocyclic ring complex that is administered per kg body weight may be in a range of from 2 mg/kg to 15 mg/kg. As yet another example, the dose of the pentaaza macrocyclic ring complex that is administered per kg body weight may be in a range of from 3 mg/kg to 10 mg/kg. As another example, the dose of the pentaaza macrocyclic ring complex that is administered per kg body weight of the patient may be in the range of from 0.5 to 5 mg/kg. As yet a further example, the dose of the pentaaza macrocyclic ring complex that is administered per kg body weight of the patient may be in the range of from 1 to 5 mg/kg.

In one embodiment, the dosages and/or plasma concentrations discussed above may be particularly suitable for the pentaaza macrocyclic ring complex corresponding to GC4419, although they may also be suitable for other pentaaza macrocyclic ring complexes. In addition, one or ordinary skill in the art would recognize how to adjust the dosages and/or plasma concentrations based on factors such as the molecular weight and/or activity of the particular compound being used. For example, for a pentaaza macrocyclic ring complex having an activity twice that of GC4419, the dosage and/or plasma concentration may be halved, or for a pentaaza macrocyclic ring complex having a higher molecular weight that GC4419, a correspondingly higher dosage may be used.

The dosing schedule of the pentaaza macrocyclic ring complex can similarly be selected according to the intended treatment. For example, in one embodiment, a suitable dosing schedule can comprise dosing a patient at least once per week, such as at least 2, 3, 4, 5, 6 or 7 days per week (e.g., daily), during a course of treatment. As another example, in one embodiment, the dosing may be at least once a day (qd), or even at least twice a day (bid). In one embodiment, the course of treatment with the pentaaza macrocyclic ring complex may last at least as long as a course of treatment with an immunotherapeutic agent, such as an immune checkpoint inhibitor, and may even exceed the duration during which the immunotherapeutic agent is provided. The course of therapy with the pentaaza macrocyclic ring complex may also start on the same date as treatment with the immunotherapeutic agent, or may start sometime after initial dosing with the immunotherapeutic agent, as is discussed in more detail below. For example, in one embodiment, for a checkpoint inhibitor that is administered for a course of therapy lasting 9 weeks, the pentaaza macrocyclic ring complex may be administered for a course of therapy lasting at least 3 weeks, and even at least 4 weeks, such as at least 6 weeks and even up to at least 9 weeks.

Immune Checkpoint Inhibitors

According to one embodiment, an immune checkpoint inhibitor is provided as a part of a method of treatment herein, in combination with the pentaaza macrocyclic compound. Immune checkpoints are inhibitory pathways in the immune system that maintain self-tolerance and modulate the duration and amplitude of immune response to minimize damage that could otherwise be inflicted by an excessive immune response. Without being limited by any specific theory, it is believed that cancer cells can co-opt the immune checkpoints to provide immune resistance, such as against T cells that are specific for tumor antigens. That is, cancer cells may be capable of activating an immune system checkpoint to inhibit immune response to the cancel cells. Accordingly, by providing an immune checkpoint inhibitor that is capable of inhibiting the immune checkpoint, the immune response against the cancer cells can be facilitated.

Accordingly, in one embodiment, an immune checkpoint inhibitor can comprise any agent that blocks or inhibits a checkpoint on the immune system or immune response. For example, many immune checkpoints are regulated by interactions between a specific receptor and a ligand, such as the interaction between the PD-1 receptor expressed on the surface of activated T cells, and its ligands PDL-1 and PDL-2 that are expressed on the surface of antigen-presenting cells. Cancer cells can co-opt this interaction by presenting high levels of PDL-1 on their surface to interact with the PD-1 receptor of T-cells, thus activating this "checkpoint" of the immune system and suppressing the immune response. Accordingly, in one embodiment, an immune checkpoint inhibitor can be any one or more of a small molecule inhibitor (generally, an inhibitor having a molecular weight of <900 daltons), an antibody, an antigen binding fragment of an antibody, and an Ig fusion protein that is capable of blocking or inhibiting an immune checkpoint, such as by blocking or inhibiting immune checkpoint receptors or blocking or inhibiting immune checkpoint receptor ligands.

In one embodiment, the immune checkpoint inhibitor interacts with (e.g., by inhibiting) one or more of cytotoxic T-lymphocyte antigen 4 (CTLA4), programmed death 1 (PD-1), programmed death ligand 1 (PDL-1), PDL-2, lymphocyte activation genes-3 (LAG3), B7 homolog 3 (B7-H3), B7 homolog 4 (B7-H4), indoleamine (2,3)-dioxygenase (IDO), adenosine A2a receptor (A2AR), neuritin, B- and T-lymphocyte attenuator (BTLA), killer immunoglobulin-like receptors (KIR), T cell immunoglobulin and mucin domain-containing protein 3 (TIME-3), inducible T cell costimulator (ICOS), CD27, CD28, CD40, CD137, CD160, CD244, HVEM, GAL9, VISTA, 2B4, CGEN-15049, CHK 1, CHK 2, GITR, CD47 and combinations thereof. In one embodiment, the immune checkpoint inhibitor is a T-cell checkpoint inhibitor. For example, in one embodiment, the checkpoint inhibitor may interact with one or more of CTLA4, PD-1 and PDL-1 or PDL-2.

For example, the checkpoint inhibitor may be at least one of an anti-CTLA4 antibody, an anti-PD-1 antibody, and anti-PDL-1 antibody, and an anti-PDL-2 antibody. As used herein "antibody" and "antigen-binding fragments" include naturally occurring immunoglobulins (e.g., IgM, IgG, IgD, IgA, IgE) as well as non-naturally occurring immunoglobulins, such as single chain antibodies, chimeric antibodies (e.g., humanized antibodies), heteroconjugate antibodies, Fab', F(ab')2, Fab, Fv and rIgG. An "antigen-binding fragment" is a portion of an antibody that is capable of recognizing an antigen. Furthermore, antibodies or antigen-binding fragments can include but are not limited to polyclonal, monoclonal, multispecific, human, humanized, primatized and/or chimeric antibodies.

In one embodiment, the immune checkpoint inhibitor is selected from the group consisting of ipilimumab (YERVOY (Bristol-Myers Squibb), nivolumab (Bristol-Meyers Squibb), pembrolizumab (Merck), pidilizumab (Curetch), arelumab (Merck Serono), tremelimumab (Pfizer), atezolizumab, AMP-224 (GlaxoSmithKline/Amplimmune), MPDL3280A (Roche), MDX-1105 (Medarex, Inc/Bristol-Meyer Squibb), MDX-1106, MEDI-4736, IMP321, INCB024360, NLG-919, indoximod, AUNP 12, galiximab (Biogen Idec), avelumab (EMD Serono), varlilumab (CellDex Therapeutics), mogamulizumab (Kyowa Hakko Kirin), CP-870,893, MEDI-6469 (MedImmune), IPH2101 (Innate Pharma/Bristol-Meyers Squibb), urelumab (Bristol-Meyers Sqiubb), lirilumab (Bristol-Meyers Squibb), BMS-986016 (Bristol-Meyers Squibb), MGA271, IMP321, BMS-936559, MSB0010718C, anti-OX40, MK-3475, CT-011, BY55, AMP224, and BGB-A317.

The dose of the immune checkpoint inhibitor can be selected according to the treatment to be provided and the particular immune checkpoint inhibitor being used. For example, a suitable dose of an immune checkpoint inhibitor may be at least at least 0.1 mg/kg. For example, the dose of the immune checkpoint inhibitor that is administered per kg body weight of the patient may be at least 0.5 mg/kg. As another example, the dose of the immune checkpoint inhibitor that is administered per kg body weight of the patient may be at least 1 mg/kg. In another example, the immune checkpoint inhibitor that is administered per kg body weight may be at least 2 mg/kg, such as at least 3 mg/kg, and even at least 10 mg/kg, such as at least 15 mg/kg. Generally, the dose of the immune checkpoint inhibitor that is administered per kg body weight of the patient will not exceed 20 mg/kg, such as a dose that does not exceed 15 mg/kg, and even that does not exceed 10 mg/kg. For example the dose of the immune checkpoint inhibitor that is administered per kg body weight of the patient may be in the range of from 0.1 to 15 mg/kg. As another example, the dose of the immune checkpoint inhibitor that is administered per kg body weight may be in a range of from 2 mg/kg to 15 mg/kg. As yet another example, the dose of the immune checkpoint inhibitor that is administered per kg body weight may be in a range of from 3 mg/kg to 10 mg/kg.

The dosing schedule of the immune checkpoint inhibitor can similarly be selected according to the intended treatment and the particular immune checkpoint inhibitor being provided. For example, in one embodiment, a suitable dosing schedule in one embodiment can comprise dosing a patient once every 2 or 3 weeks, for a total of 4 doses (9 weeks of treatment total). That is, in some embodiments treatment may involve a course of therapy that lasts at least 9 weeks and even 10 weeks, but in some embodiments may not extend past 16 weeks. In particular, the package insert for Yervoy (ipilimumab) indicates that a dose of 3 mg/kg should be given every 3 weeks for 4 doses, as given by IV over the course of 90 minutes. Dosage regimens for Opdivo (nivolumab) and Keytruda (pembrolizumab) similarly indicate dosing once every 2 or 3 weeks.

Adoptive T-Cell Transfer Therapies

According to one embodiment, an adoptive T-cell transfer therapy is provided as a part of a method of treatment herein, in combination with the pentaaza macrocyclic compound. In adoptive cell therapy, cells are removed from a donor and cultured and/or manipulated in vivo, after which they are administered to the patient for treatment. For example, cancer-specific cytotoxic T-cells can be cultured and/or modified to provide for the targeting and destroying of cancer cells in a patient. In one embodiment, an adoptive T-cell transfer therapy comprises administering to the subject cancer-specific autologous T-cells (i.e., cells originally obtained from the same patient). In another embodiment, the adoptive T-cell transfer therapy comprises administering to the subject cancer-specific allogeneic T-cells (i.e., cells originally obtained from a donor). The cancer specific T-cells can facilitate immune system attack of the cancer cells to provide for treatment of the cancer in the subject.

In one embodiment, the adoptive T-cell transfer therapy comprises providing autologous tumor infiltrating lymphocytes. For example, in one embodiment, tumor infiltrating lymphocytes (TILs) can be expanded ex vivo from tumor fragments from a patient, and transplanted back into the subject. In one embodiment, the TILS are expanded by placing in a growth medium and exposing to a high dose of IL-2. Once the TILs have been sufficiently expanded, a patient may receive the cells via infusions, such as via 1 to 2 infusions separated by 1-2 weeks.

In yet another embodiment, the adoptive T-cell transfer therapy comprises providing antigen-expanded CD8+ and/or CD4+ T cells. For example, in one embodiment, peripheral blood lymphocytes can be harvested and expanded in vitro through antigen-specific expansion to produce tumor-specific T cells. In yet another embodiment, the adoptive T-cell transfer therapy comprises providing genetically modified T cells that express T-cell receptors (TCR) that recognize tumor antigens For example, in one embodiment, peripheral blood lymphocytes can be harvested and genetically engineered to produce tumor-specific T cells with TCRs that specifically recognize cancer antigens, such as by transducing lymphocytes with a retrovirus that contains genes encoding the tumor-antigen-specific TCR. The tumor-specific T-cells can be provided to the patient by one or more infusions of the cells, as discussed above.

According to one aspect, the dosing regimen and schedule for the adoptive T-cell transfer process can be selected according to the treatment to be provided and the type of cells to be transferred, and the dosing regimen and schedule may further be coordinated with dosing with the pentaaza macrocyclic ring complex, as is discussed in more detail below.

Cancer Vaccines

According to one embodiment, a cancer vaccine is provided as a part of a method of treatment herein, in combination with the pentaaza macrocyclic compound. Cancer vaccines may help prime and mobilize the immune system to attack cancer cells in the body, and may use, for example, cancer cells or parts of cancer cells, or antigens, to invoke or increase the immune response to cancer cells in the patient.

In one embodiment, the cancer vaccine is selected from the group consisting of tumor cell vaccines, antigen vaccines, dendritic cell vaccines, DNA vaccines and vector based vaccines. For example, a tumor cell vaccine can comprise can cancer cells that have been removed from a subject and then modified so they cannot reproduce, such as by exposing to radiation, as well as optionally by modifying to make the cells more visible to the immune system. The modified tumor cells can then be provided to a subject to train the subject's immune system to recognize the cancer cells and go after other such cancer cells in the subject's body. The tumor cell vaccines can be either autologous (from the subject themselves) or allogeneic (from a donor). Antigen vaccines provide one or more antigens, typically specific for a certain type of cancer, to train the immune system to recognize the cancer-specific antigens. Dendritic cell vaccines involve exposing immune cells in vitro to antigens and other chemicals that convert them into dendritic cells, after which the dendritic cells are injected back into a subject to provoke an immune response. DNA vaccines and vector vaccines can be used to program cells to express specific antigens to provoke an immune response.

In one embodiment, a cancer vaccine for use in treatment can be selected from the group consisting of M-Vax (Avax Technologies), Provenge (Dendreon), GRNVAC1 (Geron), Bexidem (IDM Pharma), Uvidem (IDM Pharma), Collidem (IDM Pharma), INGN 225 (Introgen Therapuetics), M3Tk (MolMed), DC-Vax (Northwest Biotherapuetics), CVac (Prima Biomed), GVAX (Cell Genesys), Lucanix (NovaRx), Onyvax-P (Onyvax), HSPP-96 Oncophage (Antigenics), BiovaxlD (Biovest International), NeuVax (Apthera), CDX-110 (CeppDex), GV1001 (Pharmexa), CYT004-MelQbG10 (Cytos Biotechnology), li-Key/HER2/neu (Generiex Biotechnology), MAGE-A3 (Glaxo-SmithKline Biologicals), IDM-2101 (IDM Pharma), IMA901IMA910 (Immatics Biotechnologies), melanoma cancer vaccine (Norwood Immunology), inCVAX (Immunophotonics)) and Stimuvax (Oncothyreon).

Timing of Administration

In one embodiment, a treatment regimen can comprise administering an initial dose of the pentaaza macrocyclic complex after a predetermined period of time has elapsed since administration of an initial dose of an immunotherapeutic agent. That is, the treatment regimen can comprise administering an initial dose and optionally one or more subsequent doses of the immunotherapeutic agent, with the onset of dosing with the pentaaza macrocyclic ring complex being delayed for a predetermined period of time after the initial immunotherapeutic agent dose. Unexpectedly, it has been discovered that delaying the initial administration of the pentaaza macrocyclic ring complex until a predetermined time after treatment with the immunotherapeutic agent has begun, can provide significantly improved results over treatment where dosing with the immunotherapeutic agent and pentaaza macrocyclic ring complex is started closer to the same time.

For example, in an embodiment where an immune checkpoint inhibitor is being administered, the initial administration of the pentaaza macrocyclic ring complex in a course of therapy may be performed after a predetermined period of time has elapsed since an initial administration of the immune checkpoint inhibitor to start a course of therapy. In one embodiment, the initial administration of the pentaaza macrocyclic ring complex in a course of therapy may be no less than 3 days after the initial administration of the immune checkpoint inhibitor (for example, if the immune checkpoint inhibitor is administered on day 1 of treatment, the pentaaza macrocyclic ring complex is administered no sooner than on day 4 of treatment). In another embodiment, the initial administration of the pentaaza macrocyclic ring complex in a course of therapy may be no less than 6 days after the initial administration of the immune checkpoint inhibitor (for example, if the immune checkpoint inhibitor is administered on day 1 of treatment, the pentaaza macrocyclic ring complex is administered no sooner than on day 7 of treatment). In yet another embodiment, the initial administration of the pentaaza macrocyclic ring complex in a course of therapy may be no less than 2 weeks after the initial administration of the immune checkpoint inhibitor. In yet another embodiment, the initial administration of the pentaaza macrocyclic ring complex in a course of therapy may be no less than 3 weeks after the initial administration of the immune checkpoint inhibitor. In yet another embodiment, the initial administration of the pentaaza macrocyclic ring complex in a course of therapy may be no less than 6 weeks after the initial administration of the immune checkpoint inhibitor. Generally, the initial administration of the pentaaza macrocyclic ring complex in a course of therapy will be within 9 weeks of the initial administration of the immune checkpoint inhibitor. For example, the initial administration of the pentaaza macrocyclic ring complex in a course of therapy can be in the range of from 3 days to 9 weeks after the initial administration of the immune checkpoint inhibitor. In one embodiment, an initial administration of the pentaaza macrocyclic ring complex in the course of therapy follows at least two doses of the immune checkpoint inhibitor. In another embodiment, an initial administration of the pentaaza macrocyclic ring complex in the course of therapy follows at least three doses of the immune checkpoint inhibitor. In another embodiment, an initial administration of the pentaaza macrocyclic ring complex in the course of therapy follows at least four doses of the immune checkpoint inhibitor. In another embodiment, an initial administration of the pentaaza macrocyclic ring complex in the course of therapy follows at least five doses of the immune checkpoint inhibitor. As an example, in one embodiment where a course of treatment with a checkpoint inhibitor involves dosing once every 3 weeks for 4 total doses, the initial administration of the pentaaza macrocyclic ring complex can be provided not less than 3 days after the initial immune checkpoint inhibitor dose, but no more than 9 weeks after the initial immune checkpoint inhibitor dose, meaning that administration of the pentaaza macrocyclic ring complex may be delayed until before the final dose of the immune checkpoint inhibitor given during a course of therapy. Furthermore, in one embodiment, the initial administration of the pentaaza macrocyclic ring complex may be delayed with respect to an initial administration of the immune checkpoint inhibitor until after at least a second dose of the immune checkpoint inhibitor has been administered, such as after a third dose of the immune checkpoint inhibitor has been administered, and even after a fourth dose of the immune checkpoint inhibitor has been administered. Furthermore, other dosing schemes other than those specifically mentioned herein may also be provided.

It yet another embodiment, it has been unexpectedly found that improved results in terms of treatment can be provided by dosing with the pentaaza macrocyclic ring complex on a day that is other than a day on which dosing with the immunotherapeutic agent is provided. For example, dosing with a pentaaza macrocyclic ring complex on separate days from the days on which immune checkpoint inhibitors are dosed, that is, skipping administration of the pentaaza macrocyclic ring complex on days when the immune checkpoint inhibitor is being administered, provides improved benefits in terms of the immune response. Accordingly, in one embodiment, doses of the pentaaza macrocyclic ring complex that are provided in a course of cancer treatment are provided on separate days from any dose of an immune checkpoint inhibitor that is provide in the course of cancer therapy.

Similarly, in an embodiment where an adoptive T-cell transfer therapy is being administered, the initial administration of the pentaaza macrocyclic ring complex may be performed after a predetermined period of time has elapsed since an initial administration of the T-cells being provided as a part of the start of the adoptive T-cell transfer therapy. The predetermined period of time may be, for example, the same time period described for delay between the pentaaza macrocyclic ring complex and immune checkpoint inhibitor above, or different delay in the administration of the pentaaza macrocyclic complex may also be provided. Furthermore, administration of the pentaaza macrocyclic ring complex may "skip" days on which an infusion of cells as a part of the adoptive T-cell transfer therapy is being provided, similarly to the combination with the immune checkpoint inhibitor therapy, as discussed above. Also, in an embodiment where a cancer vaccine is being administered, the initial administration of the pentaaza macrocyclic ring complex may be performed after a predetermined period of time has elapsed since an initial administration of the cancer vaccine. The predetermined period of time may be, for example, the same time period described for delay between the pentaaza macrocyclic ring complex and immune checkpoint inhibitor above, or different delay in the administration of the pentaaza macrocyclic complex may also be provided. Furthermore, administration of the pentaaza macrocyclic ring complex may "skip" days on which a cancer vaccine is being administered to the patient, similarly to the combination with the immune checkpoint inhibitor therapy, as discussed above.

Furthermore, in one embodiment, a treatment regimen may involve administration of multiple immunotherapeutic agents. For example, in one embodiment, the administration of a checkpoint inhibitor and pentaaza macrocyclic ring complex may be further supplemented with the administration of one or more of adoptive T-cell transfer and cancer vaccine, either prior to, concomitantly with, or after administration of one or more of the immune checkpoint inhibitor and pentaaza macrocyclic ring complex. In yet another embodiment, the administration of an adoptive T-cell transfer therapy and pentaaza macrocyclic ring complex may be further supplemented with the administration of one or more of an immune checkpoint inhibitor and cancer vaccine, either prior to, concomitantly with, or after administration of one or more of the adoptive T-cell transfer therapy and pentaaza macrocyclic ring complex. In yet another embodiment, the administration of a cancer vaccine and pentaaza macrocyclic ring complex may be further supplemented with the administration of one or more of adoptive T-cell transfer and immune checkpoint inhibitor, either prior to, concomitantly with, or after administration of one or more of the cancer vaccine and pentaaza macrocyclic ring complex. Furthermore, other dosing schemes other than those specifically mentioned herein may also be provided.

Other Cancer Therapies

In one embodiment, the treatment provided herein can comprise further comprise treatment with another therapy other than those specifically described above, such as for example a radiation therapy, a chemotherapy, or other immunotherapeutic treatment. For example, in one embodiment, one or more of radiation therapy and chemotherapy is administered to the subject prior to, concomitantly with, or after administration of one or more of the immunotherapeutic agent (e.g., immune checkpoint inhibitor, adoptive T-cell transfer, cancer vaccine) and the pentaaza macrocyclic ring complex. Further detailed description of radiation therapies and chemotherapies suitable for the treatment of cancer are provided below.

In one embodiment, one or more of radiation therapy and chemotherapy can be administered concomitantly with administration of one or more of the immunotherapeutic agent and pentaaza macrocyclic ring complex. For example, one or more of the immunotherapeutic agent and pentaaza macrocyclic ring complexes may be administered during a course of radiation therapy and/or chemotherapy, such as in between, before or after, or on the same day as dosing with radiation and/or chemotherapy. In one embodiment, as is further demonstrated in the Examples below, it has been found that administering a pentaaza macrocyclic ring complex such as GC4419 can improve a subject's response to radiation therapy, including when such radiation therapy is combined with administration of an immunotherapy agent, such as the checkpoint inhibitor anti-CTLA4. Without being limited by any theory, it is believed that pentaaza macrocyclic ring complexes such as GC4419 can sensitize cancer cells to radiation to improve treatment therewith.

In yet another embodiment, the combination therapy of the pentaaza macrocyclic ring complex and immunotherapeutic agent (e.g. immune checkpoint inhibitor, adoptive T-cell transfer, cancer vaccine), can be administered in the absence of any other cancer treatment. As demonstrated further in the examples below, it has been unexpectedly discovered that the pentaaza macrocyclic ring complexes are capable of enhancing the response to and/or efficacy of immunotherapeutic agents such as immune checkpoint inhibitors, even when administered without radiation therapy or chemotherapy. Accordingly, in one embodiment, the cancer treatment provided to the subject may consist essentially of the pentaaza macrocyclic ring complex and immunotherapeutic agent, without the administration of a chemotherapeutic agent or radiation exposure (i.e. without administering a radiation dose or dose fraction). For example, the combination of the pentaaza macrocyclic ring complex and immunotherapeutic agent may be administered to a subject that is not receiving radiation therapy, and/or that is not receiving chemotherapy. That is, in one embodiment, the treatment comprises administering the pentaaza macrocyclic ring complex to a subject that is not receiving radiation therapy. In yet another embodiment, the treatment comprises administering the immune checkpoint inhibitor and pentaaza macrocyclic ring complex to a subject that is not receiving radiation therapy. In yet another embodiment, where a course of therapy comprises administration of the pentaaza macrocyclic ring complex and the immune checkpoint inhibitor, they are administered to a subject that does not receive radiation therapy during the course of therapy.

In one embodiment, the subject receiving the combination of pentaaza macrocyclic ring complex and immunotherapeutic agent (e.g. immune checkpoint inhibitor, adoptive T-cell transfer, cancer vaccine), may be one that has not been exposed to radiation (i.e., received a dose or dose fraction of radiation) and/or has not received a dose of chemotherapeutic agent for at least on day, such as at least one week, and even at least one month, and even at least 6 months, and/or that has not ever received such treatment at all before initial treatment with one or more of the pentaaza macrocyclic ring complex and immunotherapeutic agent (e.g., immune checkpoint inhibitor, adoptive T-cell transfer, cancer vaccine). In yet another embodiment, any radiation therapy and/or chemotherapy that is administered to the subject after the combination treatment with the pentaaza macrocyclic ring complex and immunotherapeutic agent (e.g., immune checkpoint inhibitor, adoptive T-cell transfer, cancer vaccine) is delayed by at least one day, such as at least one week, and even at least one month, such as at least 6 months, after a final dose of one or more of the pentaaza macrocyclic ring complex and immunotherapeutic agent provided during the course of the combination therapy treatment. That is, the combination therapy of the pentaaza macrocyclic ring complex and immunotherapeutic agent (e.g. immune checkpoint inhibitor, adoptive T-cell transfer, cancer vaccine) can be administered to a subject that has never before received radiation therapy and/or chemotherapy, or that has received such therapy only in the distant past. Furthermore, the combination therapy of the pentaaza macrocyclic ring complex and immunotherapeutic agent (e.g. immune checkpoint inhibitor, adoptive T-cell transfer, cancer vaccine) can be administered to provide a course of treatment that does not include any exposure to radiation or doses of chemotherapeutic agent. As yet a further embodiment, the combination therapy of the pentaaza macrocyclic ring complex and immunotherapeutic agent (e.g. immune checkpoint inhibitor, adoptive T-cell transfer, cancer vaccine) can be provided to form a course of treatment substantially without performing any radiation therapy or chemotherapy after the course of treatment, or with such radiation or chemotherapeutic treatment being performed only after a significant period of time has elapsed after the course of combination treatment has ended. In one embodiment, the treatment comprises administering one or more of the pentaaza macrocyclic ring complex and immune checkpoint inhibitor to the subject on a day other than a day that the subject is receiving radiation therapy.

Methods of Administration

According to one embodiment, the immunotherapeutic agent (e.g., immune checkpoint inhibitor, adoptive T-cell transfer therapy, cancer vaccine), is administered as a co-therapy or combination therapy with the pentaaza macrocyclic ring complex. Co-therapy or combination therapy according to the methods described herein is intended to embrace administration of each compound in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent, or single or multiple parenteral administrations, or other routes of administration and dosage forms. When administered in combination, therefore, the therapeutic agents (i.e., the pentaaza macrocyclic ring complex and/or the immunotherapeutic agent) can be formulated as separate compositions that are administered at the same time or sequentially at different times, or the therapeutic agents can be given as a single composition. Pharmaceutical compositions and formulations are discussed elsewhere herein. Furthermore, while the immunotherapeutic agent is referred to as including one or more of an immune checkpoint inhibitor, adoptive T-cell transfer therapy, and cancer vaccine, it is noted that all combinations of these are also explicitly included herein. Furthermore, other immunotherapeutic agents such as anti-cancer antibodies, cytokines such as IL-2, and other cancer treating agents, can also be administered as a co-therapy or combination therapy with the pentaaza macrocyclic ring complex and the specific immunotherapeutic agents described herein.

It is not necessary that the pentaaza macrocyclic ring complex and the immunotherapeutic agent (e.g., immune checkpoint inhibitor, adoptive T-cell transfer therapy, cancer vaccine) be administered simultaneously or essentially simultaneously, the agents and compounds may be administered in sequence. The advantage of a simultaneous or essentially simultaneous administration, or sequential administration, is well within the determination of the skilled clinician. For instance, while a pharmaceutical composition or formulation comprising an immunotherapeutic agent (e.g., immune checkpoint inhibitor, adoptive T-cell transfer therapy, cancer vaccine) may be advantageous for administering first in the combination for one particular treatment, prior to administration of the pentaaza macrocyclic ring complex, prior administration of the pentaaza macrocyclic ring complex may be advantageous in another treatment. It is also understood that the instant combination of pentaaza macrocyclic ring complex and the immunotherapeutic agent (e.g., immune checkpoint inhibitor, adoptive T-cell transfer therapy, cancer vaccine) may be used in conjunction with other methods of treating cancer (typically cancerous tumors) including, but not limited to, radiation therapy and surgery, or other chemotherapy. It is further understood that another active agent, such as a cytostatic or quiescent agent, or antiemetic agent, if any, may be administered sequentially or simultaneously with any or all of the other synergistic therapies.

Thus, embodiments of the therapeutic method include wherein a pentaaza macrocyclic ring complex and the immunotherapeutic agent (e.g., immune checkpoint inhibitor, adoptive T-cell transfer therapy, cancer vaccine), and combinations thereof, are administered simultaneously or sequentially. For instance, the present disclosure encompasses a method for the treatment of cancer wherein a pentaaza macrocyclic ring complex and the immunotherapeutic agent (e.g., immune checkpoint inhibitor, adoptive T-cell transfer therapy, cancer vaccine) are administered simultaneously or sequentially. Other active agents can also be administered simultaneously or sequentially with the pentaaza macrocyclic ring complex and the immunotherapeutic agent (e.g., immune checkpoint inhibitor, adoptive T-cell transfer therapy, cancer vaccine).

As noted above, if the pentaaza macrocyclic ring complex and the immunotherapeutic agent (e.g., immune checkpoint inhibitor, adoptive T-cell transfer therapy, cancer vaccine) are not administered simultaneously or essentially simultaneously, then the initial order of administration of the components may be varied.

Thus, for example, the immunotherapeutic agent (e.g., immune checkpoint inhibitor, adoptive T-cell transfer therapy, cancer vaccine) may be administered first, followed by the administration of the pentaaza macrocyclic ring complex; or the pentaaza macrocyclic ring complex may be administered first, followed by the administration of the immunotherapeutic agent. This alternate administration may be repeated during a single treatment protocol. Other sequences of administration to exploit the effects described herein are contemplated, and other sequences of administration of other active agents can also be provided.

In one embodiment, the subject is pre-treated with the immunotherapeutic agent (e.g., immune checkpoint inhibitor, adoptive T-cell transfer therapy, cancer vaccine), followed by administration of the pentaaza macrocyclic ring complex, or vice versa. In accordance with such embodiments, the pentaaza macrocyclic ring complex may be administered at least 1 hour, and even at least 3 days, after administration of the immunotherapeutic agent, or vice versa. For example, in one embodiment, the pentaaza macrocyclic ring complex is administered between 1 hour and 3 days after administration of the immunotherapeutic agent, or vice versa. In another embodiment, for example, the pentaaza macrocyclic ring complex is administered between 1 hour and 1 day after administration of the immunotherapeutic agent, or vice versa. For example, the pentaaza macrocyclic ring complex may be administered within 1 hour, 2 hours, 3 hours, 4 hours, 5 hours, 6 hours, 12 hours, 18 hours, 24 hours, 36 hours, 48 hours, one week, 2 weeks, 3 weeks, 4 weeks, 6 weeks, 8 weeks, 9 weeks, 10 weeks or 12 weeks after administration of the immunotherapeutic agent, or vice versa. In these and other embodiments, the immunotherapeutic agent may be administered in multiple doses leading up to administration of the pentaaza macrocyclic ring complex, or vice versa.

Alternatively, the subject may be pre-treated with the pentaaza macrocyclic ring complex, followed by administration of the immunotherapeutic agent, or vice versa. In accordance with such embodiments, the pentaaza macrocyclic ring complex may be administered within at least 1 plasma half-life of the immunotherapeutic agent, such as within 4 plasma half-lives of the immunotherapeutic agents, or vice versa. For example, the pentaaza macrocyclic ring complex may be administered within 1, 2, or 3 plasma half-lives of the other immunotherapeutic agents, or vice versa.

In other alternative embodiments, the subject may be pre-treated with the immunotherapeutic agent (e.g., immune checkpoint inhibitor, adoptive T-cell transfer therapy, cancer vaccine), followed by administration of the pentaaza macrocyclic ring complex, which is further followed by one or more additional administrations of the immunotherapeutic agent, or vice versa. For example, the subject could be pre-treated with a dose of immunotherapeutic agent, followed by administration of a dose of pentaaza macrocyclic ring complex, which is then followed by the administration of additional (or partial) dose of the same or different immunotherapeutic agent, which may be further followed by another dose of pentaaza macrocyclic ring complex. Further, the subject could be pre-treated with a partial or full dose of pentaaza macrocyclic ring complex, followed by administration of an immunotherapeutic agent, which is then followed by administration of an additional (or partial) dose of pentaaza macrocyclic complex.

As described in further detail below, the combinations of the disclosure may also be co-administered with other well known therapeutic agents that are selected for their particular usefulness against the condition that is being treated. Combinations may alternatively be used sequentially with known pharmaceutically acceptable agent(s) when a multiple combination formulation is inappropriate.

In one embodiment, the pentaaza macrocyclic ring complex and the immunotherapeutic agent (e.g., immune checkpoint inhibitor, adoptive T-cell transfer therapy, cancer vaccine) can generally be administered according to therapeutic protocols that may be known for these agents in the art. For example, the administration of the various components can be varied depending on the disease being treated and the effects of pentaaza macrocyclic ring complex and immunotherapeutic agent on that disease. Also, in accordance with the knowledge of the skilled clinician, the therapeutic protocols (e.g., dosage amounts and times of administration) can be varied in view of the observed effects of the administered therapeutic agents (i.e., pentaaza macrocyclic ring complex, immunotherapeutic agent) on the patient, and in view of the observed responses of the disease to the administered therapeutic agents.

Also, in general, the pentaaza macrocyclic ring complex and the immunotherapeutic agent (e.g., immune checkpoint inhibitor, adoptive T-cell transfer therapy, cancer vaccine) do not have to be administered in the same pharmaceutical composition, and may, because of different physical and chemical characteristics, have to be administered by different routes. For example, the pentaaza macrocyclic ring complex may be administered orally to generate and maintain good blood levels thereof, while the immunotherapeutic agent (e.g., immune checkpoint inhibitor, adoptive T-cell transfer therapy, cancer vaccine) may be administered intravenously or via transfusion, or vice versa. The mode of administration may include, where possible, in the same pharmaceutical composition, or in separate pharmaceutical compositions (e.g., two or three separate compositions). Furthermore, once the initial administration has been made, then based upon the observed effects, the dosage, modes of administration and times of administration can be modified.

The particular choice of pentaaza macrocyclic ring complex and the immunotherapeutic agent (e.g., immune checkpoint inhibitor, adoptive T-cell transfer therapy, cancer vaccine), and other related therapies (such as chemotherapy or radiation), will depend upon the diagnosis of the attending physicians and their judgment of the condition of the patient and the appropriate treatment protocol.

Thus, in accordance with experience and knowledge, the practicing physician can modify each protocol for the administration of a component (pentaaza macrocyclic ring complex and the immunotherapeutic agent (e.g., immune checkpoint inhibitor, adoptive T-cell transfer therapy, cancer vaccine) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The products of which the combination are composed may be administered simultaneously, separately or spaced out over a period of time so as to obtain the maximum efficacy of the combination; it being possible for each administration to vary in its duration from a rapid administration to a relatively continuous perfusion of either component (in separate formulations or in a single formulation). As a result, for the purposes of the present disclosure, the combinations are not exclusively limited to those which are obtained by physical association of the constituents, but also to those which permit a separate administration, which can be simultaneous or spaced out over a period of time.

Accordingly, administration of the components described herein can occur as a single event or over a time course of treatment. For example, the pentaaza macrocyclic ring complex and the immunotherapeutic agent (e.g., immune checkpoint inhibitor, adoptive T-cell transfer therapy, cancer vaccine) can be administered (simultaneously or in sequence) hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compounds and agents can be administered hourly, daily, weekly, bi-weekly, or monthly, for a period of several weeks, months, years, or over the lifetime of the patient as a prophylactic measure.

The dose or amount of pharmaceutical compositions including the pentaaza macrocyclic ring complex and the immunotherapeutic agent (e.g., immune checkpoint inhibitor, adoptive T-cell transfer therapy, cancer vaccine) administered to the patient should be an effective amount for the intended purpose, i.e., treatment or prophylaxis of one or more of the diseases, pathological disorders, and medical conditions discussed herein, particularly cancer. Generally speaking, the effective amount of the composition administered can vary according to a variety of factors such as, for example, the age, weight, sex, diet, route of administration, and the medical condition of the patient in need of the treatment. Specifically preferred doses are discussed more fully herein. It will be understood, however, that the total daily usage of the compositions described herein will be decided by the attending physician or veterinarian within the scope of sound medical judgment.

As noted above, the combinations can be co-administered (via a co-formulated dosage form or in separate dosage forms administered at about the same time). The combinations can also be administered separately, at different times, with each agent in a separate unit dosage form. Numerous approaches for administering the immunotherapeutic agent (e.g., immune checkpoint inhibitor, adoptive T-cell transfer therapy, cancer vaccine) and pentaaza macrocyclic ring complex can be readily adapted for use in the present disclosure. The pharmaceutical compositions may be delivered orally, e.g., in a tablet or capsule unit dosage form, or parenterally, e.g., in an injectable unit dosage form, or by some other route. For systemic administration, for example, the drugs can be administered by, for example, intravenous infusion (continuous or bolus). The compositions can be used for any therapeutic or prophylactic treatment where the patient benefits from treatment with the combination.

The specific therapeutically effective dose level for any particular patient will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

In one embodiment, suitable or preferred doses for each of the components are employed in the methods or included in the compositions described herein. Preferred dosages for the pentaaza macrocyclic ring complex, for instance, may be within the range of 10 to 500 mg per patient per day. However, the dosage may vary depending on the dosing schedule, which can be adjusted as necessary to achieve the desired therapeutic effect. It should be noted that the ranges of effective doses provided herein are not intended to limit the disclosure and represent exemplary dose ranges. The most preferred dosage will be tailored to the individual subject, taking into account, among other things, the particular combinations employed, and the patient's age, sex, weight, physical condition, diet, etc., as is understood and determinable by one of ordinary skill in the art without undue experimentation.

Treatment of cancer, or cancer therapies, described herein includes achieving a therapeutic benefit, however the therapy may also be administered to achieve a prophylactic benefit. Therapeutic benefits generally refer to at least a partial eradication or amelioration of the underlying disorder being treated. For example, in a cancer patient, therapeutic benefit includes (partial or complete) eradication or amelioration of the underlying cancer. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk of developing cancer, or to a patient reporting one or more of the physiological symptoms of such conditions, even though a diagnosis of the condition may not have been made.

Cancer Treatment Methods

In general, any subject having, or suspected of having, a cancer or other proliferative disorder may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In one embodiment of the disclosure, a method is provided for the treatment of cancerous tumors, particularly solid tumors. Advantageously, the methods described herein may reduce the development of tumors, reduce tumor burden, or produce tumor regression in a mammalian host. Cancer patients and individuals desiring cancer prophylaxis can be treated with the combinations described herein.

Cancer and tumors generally refer to or describe the physiological condition in mammals that is typically characterized by unregulated cell growth. By means of the pharmaceutical combinations, co-formulations, and combination therapies of the present disclosure, various tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

In one embodiment, the tumor or cancer is chosen from adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Thus, for example, the present disclosure provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, particular leukemias that can be treated with the combinations and methods described herein include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas can also be treated with the combinations and methods described herein. Lymphomas are generally neoplastic transformations of cells that reside primarily in lymphoid tissue. Lymphomas are tumors of the immune system and generally are present as both T cell- and as B cell-associated disease. Among lymphomas, there are two major distinct groups: non-Hodgkin's lymphoma (NHL) and Hodgkin's disease. Bone marrow, lymph nodes, spleen and circulating cells, among others, may be involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then re-infused in order to repopulate the patient's hematopoietic system.

Other hematological malignancies that can be treated with the combinations and methods described herein include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

In one embodiment, the methods and pharmaceutical compositions described herein are used to treat a cancer that is any of breast cancer, melanoma, oral squamous cell carcinoma, lung cancer including non-small cell lung cancer, renal cell carcinoma, colorectal cancer, prostate cancer, brain cancer, spindle cell carcinoma, urothelial cancer, bladder cancer, colorectal cancer, head and neck cancers such as squamous cell carcinoma, and pancreatic cancer. In yet another embodiment, the methods and pharmaceutical compositions described herein are used to treat a cancer that is any of head and neck cancer and lung cancer.

Pharmaceutical Formulations

Another aspect of the present disclosure relates to the pharmaceutical compositions comprising the combinations described herein, together with a pharmaceutically acceptable excipient. The pharmaceutical compositions include the pentaaza macrocyclic ring complex (e.g., those corresponding to Formula (I)), and at least one immunotherapeutic agent (e.g., immune checkpoint inhibitor, adoptive T-cell transfer therapy, cancer vaccine), and combinations thereof, as discussed above, typically formulated as a pharmaceutical dosage form, optionally in combination with a pharmaceutically acceptable carrier, additive or excipient. In one embodiment, for example, the pharmaceutical composition comprises a pentaaza macrocyclic ring complex, the immunotherapeutic agent (e.g., immune checkpoint inhibitor, adoptive T-cell transfer therapy, cancer vaccine) and a pharmaceutically acceptable excipient. Pharmaceutical compositions according to the present disclosure may be used in the treatment of cancer.

The pharmaceutical compositions described herein are products that result from the mixing or combining of more than one active ingredient and includes both fixed and non-fixed combinations of the active ingredients. Fixed combinations are those in which the active ingredients, e.g., a pentaaza macrocyclic ring complex and an immunotherapeutic agent (e.g., immune checkpoint inhibitor, adoptive T-cell transfer therapy, cancer vaccine), are administered to a patient simultaneously in the form of a single entity or dosage. Other active agents may also be administered as a part of the single entity or dosage, or may be separately administered Non-fixed combinations are those in which the active ingredients, e.g., a pentaaza macrocyclic ring complex and the immunotherapeutic agent (e.g., immune checkpoint inhibitor, adoptive T-cell transfer therapy, cancer vaccine), are administered to a patient as separate entities either simultaneously, concurrently or sequentially with no specific intervening time limits, wherein such administration provides effective levels of the compounds in the body of the patient. The latter also applies to cocktail therapy, e.g., the administration of three or more active ingredients.

The above-described pentaaza macrocyclic ring complex and the immunotherapeutic agent (e.g., immune checkpoint inhibitor, adoptive T-cell transfer therapy, cancer vaccine) may be dispersed in a pharmaceutically acceptable carrier prior to administration to the mammal; i.e., the components described herein are preferably co-formulated. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the compositions of the present disclosure are well known to those of ordinary skill in the art and are selected based upon a number of factors: the particular compound(s) and agent(s) used, and its/their concentration, stability and intended bioavailability; the subject, its age, size and general condition; and the route of administration. Suitable non-aqueous, pharmaceutically-acceptable polar solvents include, but are not limited to, alcohols (e.g., a-glycerol formal, 6-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(6-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyester, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate®20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $0_4$ to $0_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, di methylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., J. Mol. Biol, 23: 238-252 (1965) and Szoka et al., Proc. Natl Acad. Sci 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

Formulations containing the pentaaza macrocyclic ring complex and the immunotherapeutic agent (e.g., immune checkpoint inhibitor, adoptive T-cell transfer therapy, cancer vaccine) may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products employ the pentaaza macrocyclic ring complex and the immunotherapeutic agent (e.g., immune checkpoint inhibitor, adoptive T-cell transfer therapy, cancer vaccine) within accepted dosage ranges.

In one embodiment, a formulation is provided that contains the immunotherapeutic agent (e.g., immune checkpoint inhibitor, adoptive T-cell transfer therapy, cancer vaccine) as a part of liquid dosage form, such as a sterile liquid dosage form suitable for injection. For example, the liquid form containing the immunotherapeutic agent (e.g., immune checkpoint inhibitor, adoptive T-cell transfer therapy, cancer vaccine) in combination with one or more further ingredients, such as edetate disodium (EDTA). In one embodiment, the liquid form can comprise EDTA in an amount suitable to act as a preservative and/or metal-chelating agent, such as an amount of about 0.025%. The liquid form can further comprise water, and may also comprise a pH adjuster, such as sodium bicarbonate, for pH adjustment in the range of pH 5.5 to 7.0. In one embodiment, the pentaaza macrocyclic ring complex can also be provided as a part of a sterile liquid dosage form suitable for injection, either in the same liquid dosage form with the immunotherapeutic agent (e.g., immune checkpoint inhibitor, adoptive T-cell transfer therapy, cancer vaccine) or as a separate dosage form.

Formulations for certain pentaaza macrocyclic ring complexes are also described in, for example, in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

It is contemplated that co-formulations of the pentaaza macrocyclic ring complex and the immunotherapeutic agent (e.g., immune checkpoint inhibitor, adoptive T-cell transfer therapy, cancer vaccine) may employ conventional formulation techniques for these components individually, or alternative formulation routes, subject to compatibility and efficacy of the various components, in combination.

The above-described pharmaceutical compositions including the pentaaza macrocyclic compound and the immunotherapeutic agent (e.g., immune checkpoint inhibitor, adoptive T-cell transfer therapy, cancer vaccine) may additionally include one or more additional pharmaceutically active components. Suitable pharmaceutically active agents that may be included in the compositions of the present invention include, for instance, antiemetics, anesthetics, antihypertensives, antianxiety agents, anticlotting agents, anticonvulsants, blood glucose-lowering agents, decongestants, antihistamines, antitussives, antineoplastics, beta blockers, anti-inflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents. The individual components of such combinations may be administered either sequentially or simultaneously in separate or combined pharmaceutical formulations.

In yet another embodiment, a kit may be provided that includes both the pentaaza macrocyclic ring complex and the immunotherapeutic agent (e.g., immune checkpoint inhibitor, adoptive T-cell transfer therapy, cancer vaccine), for treatment of a condition such as cancer or a viral infection. For example, the kit may comprise a first vessel or container having therein a formulation comprising the pentaaza macrocyclic ring complex, such as an oral or injectable formulation of the pentaaza macrocyclic ring complex, and a second vessel or container having therein a formulation comprising the immunotherapeutic agent, such as an injectable formulation of an immune checkpoint inhibitor or other immunotherapeutic agent. The kit may further comprise a label or other instructions for administration of the active agents, recommended dosage amounts, durations and administration regimens, warnings, listing of possible drug-drug interactions, and other relevant instructions.

Combination Treatment with Cancer Therapy

In one embodiment, the pentaaza macrocyclic ring complex and the immunotherapeutic agent (e.g., immune checkpoint inhibitor, adoptive T-cell transfer therapy, cancer vaccine) can be administered in combination with another cancer therapy, to provide therapeutic treatment. For example, the pentaaza macrocyclic ring complex and the immunotherapeutic agent (e.g., immune checkpoint inhibitor, adoptive T-cell transfer therapy, cancer vaccine) may be administered as a part of at least one of a chemotherapy treatment and radiation therapy.

In general, the temporal aspects of the administration of the pentaaza macrocyclic ring complex and the immunotherapeutic agent (e.g., immune checkpoint inhibitor, adoptive T-cell transfer therapy, cancer vaccine) may depend for example, on the particular compound, radiation therapy, or chemotherapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the compounds may be administered in various embodiments before, during, and/or after the administration of the cancer therapy (e.g., before, during or after exposure to and/or before, during or after a dose of chemotherapy, or before, during or after a course of radiation therapy or chemotherapy comprising multiple exposures and/or doses). By way of another example, the compounds may be administered in various embodiments before, during, and/or after an exposure to radiation.

If desired, the effective dose can be divided into multiple doses for purposes of administration; consequently, single dose compositions may contain such amounts or submultiples thereof to make up the dose.

In one embodiment, for example, the pentaaza macrocyclic ring complex and the immunotherapeutic agent (e.g., immune checkpoint inhibitor, adoptive T-cell transfer therapy, cancer vaccine) are administered to the patient prior to or simultaneous with the cancer therapy corresponding to at least one of radiation therapy and chemotherapy, such as prior to or simultaneous with a dose or dose fraction of such treatment, or prior to or simultaneous with a course of such treatment comprising multiple doses. In another embodiment, for example, the pentaaza macrocyclic ring complex and the immunotherapeutic agent (e.g., immune checkpoint inhibitor, adoptive T-cell transfer therapy, cancer vaccine) are administered to the patient prior to, but not after, the cancer therapy, such as before but nor after a cancer therapy dose or dose fraction or prior to but not after a course of cancer therapy comprising multiple doses or dose fractions. In yet another embodiment, the pentaaza macrocyclic ring complex and the immunotherapeutic agent (e.g., immune checkpoint inhibitor, adoptive T-cell transfer therapy, cancer vaccine) are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to an initial dose or dose fraction of cancer therapy corresponding to at least one of radiation therapy and chemotherapy. In still other embodiments, for example, the pentaaza macrocyclic ring complex and the immunotherapeutic agent (e.g., immune checkpoint inhibitor, adoptive T-cell transfer therapy, cancer vaccine) are administered to the patient after a dose or dose fraction of cancer therapy; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after a single dose or dose fraction and/or final dose or dose fraction in a course of cancer treatment corresponding to one or more of radiation therapy and chemotherapy.

In another embodiment, for example, the pentaaza macrocyclic ring complex and the immunotherapeutic agent (e.g., immune checkpoint inhibitor, adoptive T-cell transfer therapy, cancer vaccine) are administered to the patient prior to or simultaneous with the radiation exposure. In another embodiment, for example, the components are administered to the patient prior to, but not after, the radiation exposure. In yet another embodiment, one or more of the pentaaza macrocyclic ring complex and the immunotherapeutic agent (e.g., immune checkpoint inhibitor, adoptive T-cell transfer therapy, cancer vaccine) are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure, such as an initial radiation exposure in a course of radiation treatment, or prior to another dose or dose fraction of radiation that is one of the doses or dose fractions of radiation in the course of treatment. In still other embodiments, for example, pentaaza macrocyclic ring complex and the immunotherapeutic agent (e.g., immune checkpoint inhibitor, adoptive T-cell transfer therapy, cancer vaccine) are administered to the patient after the radiation exposure; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure, which may be a dose or dose fraction of radiation in a multi-dose course of radiation therapy, or may be the single or final dose or dose fraction of radiation in the radiation therapy.

In one embodiment, the pentaaza macrocyclic ring complex and the immunotherapeutic agent (e.g., immune checkpoint inhibitor, adoptive T-cell transfer therapy, cancer vaccine) are administered as a part of a course of therapy that includes the radiation therapy. In radiation therapy, a patient receives a dose or dose fraction of ionizing radiation to kill or control the growth of cancerous cells. The dose or dose fraction of radiation may be directed at a specific part of the body, and the beam of radiation may also be shaped according to a predetermined treatment regimen, to reduce deleterious effects on parts of the body not afflicted with cancer. A typical course of radiation therapy may include one or a plurality of doses or dose fractions of radiation, which can be administered over the course of days, weeks and even months. A total "dose" of radiation given during a course of radiation therapy typically refers to the amount of radiation a patient receives during the entire course of radiation therapy, which doses may be administered as dose "fractions" corresponding to multiple radiation exposures in the case where the total dose is administered over several sessions, with the sum of the fractions administered corresponding to the overall dose. As is discussed in more detail in the Examples section below, the administration of pentaaza macrocyclic ring complex with the immunotherapeutic agent (e.g., immune checkpoint inhibitor, adoptive T-cell transfer therapy, cancer vaccine) can provide benefits treatment of cancer, thereby improving the efficacy of radiation treatment provided in combination with the immunotherapeutic agent.

In one embodiment, at least one of the pentaaza macrocyclic ring complex and the immunotherapeutic agent (e.g., immune checkpoint inhibitor, adoptive T-cell transfer therapy, cancer vaccine) are administered within a predetermined time period before or after a radiation exposure, such as a before or after a radiation dose or dose fraction. For example, the pentaaza macrocyclic ring complex and the immunotherapeutic agent (e.g., immune checkpoint inhibitor, adoptive T-cell transfer therapy, cancer vaccine) may be administered within 1 week, 48 hours, 24 hours, 12 hours, 6, hours, 2 hours, 1 hour or even within 30 minutes of the patient receiving the radiation exposure, such as the dose or dose fraction (either before or after the radiation exposure corresponding to the radiation dose or dose fraction). Other durations between the radiation exposure and administration of the compound that result in the enhanced the killing of cancer cells may also be suitable. In one embodiment, one or more of the pentaaza macrocyclic ring complex and the immunotherapeutic agent (e.g., immune checkpoint inhibitor, adoptive T-cell transfer therapy, cancer vaccine) may be administered before the radiation exposure, and the remaining one or more of the pentaaza macrocyclic ring complex and the immunotherapeutic agent (e.g., immune checkpoint inhibitor, adoptive T-cell transfer therapy, cancer vaccine) can be administered after the radiation exposure. One or more of the pentaaza macrocyclic ring complex and the immunotherapeutic agent (e.g., immune checkpoint inhibitor, adoptive T-cell transfer therapy, cancer vaccine) may also be administered both before and after administration of a radiation exposure.

In one embodiment, a course of radiation therapy includes a plurality of radiation doses or dose fractions given over a predetermined period of time, such as over the course of hours, weeks, days and even months, with the plural doses or dose fractions being either of the same magnitude or varying. That is, a course of radiation therapy can comprise the administration of a series of multiple doses or dose fractions of radiation. In one embodiment, pentaaza macrocyclic ring complex and the immunotherapeutic agent (e.g., immune checkpoint inhibitor, adoptive T-cell transfer therapy, cancer vaccine) can be administered before one or more radiation doses or dose fractions in the series, such as before each radiation dose or dose fraction, or before some number of the radiation doses or dose fractions. Furthermore, the administration of the pentaaza macrocyclic ring complex and the immunotherapeutic agent (e.g., immune checkpoint inhibitor, adoptive T-cell transfer therapy, cancer vaccine) during the course of radiation therapy can be selected to enhance the cancer treating effects of the radiation therapy, such as by sensitizing cancer cells to the radiation therapy. In one embodiment, the pentaaza macrocyclic ring complex and the immunotherapeutic agent (e.g., immune checkpoint inhibitor, adoptive T-cell transfer therapy, cancer vaccine) are administered within a predetermined duration before or after of each dose or dose fraction, such as the predetermined duration discussed above. In another embodiment, the pentaaza macrocyclic ring complex and the immunotherapeutic agent (e.g., immune checkpoint inhibitor, adoptive T-cell transfer therapy, cancer vaccine) are administered within a predetermined duration of time before or after only select doses or dose fractions. In yet another embodiment, at least one of the pentaaza macrocyclic ring complex and the immunotherapeutic agent (e.g., immune checkpoint inhibitor, adoptive T-cell transfer therapy, cancer vaccine) is administered within a predetermined duration of time before the doses, while another of the pentaaza macrocyclic ring complex and the immunotherapeutic agent (e.g., immune checkpoint inhibitor, adoptive T-cell transfer therapy, cancer vaccine) is administered within a predetermined duration of time after the doses or dose fractions. In a further embodiment, at least one of the pentaaza macrocyclic ring complex and the immunotherapeutic agent (e.g., immune checkpoint inhibitor, adoptive T-cell transfer therapy, cancer vaccine) is administered only within the predetermined duration before or after select doses or dose fractions, while another of the pentaaza macrocyclic ring complex and the immunotherapeutic agent (e.g., immune checkpoint inhibitor, adoptive T-cell transfer therapy, cancer vaccine) is administered only within the predetermined duration before or after doses or dose fractions other than the select doses or dose fractions.

A suitable overall dose to provide during a course of therapy can be determined according to the type of treatment to be provided, the physical characteristics of the patient and other factors, and the dose fractions that are to be provided can be similarly determined. In one embodiment, a dose fraction of radiation that is administered to a patient may be at least 1.8 Gy, such as at least 2 Gy, and even at least 3 Gy, such as at least 5 Gy, and even at least 6 Gy. In yet another embodiment, a dose fraction of radiation that is administered to a patient may be at least 10 Gy, such as at least 12 Gy, and even at least 15 Gy, such as at least 18 Gy, and even at least 20 Gy, such as at least 24 Gy. In general, a dose fraction of radiation administered to a patient will not exceed 54 Gy. In some embodiments, the dose fraction of radiation administered to a patient may even be less than 10 Gy, and even less than 8 Gy, such as less than 5 Gy, or less than 3 Gy, including less than 2.5 Gy, less than 2 Gy, or about 1.8 Gy. Furthermore, it should be noted that, in one embodiment, a dose fraction delivered to a subject may refer to an amount delivered to a specific target region of a subject, such as a target region of a tumor, whereas other regions of the tumor or surrounding tissue may be exposed to more or less radiation than that specified by the nominal dose fraction amount.

For example, in one embodiment, the overall dose of radiation provided during the course of therapy may be provided via a hypofractionation radiotherapy scheme, which typically involves providing relatively high dose fractions administered over relatively fewer sessions, as compared to lower dose fraction schemes. Examples of such hypofractionation radiotherapy methods can include, but are not limited to, stereotactic radiosurgery (SRS), which typically refers to a single-fraction treatment directed to targets such as intracranial and spinal targets, as well as stereotactic body radiation therapy (SBRT), which typically refers to multifractional treatment of targets such as intracranial and spinal targets, and also extracranial targets such as lung, liver, head and neck, pancreas and prostate. As an example, in one embodiment of a hypofractionation radiotherapy scheme, the overall dose of radiation provided during the course of therapy may be divided into less than 10 fractions, such as less than 8 fractions, less than 6 fractions, less than 5 fractions, less than 4 fractions, less than 3 fractions, less than 2 fractions and may even be provided in just one administration (single fraction). For example, in one embodiment, the overall dose of radiation provided during the course of therapy may be divided into from 1 to 10 fractions, such as from 1 to 6 fractions, and even from 1 to 5 fractions, such as from 2 to 5 fractions or even 2 to 4 fractions. As yet another example, the hypofractionation radiotherapy scheme can comprise dividing the overall dose of radiation provided during the course of therapy into dose fractions that are at least 10% ($\frac{1}{10}$) of the overall dose provided during therapy, such as at least 12.5% ($\frac{1}{8}$) of the overall dose, at least 16% (~$\frac{1}{6}$) of the overall dose, at least 20% ($\frac{1}{5}$) of the overall dose, at least 25% ($\frac{1}{4}$) of the overall dose, at least 30% ($\frac{1}{3}$) of the overall dose, at least 50% of the overall dose, and/or at least 100% of the overall dose may be provided in a single administration (single fraction). For example, in one embodiment, the overall dose of radiation provided during the course of therapy may be divided into fractions that provide from 10% to 100% of the overall dose in each fraction, such as from 16% to 100% of the overall dose, and even from 20% to 100% of the overall dose, such as from 20% to 50% of the overall dose or even from 25% to 50% of the overall dose. For example a dose fraction size may be at least 5 Gy, such as at least 6 Gy, at least 8 Gy, at least 10 Gy, at least 12 Gy, and even at least 15 Gy, such as at least 18 Gy, and even at least 20 Gy, such as at least 24 Gy, and typically do not exceed 54 Gy, such as less than 40 Gy and even less than 30 Gy. In one embodiment, dose fraction sizes may be in the range of from 5 Gy to 30 Gy, such as from 6 Gy to 28 Gy, and even from 8 Gy to 25 Gy. Furthermore, in one embodiment, the dose fractions may be administered no more than three times per day, and even no more than twice per day, such as no more than once per day, on consecutive or non-consecutive days and/or some combination thereof, and may be administered over a period of a few days and up to a few weeks, such as over a period of 1 to 15 days, 1 to 12 days, 1 to 10 days, 1 to 5 days, and even 1 to 3 days. Typically, the dose fractions making up the overall course of therapy will be administered in no more than 20 days, no more than 15 days, no more than 10 days, no more than 5 days, and even no more than 3 days.

As yet another example, in one embodiment, the overall dose of radiation provided during the course of therapy may be provided via a radiotherapy scheme that provides relatively lower dose fractions administered over relatively more sessions, as compared to, e.g., hypofractionation schemes. Examples of such lower dose fraction radiotherapy methods can include, but are not limited to, intensity-modulated radiation therapy (IMRT) and image guided radiation therapy (IGRT), which typically involve three-dimensional conformal therapy (3D-CRT) to match the administered radiation to a target volume. As an example, in one embodiment of such a radiotherapy scheme, the overall dose of radiation provided during the course of therapy may be divided into at least 15 fractions, such as at least 18 fractions, at least 20 fractions, at least 22 fractions, at least 25 fractions, at least 28 fractions, at least 30 fractions, at least 32 fractions, at least 35 fractions, and even at least 38 fractions, although the total number of fractions will typically be less than 50, such as less than 45, and even less than 42. For example, in one embodiment, the overall dose of radiation provided during the course of therapy may be divided into from 15 to 38 fractions, such as from 20 to 38 fractions, and even from 20 to 35 fractions, such as from 25 to 35 fractions. As yet another example, the radiotherapy scheme can comprise dividing the overall dose of radiation provided during the course of therapy into dose fractions that are no more than 7% ($\frac{1}{15}$) of the overall dose provided during therapy, such as no more than 6% ($\frac{1}{18}$) of the overall dose, no more than 5% ($\frac{1}{20}$) of the overall dose, no more than 4.5% ($\frac{1}{22}$) of the overall dose, no more than 4% ($\frac{1}{25}$) of the overall dose, no more than 3.6% ($\frac{1}{28}$) of the overall dose, no more than 3.3% (1/30) of the overall dose, no more than 3.1% (1/32) of the overall dose, no more than 2.8% of the overall dose (1/35), and even no more than 2.6% (1/38) of the overall dose. For example, in one embodiment, the overall dose of radiation provided during the course of therapy may be divided into fractions that provide from 2.5% to 8% of the overall dose in each fraction, such as from 2.8% to 5% of the overall dose, and even from 2.8% to 4% of the overall dose. For example a dose fraction size may be less than 5 Gy, such as less than 4 Gy, less than 3.5 Gy, less than 3 Gy, less than 2.8 Gy, and even less than 2.5 Gy, such as less than 2.3 Gy, and even less than 2 Gy, such as less than 1.8 Gy, and typically is at least 0.5 Gy, such as at least 1 Gy and even at least 1.5 Gy. In one embodiment, dose fraction sizes may be in the range of from 1.5 Gy to 4.5 Gy, such as from 1.8 Gy to 3 Gy, and even from 2 Gy to 2.5 Gy. Furthermore, in one embodiment, the dose fractions may be administered no more than three times per day, and even no more than twice per day, such as no more than once per day, on consecutive or non-consecutive days, and/or a combination thereof (e.g., on consecutive weekdays), and in some embodiments may be administered over a period of a few days to a few weeks and even a few months, such as over a period of up to 3 weeks, up to 5 weeks, up to 6 weeks, up to 8 weeks and even up to 10 weeks, such as in a range of from 3 weeks to 10 weeks, or even in a range of from 5 weeks to 8 weeks. For example, the dose fractions making up the overall course of therapy can be administered in no more than 12 weeks, such as no more than 10 weeks and even no more than 8 weeks.

In yet another embodiment, the overall dose of radiation provided by the radiation scheme, whether in a relatively high dose fraction scheme or relatively low dose fraction scheme such as those described above, or other scheme, is selected to provide suitable treatment of the cancer. The overall dose may also be provided according to the specific dose fractionation scheme being administered, along with other factors. For example, in certain embodiments, a relatively larger overall dose may be administered as relatively smaller individual dose fractions. In one embodiment, the overall dose provided over the course of the therapy (i.e., the sum of the administered dose fractions), is at least 50 Gy, such as at least 55 Gy, at least 58 Gy, at least 60 Gy, at least 65 Gy, at least 68 Gy, at least 70 Gy, at least 72 Gy, and even at least 75 Gy. In certain embodiments, the overall dose does not exceed 80 Gy, such as not exceeding 78 Gy and even not exceeding 75 Gy. For example, the overall dose may be in a range of from 50 Gy to 75 Gy, such as from 55 Gy to 75 Gy, and even from 60 Gy to 70 Gy.

In yet another embodiment, the pentaaza macrocyclic ring complex and the immunotherapeutic agent (e.g., immune checkpoint inhibitor, adoptive T-cell transfer therapy, cancer vaccine) are administered as a part of a course of therapy that includes chemotherapy. In chemotherapy, chemotherapeutic agents are administered to a patient to kill or control the growth of cancerous cells. A typical course of chemotherapy may include one or a plurality of doses of one or more chemotherapeutic agents, which can be administered over the course of days, weeks and even months. Chemotherapeutic agents can include at least one of: alkylating antineoplastic agents such as nitrogen mustards (e.g. cyclophosphamide, chlorambucil), nitrosoureas (e.g. n-nitroso-n-methylurea, carmustine, semustine), tetrazines (e.g. dacarbazine, mitozolimide), aziridines (e.g. thiotepa, mytomycin), platinum-based antineoplastic agents (platinates) (e.g. cisplatin, carboplatin, oxaliplatin, neoplatin, platamin); anti-metabolites such as antifolates (e.g. methotrexate and pemetrexed), fluoropyrimidines (e.g., fluorouracil, capecitabine), anthracyclines (e.g. doxorubicin, daunorubicin, epirubicin), deoxynucleoside analogs (e.g. cytarabine, gemcitabine, decitabine) and thiopurines (e.g., thioguanine, mercaptopurine); anti microtubule agents such as taxanes (e.g. paclitaxel, docetaxel); topoisomerase inhibitors (e.g. etoposide, doxorubicin, mitoxantrone, teniposide); and antitumor antibiotics (e.g. bleomycin, mitomycin). For example, the chemotherapeutic agent may be selected from the group consisting of all-trans retinoic acid, arsenic trioxide, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine. The administration of many of the chemotherapeutic agents is described in the "Physicians' Desk Reference" (PDR), e.g., 1996 edition (Medical Economics Company, Montvale, N.J. 07645-1742, USA).

In one embodiment, the pentaaza macrocyclic ring complex and the immunotherapeutic agent (e.g., immune checkpoint inhibitor, adoptive T-cell transfer therapy, cancer vaccine) are administered as a part of a course of therapy that includes a chemotherapeutic agent selected from the group consisting of cisplatin, doxorubicin, bleomycin, and paclitaxel. Without being limited to any particular theory, it is believed that cisplatin, doxorubicin, bleomycin, and paclitaxel may contribute to the generation of superoxide radicals in cells, thereby leading when combined with a manganese pentaaza macrocyclic ring complex to increased oxidative stress and cytotoxicity of the cancer cells. Furthermore, in one embodiment, the chemotherapeutic agent may be selected from the group consisting of a platinum-based antineoplastic agents, a taxane, an anticancer antibiotic, and an anthracycline, which categories of chemotherapeutic agents, without being limited to any particular theory or mechanism, may also be effective in providing chemotherapeutic activity at least in part due to generation of superoxide radicals in cells. Other chemotherapeutic agents that may increase superoxide levels can include arsenic trioxide and 5-FU, which agents can also be used in the methods and compositions described herein. (Alexandre et al., Cancer Res. 67: (8), 3512-3517 (2007); Yen et al., J. Clin. Invest. 98 (5), 1253-1260 (1996); Masuda et al., Cancer Chemother. Pharmacol. 47(2), 155-160 (2001)).

According to yet another embodiment, a chemotherapeutic agent can include at least one of an antimetabolite anti-cancer agents and antimitotic anti-cancer agents, and combinations thereof, which may include some of the agents described above and well as other agents described further herein. Various antimetabolite and antimitotic agents may be employed in the methods and compositions described herein.

Antimetabolic agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one embodiment, therefore, the antimetabolite agent is a nucleotide or a nucleotide analog. In certain embodiments, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite agents for use in the present disclosure may be generally classified according to the metabolic process they affect, and can include, but are not limited to, analogues and derivatives of folic acid, pyrimidines, purines, and cytidine. Thus, in one embodiment, the antimetabolite agent(s) is selected from the group consisting of cytidine analogs, folic acid analogs, purine analogs, pyrimidine analogs, and combinations thereof.

In one particular embodiment, for example, the antimetabolite agent is a cytidine analog. According to this embodiment, for example, the cytidine analog may be selected from the group consisting of cytarabine (cytosine arabinoside), azacitidine (5-azacytidine), and salts, analogs, and derivatives thereof.

In another particular embodiment, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain embodiments, for example, the folic acid analog may be selected from the group consisting of denopterin, methotrexate (amethopterin), pemetrexed, pteropterin, raltitrexed, trimetrexate, and salts, analogs, and derivatives thereof.

In another particular embodiment, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain embodiments, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-aminofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular embodiment, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain embodiments, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidine-2'-ene, 3'-deoxy-3'-deoxythymidine-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one embodiment, the pyrimidine analog is other than 5-fluorouracil. In another embodiment, the pyrimidine analog is gemcitabine or a salt thereof.

In certain embodiments, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other embodiments, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular embodiment, the antimetabolite agent is other than 5-fluorouracil. In a particularly preferred embodiment, the antimetabolite agent is gemcitabine or a salt or thereof (e.g., gemcitabine HCl (Gemzar®)).

Other antimetabolite agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

In one embodiment, the chemotherapeutic agent comprises an antimitotic agent that is a microtubule inhibitor or a mictrotubule stabilizer. In general, microtubule stabilizers, such as taxanes (some of which are also described above) and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the vinca alkaloids, which prevent microtubule assembly, the microtubule stabilizers, such as taxanes, decrease the lag time and dramatically shift the dynamic equilibrium between tubulin dimers and microtubule polymers towards polymerization. In one embodiment, therefore, the microtubule stabilizer is a taxane or an epothilone. In another embodiment, the microtubule inhibitor is a vinca alkaloid.

One element of the therapy described herein may include the use of a taxane or derivative or analog thereof, some of which have also been discussed above. In one embodiment, the taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, *Taxus brevifolia*, and which have activity against certain tumors, particularly breast and ovarian tumors. In one embodiment, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Atta-ur-Rabman, P. W. le Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, Mo.

Alternatively, the antimitotic agent can be a microtubule inhibitor; in one preferred embodiment, the microtubule inhibitor is a vinca alkaloid. In general, the vinca alkaloids are mitotic spindle poisons. The vinca alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain embodiments, for example, the vinca alkaloid is selected from the group consisting of vinblastine, vincristine, vindesine, vinorelbine, and salts, analogs, and derivatives thereof.

The antimitotic agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain embodiments, the antimitotic anti-cancer agent is selected from the group consisting of taxanes, epothilones, vinca alkaloids, and salts and combinations thereof. Thus, for example, in one embodiment the antimitotic agent is a taxane. More preferably in this embodiment the antimitotic agent is paclitaxel or docetaxel, still more preferably paclitaxel. In another embodiment, the antimitotic agent is an epothilone (e.g., an epothilone B analog). In another embodiment, the antimitotic agent is a vinca alkaloid.

In one embodiment, at least one of the pentaaza macrocyclic ring complex and the immunotherapeutic agent (e.g., immune checkpoint inhibitor, adoptive T-cell transfer therapy, cancer vaccine) are administered within a predetermined time period before or after a dose of a chemotherapeutic agent is administered. For example, the pentaaza macrocyclic ring complex and the immunotherapeutic agent (e.g., immune checkpoint inhibitor, adoptive T-cell transfer therapy, cancer vaccine) may be administered within 1 week, 48 hours, 24 hours, 12 hours, 6, hours, 2 hours, 1 hour or even within 30 minutes of the patient receiving the dose of chemotherapeutic agent (either before or after the dose of chemotherapeutic agent). Other durations between the chemotherapeutic agent dose and administration of the components that result in the enhanced the killing of cancer cells may also be suitable. In one embodiment, one or more of the pentaaza macrocyclic ring complex and the immunotherapeutic agent (e.g., immune checkpoint inhibitor, adoptive T-cell transfer therapy, cancer vaccine) may be administered before the dose of the chemotherapeutic agent, and the remaining one or more of the pentaaza macrocyclic ring complex and the immunotherapeutic agent (e.g., immune checkpoint inhibitor, adoptive T-cell transfer therapy, cancer vaccine) can be administered after the dose of the chemotherapeutic agent. One or more of the pentaaza macrocyclic ring complex and the immunotherapeutic agent (e.g., immune checkpoint inhibitor, adoptive T-cell transfer therapy, cancer vaccine) may also be administered both before and after administration of the dose of chemotherapeutic agent.

In one embodiment, a course of chemotherapy includes a singular dose of a chemotherapeutic agent. In another embodiment, a course of chemotherapy includes a plurality of doses of a chemotherapeutic agent given over a predetermined period of time, such as over the course of hours, weeks, days and even months. The plural doses may be either of the same magnitude or varying, and can include doses of the same or different chemotherapeutic agents and/or a combination of chemotherapeutic agents. The administration of the pentaaza macrocyclic ring complex and the immunotherapeutic agent (e.g., immune checkpoint inhibitor, adoptive T-cell transfer therapy, cancer vaccine) during the course of chemotherapy can be selected to enhance the cancer treating effects of the chemotherapy, such as by increasing intracellular levels of hydrogen peroxide to promote oxidative stress in the cancer cells. In one embodiment, the pentaaza macrocyclic ring complex and the immunotherapeutic agent (e.g., immune checkpoint inhibitor, adoptive T-cell transfer therapy, cancer vaccine) are administered within a predetermined duration before or after each dose, such as the predetermined duration discussed above. In another embodiment, the pentaaza macrocyclic ring complex and the immunotherapeutic agent (e.g., immune checkpoint inhibitor, adoptive T-cell transfer therapy, cancer vaccine) are administered within a predetermined duration of time before or after only select doses. In yet another embodiment, at least one of the pentaaza macrocyclic ring complex and the immunotherapeutic agent (e.g., immune checkpoint inhibitor, adoptive T-cell transfer therapy, cancer vaccine) are administered within a predetermined duration of time before the doses, while another of the pentaaza macrocyclic ring complex and the immunotherapeutic agent (e.g., immune checkpoint inhibitor, adoptive T-cell transfer therapy, cancer vaccine) are administered within a predetermined duration of time after the doses. In a further embodiment, at least one of the pentaaza macrocyclic ring complex and the immunotherapeutic agent (e.g., immune checkpoint inhibitor, adoptive T-cell transfer therapy, cancer vaccine) is administered only within the predetermined duration before or after select doses, while another of the pentaaza macrocyclic ring complex and the immunotherapeutic agent (e.g., immune checkpoint inhibitor, adoptive T-cell transfer therapy, cancer vaccine) is administered only within the predetermined duration before or after doses other than the select doses.

In yet another embodiment, at least one of the pentaaza macrocyclic ring complex and the immunotherapeutic agent (e.g., immune checkpoint inhibitor, adoptive T-cell transfer therapy, cancer vaccine) is administered in combination with both a radiation therapy and chemotherapy.

Embodiments according to aspects of the disclosure are provided below, although the disclosure is not limited thereto.

Embodiment 1

A method of treating a cancer in a mammalian subject afflicted with the cancer, the method comprising:
administering to the subject an immune checkpoint inhibitor;
administering to the subject a pentaaza macrocyclic ring complex corresponding to the formula (I) below, prior to, concomitantly with, or after administration of the immune checkpoint inhibitor, to increase the response of the cancer to the immune checkpoint inhibitor:

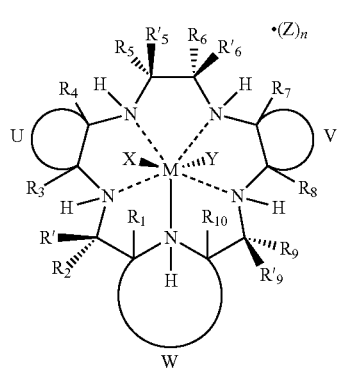

(I)

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;
X and Y represent suitable ligands which are derived from any monodentate or polydentate coordinating ligand or ligand system or the corresponding anion thereof;
Z is a counterion;
n is an integer from 0 to 3; and
the dashed lines represent coordinating bonds between the nitrogen atoms of the macrocycle and the transition metal, manganese.

Embodiment 2

The method according to Embodiment 1, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

Embodiment 3

The method according to Embodiment 1 or 2, wherein W is an unsubstituted pyridine moiety.

Embodiment 4

The method according to any preceding Embodiment, wherein U and V are transcyclohexanyl fused rings.

Embodiment 5

The method according to any preceding Embodiment, wherein the pentaaza macrocyclic ring complex is represented by formula (II):

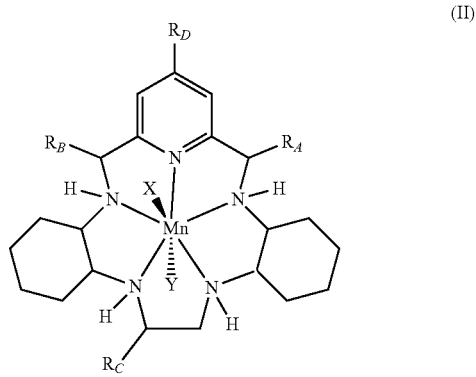

(II)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 6

The method according to any preceding Embodiment, wherein the pentaaza macrocyclic ring complex is represented by formula (III) or formula (IV):

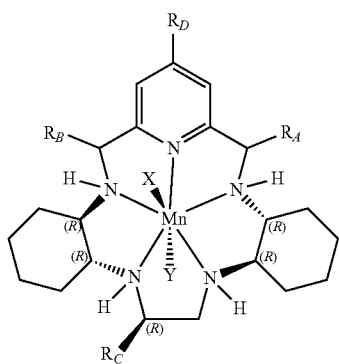

(III)

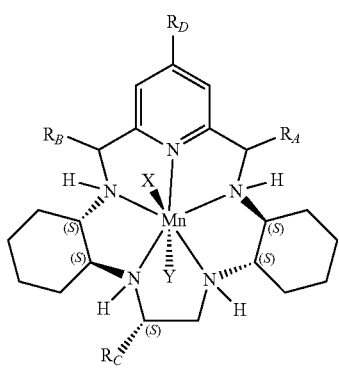

(IV)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 7

The method according to any preceding Embodiment, wherein the pentaaza macrocyclic ring complex is a compound represented by a formula selected from the group consisting of formulae (V)-(XVI):

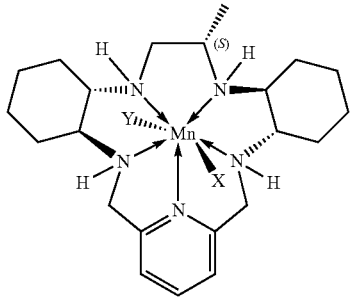

(V)

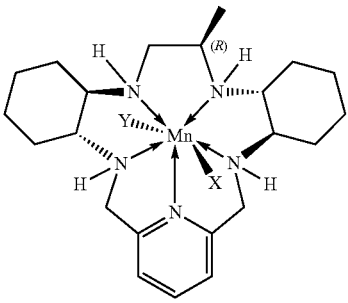

(VI)

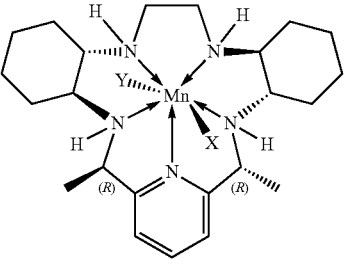

(VII)

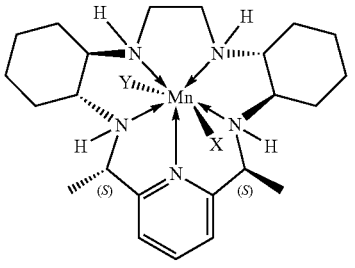

(VIII)

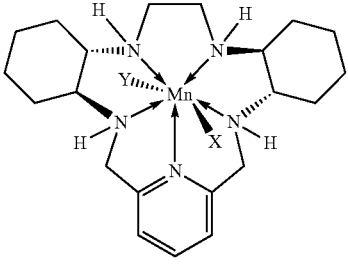

(IX)

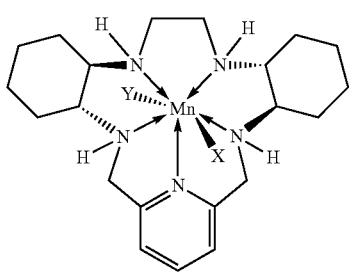 (X)

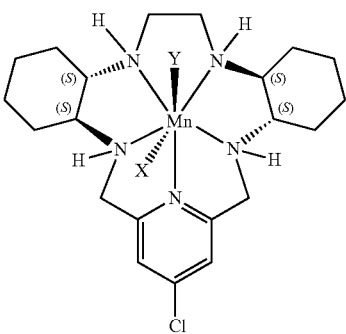 (XI)

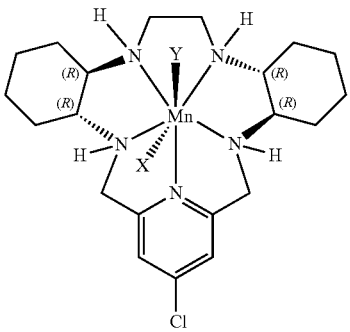 (XII)

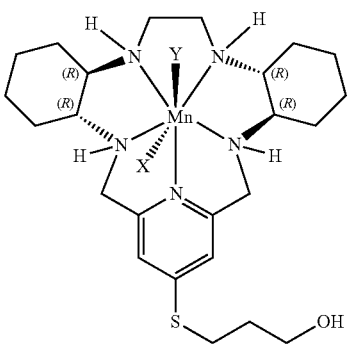 (XIII)

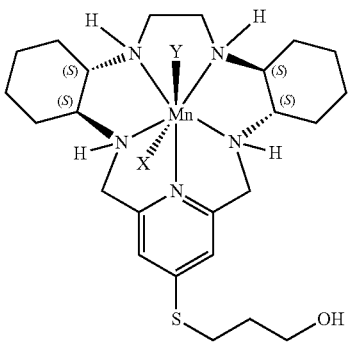 (XIV)

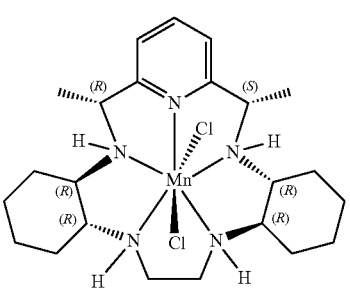 (XV)

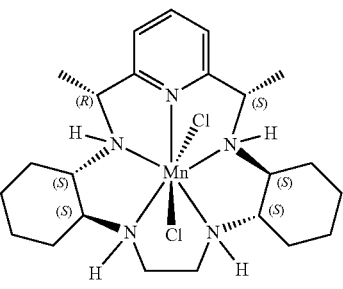 (XVI)

Embodiment 8

The method according to any preceding Embodiment, wherein X and Y are independently selected from substituted or unsubstituted moieties of the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof;

or X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(=O)$R_{13}$ where $X_5$ is NH or O, and $R_{13}$ is C1-C18 alkyl, substituted or unsubstituted aryl or C1-C18 aralkyl, or —$OR_{14}$, where $R_{14}$ is C1-C18 alkyl, substituted or unsubstituted aryl or C1-C18 aralkyl, or together with $X_4$ is (=O); and each $X_4$ is independently hydrogen or together with $X_3$ is (=O);

or X and Y are independently selected from the group consisting of charge-neutralizing anions which are derived from any monodentate or polydentate coordinating ligand and a ligand system and the corresponding anion thereof;

or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

Embodiment 9

The method according to any preceding Embodiment, wherein X and Y are independently selected from the group consisting of fluoro, chloro, bromo, and iodo anions.

Embodiment 10

The method according to any one of Embodiments 1-8, wherein X and Y are independently selected from the group consisting of alkyl carboxylates, aryl carboxylates and arylalkyl carboxylates.

Embodiment 11

The method according to any one of Embodiments 1-8, wherein X and Y are independently amino acids.

Embodiment 12

The method according to any one of Embodiments 1-8 Embodiment, wherein the pentaaza macrocyclic ring complex is a compound represented by the formula:

(4419)

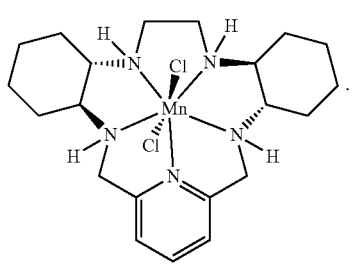

Embodiment 13

The method according to any one of Embodiments 1-8, wherein the pentaaza macrocyclic ring complex is a compound represented by the formula:

(4403)

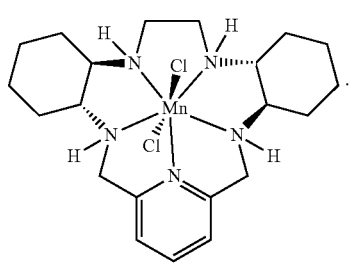

Embodiment 14

The method according to anyone of Embodiments 1-8, wherein the pentaaza macrocyclic ring complex is a compound represented by the formula:

(4401)

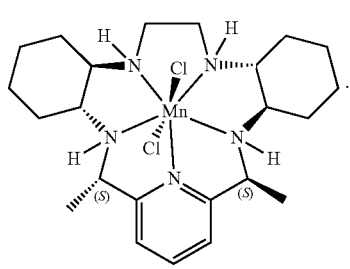

Embodiment 15

The method according to any one of Embodiments 1-8, wherein the pentaaza macrocyclic ring complex is represented by the formula:

GC4444

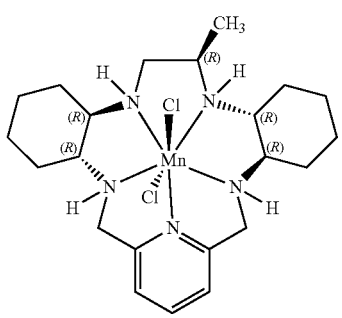

Embodiment 16

The method according to any one of Embodiments 1-8, wherein the pentaaza macrocyclic ring complex is represented by the formula:

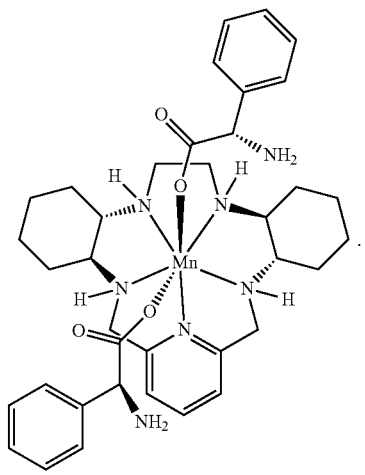

GC4702

Embodiment 17

The method according to any one of Embodiments 1-8, wherein the pentaaza macrocyclic ring complex is represented by the formula:

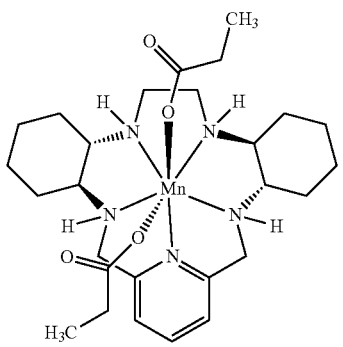

GC4711

Embodiment 18

The method according to any preceding Embodiment, wherein initial administration of the pentaaza macrocyclic ring complex in a course of therapy is administered a predetermined period of time after initial administration of the immune checkpoint inhibitor.

Embodiment 19

The method according to Embodiment 18, wherein initial administration of the pentaaza macrocyclic ring complex in the course of therapy is no less than 3 days after initial administration of the immune checkpoint inhibitor.

Embodiment 20

The method according to Embodiment 19, wherein initial administration of the pentaaza macrocyclic ring complex in the course of therapy is no less than 6 days after initial administration of the immune checkpoint inhibitor.

Embodiment 21

The method according to Embodiment 19, wherein initial administration of the pentaaza macrocyclic ring complex in the course of therapy is in a range of from 3 days to 9 weeks after initial administration of the immune checkpoint inhibitor.

Embodiment 22

The method according to any preceding Embodiment, wherein initial administration of the pentaaza macrocyclic ring complex in the course of therapy follows two doses of the immune checkpoint inhibitor.

Embodiment 23

The method according to Embodiment 22, wherein initial administration of the pentaaza macrocyclic ring complex in the course of therapy follows three doses of the immune checkpoint inhibitor.

Embodiment 24

The method according to Embodiment 23, wherein initial administration of the pentaaza macrocyclic ring complex in the course of therapy follows four doses of the immune checkpoint inhibitor.

Embodiment 25

The method according to Embodiment 24, wherein initial administration of the pentaaza macrocyclic ring complex in the course of therapy follows five doses of the immune checkpoint inhibitor.

Embodiment 26

The method according to any preceding Embodiment, wherein doses of the pentaaza macrocyclic ring complex provided in a course of cancer therapy are provided on separate days from any dose of the immune checkpoint inhibitor.

Embodiment 27

The method according to any preceding Embodiment, further comprising administering one or more of radiation therapy and chemotherapy to the subject, prior to, concomitantly with, or after administration of one or more of the immune checkpoint inhibitor and pentaaza macrocyclic ring complex.

Embodiment 28

The method according to Embodiment 27, wherein radiation therapy is administered concomitantly with administration of one or more of the immune checkpoint inhibitor and pentaaza macrocyclic ring complex.

Embodiment 29

The method according to any preceding Embodiment, comprising administering the pentaaza macrocyclic ring complex to a subject that is not receiving radiation therapy.

Embodiment 30

The method according to any preceding Embodiment, comprising administering the immune checkpoint inhibitor and pentaaza macrocyclic ring complex to a subject that is not receiving radiation therapy.

Embodiment 31

The method according to any preceding Embodiment, wherein a course of therapy comprising administration of the pentaaza macrocyclic ring complex and the immunce checkpoint inhibitor, is administered to a subject that does not receive radiation therapy during the course of therapy.

Embodiment 32

The method according to any of Embodiments 1-28, comprising administering one or more of the pentaaza macrocyclic ring complex and immune checkpoint inhibitor to the subject on a day other than a day that the subject is receiving radiation therapy.

Embodiment 33

The method according to any preceding Embodiment, comprising administering a course of therapy comprising administration of the immune checkpoint inhibitor and pentaaza macrocyclic ring complex to a subject that has not received radiation therapy for at least a day.

Embodiment 34

The method according to any preceding Embodiment, comprising administering a course of therapy comprising administration of the immune checkpoint inhibitor and pentaaza macrocyclic ring complex to a subject that has not received radiation therapy for at least a week.

Embodiment 35

The method according to any preceding Embodiment, comprising administering a course of therapy comprising administration of the immune checkpoint inhibitor and pentaaza macrocyclic ring complex to a subject that has not received radiation therapy for at least a month.

Embodiment 36

The method according to any preceding Embodiment, comprising administering a course of therapy comprising administration of the immune checkpoint inhibitor and pentaaza macrocyclic ring complex to a subject that has not received radiation therapy for at least six months.

Embodiment 37

The method according to any preceding Embodiment, comprising administering the immune checkpoint inhibitor and pentaaza macrocyclic ring complex to a subject, and delaying any radiation therapy optionally administered to the subject thereafter by at least one day after a final administration of the pentaaza macrocyclic ring complex.

Embodiment 38

The method according to any preceding Embodiment, comprising administering the immune checkpoint inhibitor and pentaaza macrocyclic ring complex to a subject, and delaying any radiation therapy optionally administered to the subject thereafter by at least one week after a final administration of the pentaaza macrocyclic ring complex.

Embodiment 39

The method according to any preceding Embodiment, comprising administering the immune checkpoint inhibitor and pentaaza macrocyclic ring complex to a subject, and delaying any radiation therapy optionally administered to the subject thereafter by at least one month after a final administration of the pentaaza macrocyclic ring complex.

Embodiment 40

The method according to any preceding Embodiment, comprising administering the immune checkpoint inhibitor and pentaaza macrocyclic ring complex to a subject, and delaying any radiation therapy optionally administered to the subject thereafter by at least six months after a final administration of the pentaaza macrocyclic ring complex.

Embodiment 41

The method according to any preceding Embodiment, wherein the checkpoint inhibitor interacts with one or more of cytotoxic T-lymphocyte antigen 4 (CTLA4), programmed death 1 (PD-1), programmed death ligand 1 (PDL-1), PDL-2, lymphocyte activation genes-3 (LAG3), B7 homolog 3 (B7-H3), B7 homolog 4 (B7-H4), indoleamine (2,3)-dioxygenase (IDO), adenosine A2a receptor (A2AR), neuritin, B- and T-lymphocyte attenuator (BTLA), killer immunoglobulin-like receptors (KIR), T cell immunoglobulin and mucin domain-containing protein 3 (TIME-3), inducible T cell costimulator (ICOS), CD27, CD28, CD40, CD137, CD160, CD244, HVEM, GAL9, VISTA, 2B4, CGEN-15049, CHK 1, CHK2, GITR, CD47 and combinations thereof.

Embodiment 42

The method according to any preceding Embodiment, wherein the checkpoint inhibitor comprises one or more of small molecule inhibitor, an antibody, an antigen binding fragment, and an Ig fusion protein.

Embodiment 43

The method according to any preceding Embodiment, wherein the checkpoint inhibitor is selected from the group consisting of ipilimumab, nivolumab, pembrolizumab, pidilizumab, areluman, tremelimumab, atezolizumab, AMP-224, MPDL3280A, MDX-1105, MDX-1106, MEDI-4736, IMP321, INCB024360, NLG-919, indoximod, AUNP 12, galiximab, avelumab, varlilumab, mogamulizumab, CP-870,893, MEDI-6469, IPH2101, urelumab, lirilumab, BMS-986016, MGA271, IMP321, BMS-936559, MSB0010718C, anti-OX40, MK-3475, CT-011, BY55, AMP224, and BGB-A317.

Embodiment 44

The method according to any preceding Embodiment, wherein the checkpoint inhibitor is at least one of an anti-CTLA4 antibody, an anti-PD-1 antibody and an anti-PDL-1 antibody.

Embodiment 45

The method according to any preceding Embodiment, further comprising administering one or more of adoptive T-cell transfer therapy and a cancer vaccine to the subject, either prior to, concomitantly with, or after administration of one or more of the checkpoint inhibitor and pentaaza macrocyclic ring complex.

Embodiment 46

The method according to any preceding Embodiment, wherein the cancer is selected from the group consisting of breast cancer, non-small-cell lung cancer, melanoma, renal cell carcinoma, urothelial carcinoma, bladder cancer, pancreatic cancer, head and neck cancers, colorectal cancer, prostate cancer, brain cancer, spindle cell carcinoma, and oral squamous cell carcinoma.

Embodiment 47

The method according to any preceding Embodiment, wherein the pentaaza macrocyclic ring complex is administered to the subject in a dose in a range of from 0.2 mg/kg to 40 mg/kg.

Embodiment 48

The method according to Embodiment 47, wherein the pentaaza macrocyclic ring complex is administered to the subject in a dose in a range of from 0.2 mg/kg to 24 mg/kg.

Embodiment 49

The method according to Embodiment 48, wherein the pentaaza macrocyclic ring complex is administered to the subject in a dose in a range of from 0.2 mg/kg to 10 mg/kg.

Embodiment 50

The method according to any preceding Embodiment, wherein the pentaaza macrocyclic ring complex is administered via at least one of parenteral route and oral route.

Embodiment 51

The method according to Embodiment 40, wherein the pentaaza macrocyclic ring complex is administered intraperitoneally or intravenously.

Embodiment 52

A method of treating a cancer in a mammalian subject afflicted with the cancer, the method comprising:
administering to the subject an adoptive T-cell transfer therapy;
administering to the subject a pentaaza macrocyclic ring complex corresponding to the formula (I) below, prior to, concomitantly with, or after the adoptive T-cell transfer therapy, to increase the response of the cancer to the adoptive T-cell transfer therapy,

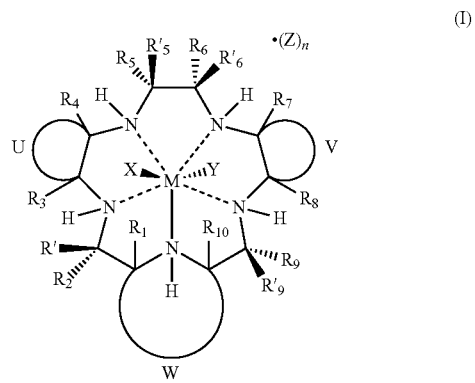

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;
U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;
X and Y represent suitable ligands which are derived from any monodentate or polydentate coordinating ligand or ligand system or the corresponding anion thereof;
Z is a counterion;
n is an integer from 0 to 3; and
the dashed lines represent coordinating bonds between the nitrogen atoms of the macrocycle and the transition metal, manganese.

Embodiment 53

The method according to Embodiment 52, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

Embodiment 54

The method according to Embodiment 52 or 53, wherein W is an unsubstituted pyridine moiety.

Embodiment 55

The method according to any of Embodiments 52-54, wherein U and V are transcyclohexanyl fused rings.

Embodiment 56

The method according to any of Embodiments 52-55, wherein the pentaaza macrocyclic ring complex is represented by formula (II):

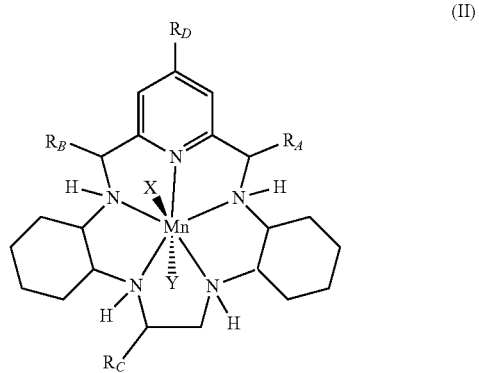

(II)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 57

The method according to any of Embodiments 52-56, wherein the pentaaza macrocyclic ring complex is represented by formula (III) or formula (IV):

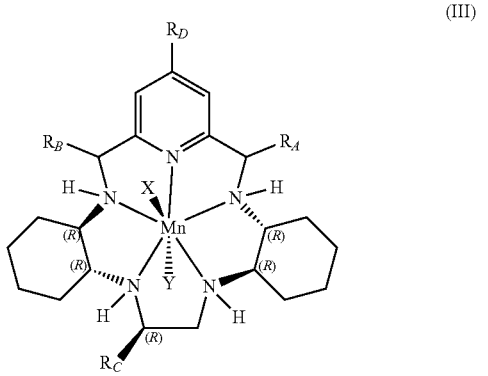

(III)

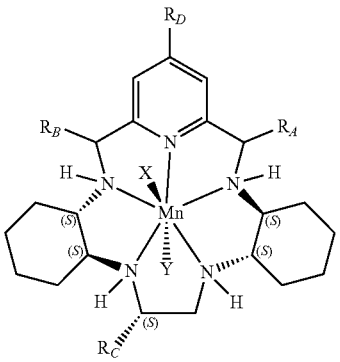

(IV)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 58

The method according to any of Embodiments 52-57, wherein the pentaaza macrocyclic ring complex is a compound represented by a formula selected from the group consisting of formulae (V)-(XVI):

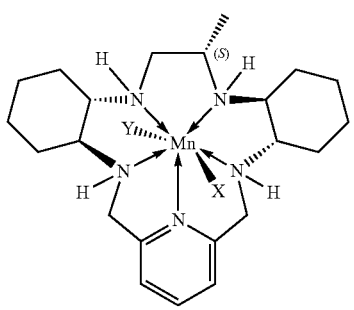

(V)

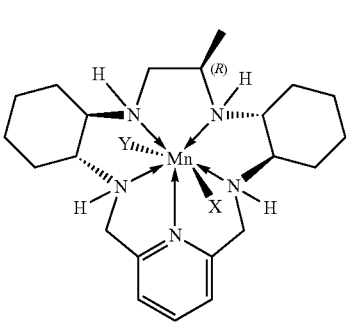

(VI)

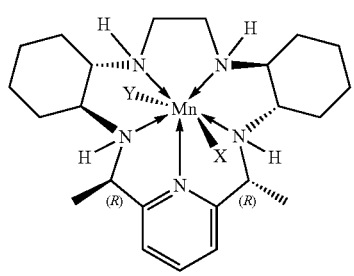
(VII)
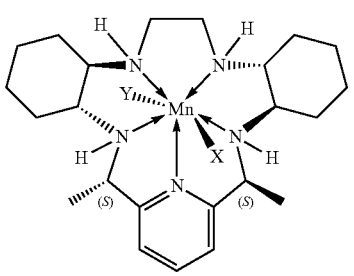
(VIII)
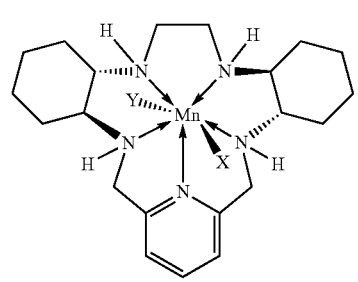
(IX)
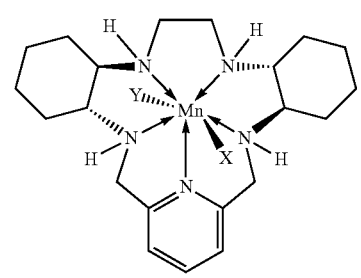
(X)
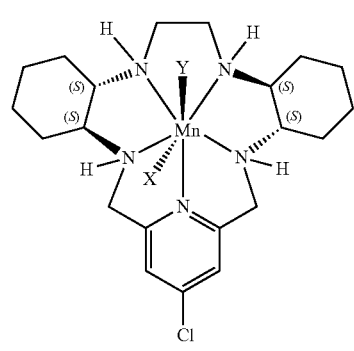
(XI)
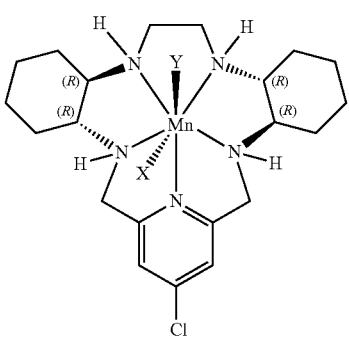
(XII)
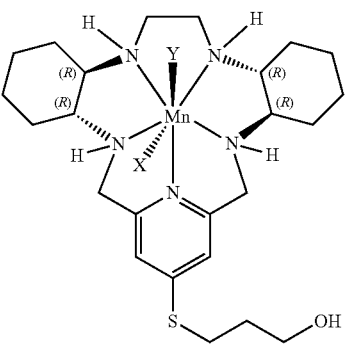
(XIII)
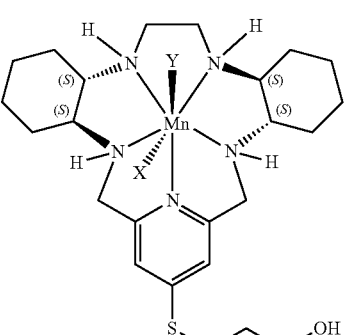
(XIV)
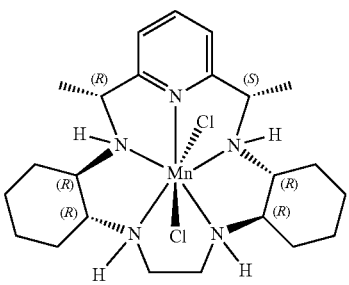
(XV)
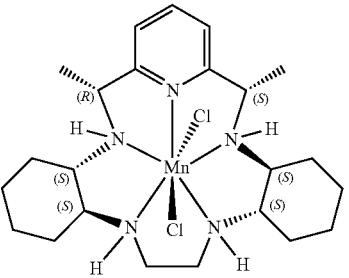
(XVI)

Embodiment 59

The method according to any of Embodiments 52-58, wherein X and Y are independently selected from substituted or unsubstituted moieties of the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof;

or X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(=O)$R_{13}$ where $X_5$ is NH or O, and $R_{13}$ is C1-C18 alkyl, substituted or unsubstituted aryl or C1-C18 aralkyl, or —$OR_{14}$, where $R_{14}$ is C1-C18 alkyl, substituted or unsubstituted aryl or C1-C18 aralkyl, or together with $X_4$ is (=O); and each $X_4$ is independently hydrogen or together with $X_3$ is (=O);

or X and Y are independently selected from the group consisting of charge-neutralizing anions which are derived from any monodentate or polydentate coordinating ligand and a ligand system and the corresponding anion thereof;

or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

Embodiment 60

The method according to any of Embodiments 52-59, wherein X and Y are independently selected from the group consisting of fluoro, chloro, bromo, and iodo anions.

Embodiment 61

The method according to any one of Embodiments 52-59, wherein X and Y are independently selected from the group consisting of alkyl carboxylates, aryl carboxylates and arylalkyl carboxylates.

Embodiment 62

The method according to any one of Embodiments 52-59, wherein X and Y are independently amino acids.

Embodiment 63

The method according to any one of Embodiments 52-59, wherein the pentaaza macrocyclic ring complex is a compound represented by the formula:

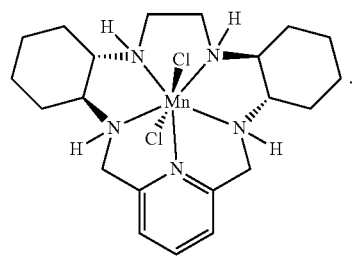

(4419)

Embodiment 64

The method according to any one of Embodiments 52-62, wherein the pentaaza macrocyclic ring complex is a compound represented by the formula:

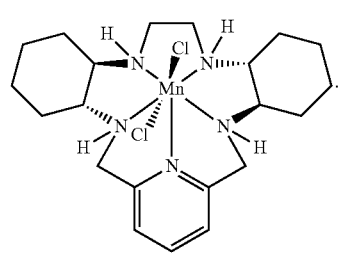

(4403)

Embodiment 65

The method according to any one of Embodiments 52-62, wherein the pentaaza macrocyclic ring complex is a compound represented by the formula:

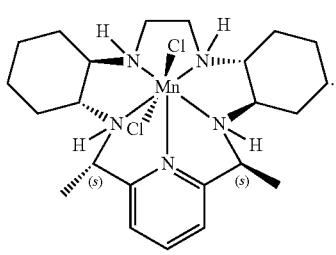

(4401)

Embodiment 66

The method according to any one of Embodiments 52-62, wherein the pentaaza macrocyclic ring complex is represented by the formula:

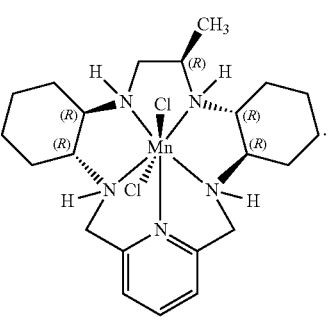

GC4444

Embodiment 67

The method according to any one of Embodiments 52-62, wherein the pentaaza macrocyclic ring complex is represented by the formula:

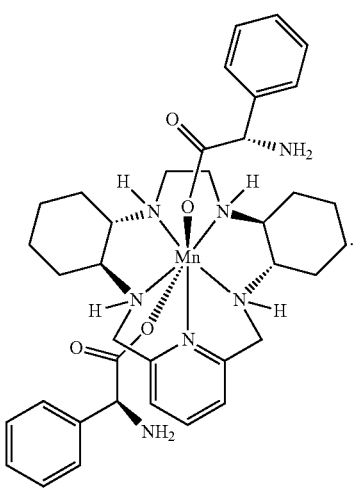

GC4702

Embodiment 68

The method according to any one of Embodiments 52-62, wherein the pentaaza macrocyclic ring complex is represented by the formula:

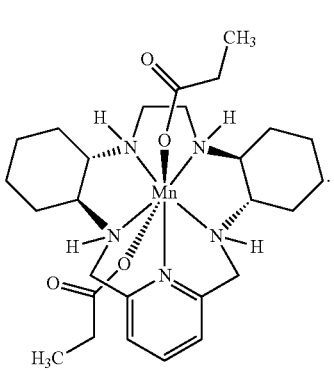

GC4711

Embodiment 69

The method according to any of Embodiments 52-68, wherein initial administration of the pentaaza macrocyclic ring complex in a course of therapy is a predetermined period of time after initial administration of the adoptive T-cell transfer therapy.

Embodiment 70

The method according to any of Embodiments 52-68, further comprising administering one or more of radiation therapy and chemotherapy to the subject, prior to, concomitantly with, or after administration of one or more of the adoptive T-cell transfer therapy and pentaaza macrocyclic ring complex.

Embodiment 71

The method according to any of Embodiments 52-68, comprising administering the adoptive T-cell transfer therapy and pentaaza macrocyclic ring complex to a subject that is not receiving radiation therapy.

Embodiment 72

The method according to any of Embodiments 52-71, wherein the adoptive T-cell transfer therapy comprises administering to the subject cancer-specific autologous or allogeneic T-cells.

Embodiment 73

The method according to any of Embodiments 52-72, wherein the adoptive T-cell transfer therapy comprises providing autologous tumor infiltrating lymphocytes, antigen-expanded CD8+ and/or CD4+ T cells, and genetically modified T cells that express T-cell receptors (TCR) that recognize tumor antigens.

Embodiment 74

The method according to any of Embodiments 52-73, further comprising administering one or more of an immune checkpoint inhibitor and a cancer vaccine to the subject, either prior to, concomitantly with, or after administration of one or more of the adoptive T-cell transfer therapy and pentaaza macrocyclic ring complex.

Embodiment 75

The method according to any of Embodiments 52-74, wherein the cancer is selected from the group consisting of breast cancer, non-small-cell lung cancer, melanoma, renal cell carcinoma, urothelial carcinoma, bladder cancer, pancreatic cancer, head and neck cancers, colorectal cancer, prostate cancer, brain cancer, spindle cell carcinoma, and oral squamous cell carcinoma.

Embodiment 76

The method according to any of Embodiments 52-75, wherein the pentaaza macrocyclic ring complex is administered via at least one of parenteral route and oral route.

Embodiment 77

The method according to Embodiment 76, wherein the pentaaza macrocyclic ring complex is administered intraperitoneally or intravenously.

Embodiment 78

A method of treating a cancer in a mammalian subject afflicted with the cancer, the method comprising:
administering to the subject a cancer vaccine;
administering to the subject a pentaaza macrocyclic ring complex corresponding to the formula (I) below, prior to, concomitantly with, or after administration of the cancer vaccine, to increase the response of the cancer to the cancer vaccine,

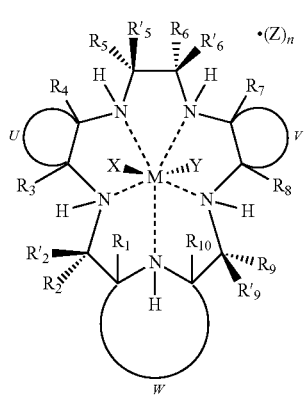

(I)

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;
X and Y represent suitable ligands which are derived from any monodentate or polydentate coordinating ligand or ligand system or the corresponding anion thereof;
Z is a counterion;
n is an integer from 0 to 3; and
the dashed lines represent coordinating bonds between the nitrogen atoms of the macrocycle and the transition metal, manganese.

Embodiment 79

The method according to Embodiment 78, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

Embodiment 80

The method according to Embodiment 78 or 79, wherein W is an unsubstituted pyridine moiety.

Embodiment 81

The method according to any of Embodiments 78-80, wherein U and V are transcyclohexanyl fused rings.

Embodiment 82

The method according to any of Embodiments 78-69, wherein the pentaaza macrocyclic ring complex is represented by formula (II):

(II)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 83

The method according to any of Embodiments 78-82, wherein the pentaaza macrocyclic ring complex is represented by formula (III) or formula (IV):

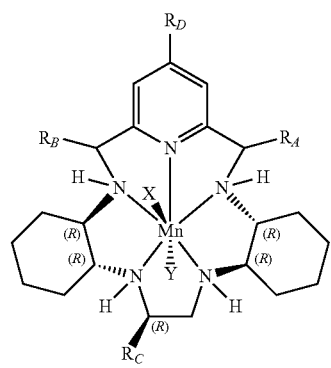

(III)

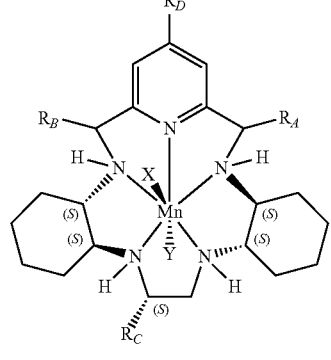

(IV)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Embodiment 84

The method according to any of Embodiments 78-82, wherein the pentaaza macrocyclic ring complex is a compound represented by a formula selected from the group consisting of formulae (V)-(XVI):

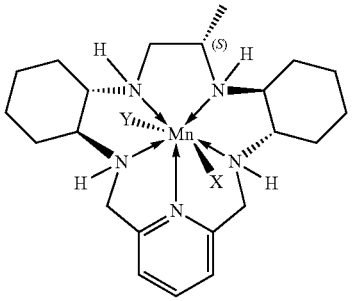

(V)

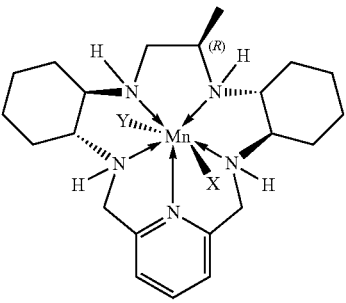

(VI)

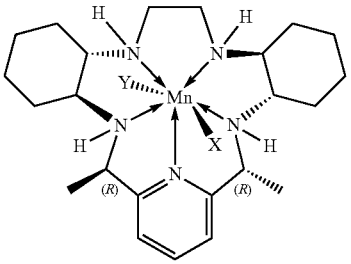

(VII)

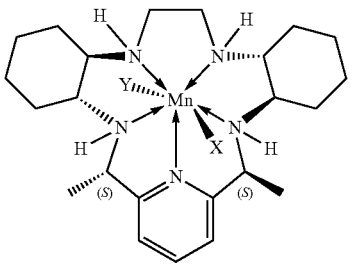

(VIII)

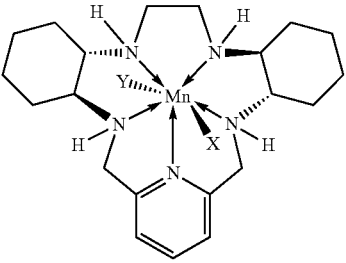

(IX)

(X)
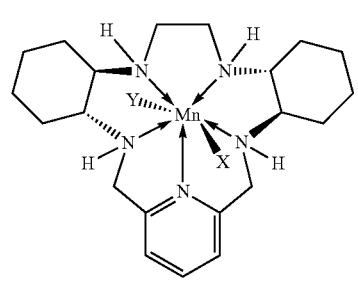

(XI)
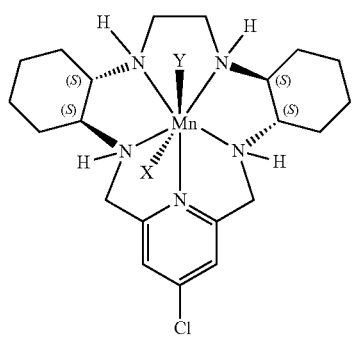

(XII)
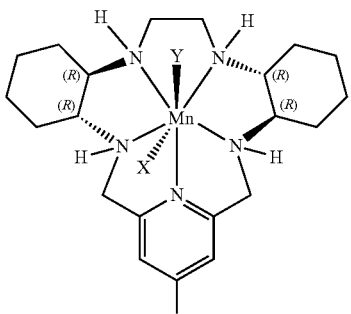

(XIII)
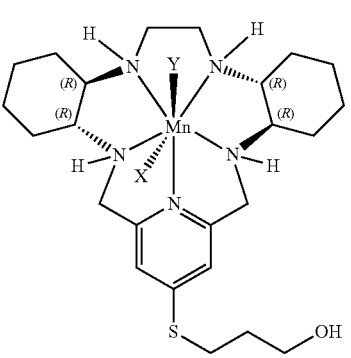

(XIV)
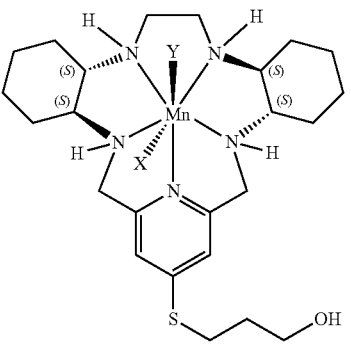

(XV)
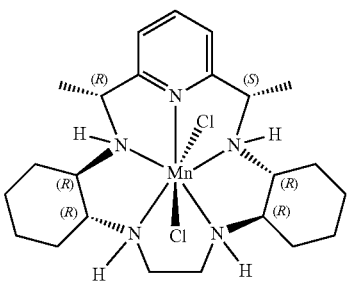

(XVI)
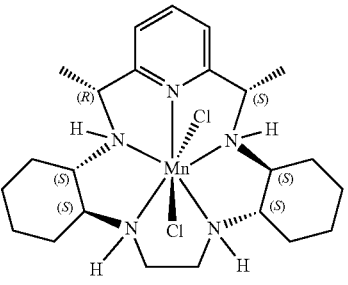

Embodiment 85

The method according to any of Embodiments 78-84, wherein X and Y are independently selected from substituted or unsubstituted moieties of the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof;

or X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(=O)$R_{13}$ where $X_5$ is NH or O, and $R_{13}$ is C1-C18 alkyl, substituted or unsubstituted aryl or C1-C18 aralkyl, or —$OR_{14}$, where $R_{14}$ is C1-C18 alkyl, substituted or unsubstituted aryl or C1-C18 aralkyl, or together with $X_4$ is (=O); and each $X_4$ is independently hydrogen or together with $X_3$ is (=O);

or X and Y are independently selected from the group consisting of charge-neutralizing anions which are derived from any monodentate or polydentate coordinating ligand and a ligand system and the corresponding anion thereof;

or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

Embodiment 86

The method according to any of Embodiments 78-85, wherein X and Y are independently selected from the group consisting of fluoro, chloro, bromo, and iodo anions.

Embodiment 87

The method according to any one of Embodiments 78-85, wherein X and Y are independently selected from the group consisting of alkyl carboxylates, aryl carboxylates and arylalkyl carboxylates.

Embodiment 88

The method according to any one of Embodiments 78-85, wherein X and Y are independently amino acids.

Embodiment 89

The method according to any one of Embodiments 78-85, wherein the pentaaza macrocyclic ring complex is a compound represented by the formula:

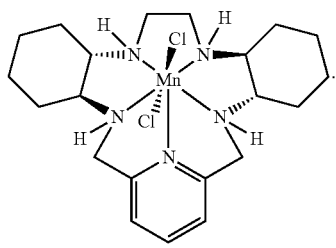

(4419)

Embodiment 90

The method according to any one of Embodiments 78-85, wherein the pentaaza macrocyclic ring complex is a compound represented by the formula:

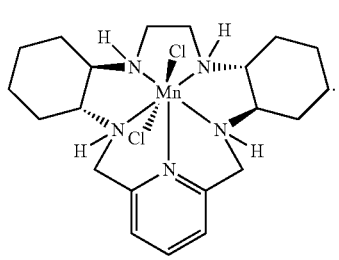

(4403)

Embodiment 91

The method according to any one of Embodiments 78-85, wherein the pentaaza macrocyclic ring complex is a compound represented by the formula:

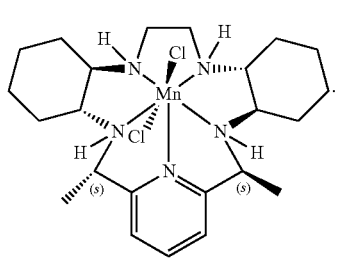

(4401)

Embodiment 92

The method according to any one of Embodiments 78-85, wherein the pentaaza macrocyclic ring complex is represented by the formula:

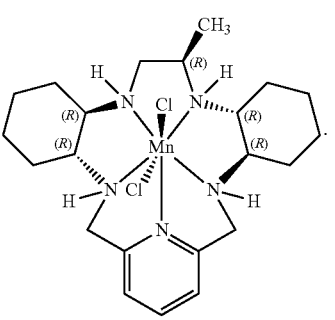

GC4444

Embodiment 93

The method according to any one of Embodiments 78-85, wherein the pentaaza macrocyclic ring complex is represented by the formula:

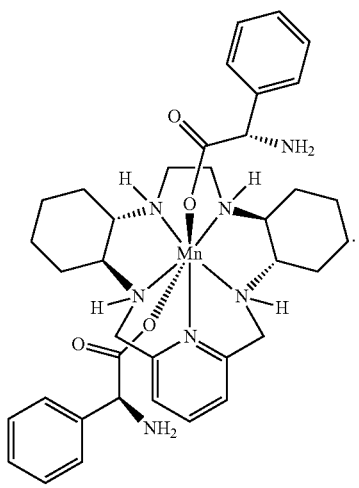

GC4702

Embodiment 94

The method according to any one of Embodiments 78-85, wherein the pentaaza macrocyclic ring complex is represented by the formula:

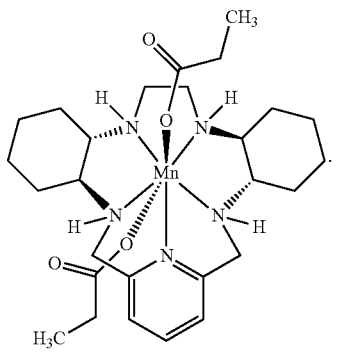

GC4711

Embodiment 95

The method according to any of Embodiments 78-94, wherein initial administration of the pentaaza macrocyclic ring complex in a course of therapy is a predetermined period of time after initial administration of the cancer vaccine.

Embodiment 96

The method according to any of Embodiments 78-95, further comprising administering one or more of radiation therapy and chemotherapy to the subject, prior to, concomitantly with, or after administration of one or more of the cancer vaccine and pentaaza macrocyclic ring complex.

Embodiment 97

The method according to any of Embodiments 78-96, comprising administering the cancer vaccine and pentaaza macrocyclic ring complex to a subject that is not receiving radiation therapy.

Embodiment 98

The method according to any of Embodiments 78-97, wherein the cancer vaccine is selected from the group consisting of tumor cell vaccines, antigen vaccines, dendritic cell vaccines, DNA vaccines and vector based vaccines.

Embodiment 99

The method according to any of Embodiments 78-98, wherein the cancer vaccine is selected from the group consisting of M-Vax (Avax Technologies), Provenge (Dendreon), GRNVAC1 (Geron), Bexidem (IDM Pharma), Uvidem (IDM Pharma), Collidem (IDM Pharma), INGN 225 (Introgen Therapuetics), M3Tk (MolMed), DC-Vax (Northwest Biotherapeutics), CVac (Prima Biomed), GVAX (Cell Genesys), Lucanix (NovaRx), Onyvax-P (Onyvax), HSPP-96 Oncophage (Antigenics), BiovaxlD (Biovest International), NeuVax (Apthera), CDX-110 (CeppDex), GV1001 (Pharmexa), CYT004-MelQbG10 (Cytos Biotechnology), li-Key/HER2/neu (Generex Biotechnology), MAGE-A3 (Glaxo-SmithKline Biologicals), IDM-2101 (IDM Pharma), IMA901IMA910 (Immatics Biotechnologies), melanoma cancer vaccine (Norwood Immunology), inCVAX (Immunophotonics) and Stimuvax (Oncothyreon).

Embodiment 100

The method according to any of Embodiments 78-99, further comprising administering one or more of an immune checkpoint inhibitor and an adoptive T-cell transfer therapy to the subject, either prior to, concomitantly with, or after administration of one or more of the cancer vaccine and pentaaza macrocyclic ring complex.

Embodiment 101

The method according to any of Embodiments 78-100, wherein the cancer is selected from the group consisting of breast cancer, non-small-cell lung cancer, melanoma, renal cell carcinoma, urothelial carcinoma, bladder cancer, pancreatic cancer, head and neck cancers, colorectal cancer, prostate cancer, brain cancer, spindle cell carcinoma, and oral squamous cell carcinoma.

Embodiment 102

The method according to any of Embodiments 78-101, wherein the pentaaza macrocyclic ring complex is administered via at least one of parenteral route and oral route.

Embodiment 103

The method according to Embodiment 102, wherein the pentaaza macrocyclic ring complex is administered intraperitoneally or intravenously.

Embodiment 104

A method of treating a viral infection in a mammalian subject in need thereof, comprising.
administering to the subject at least one of an immune checkpoint inhibitor, an adoptive T-cell transfer therapy, and a vaccine; and
administering to the subject a pentaaza macrocyclic ring complex corresponding to the formula (I) below, prior to, concomitantly with, or after the at least one immune checkpoint inhibitor, adoptive T-cell transfer therapy, and vaccine, to increase the effectiveness of the at least one immune checkpoint, adoptive T-cell transfer therapy, and vaccine in treating the viral infection,

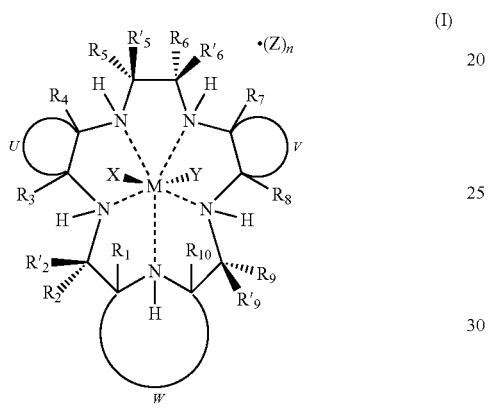

(I)

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;
U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;
X and Y represent suitable ligands which are derived from any monodentate or polydentate coordinating ligand or ligand system or the corresponding anion thereof;
Z is a counterion;
n is an integer from 0 to 3; and
the dashed lines represent coordinating bonds between the nitrogen atoms of the macrocycle and the transition metal, manganese.

Embodiment 105

A kit comprising:
at least one of an immune checkpoint inhibitor, T-cells for an adoptive T-cell transfer therapy, and a cancer vaccine; and
a pentaaza macrocyclic ring complex according to formula (I)

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;
U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

EXAMPLES

The following non-limiting examples are provided to further illustrate aspects of the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Pentaaza-macrocyclic ring complexes may protect cells including T-cells and other immunologically active cells, including CD8+, CD4+, natural killer (NK), lymphokine-activated killer (LAK) and other cytotoxic or helper T lymphocytes from oxidative stressors including those within the tumor or tumor microenvironment. Here, we report evidence supporting that GC4419 (Galera Therapeutics, St. Louis, Mo.), a Mn(II) pentaaza-macrocyclic ring complex both alone and in combination with immune response checkpoint inhibitors can increase the numbers of CD8+, and CD4+ (but not CD4+/CD25+/FoxP3+), T-cells. Such increases are believed to be beneficial in treating cancer, and in fact we also report here that GC4419 in combination with an immune response checkpoint inhibitor increases anti-tumor response versus treatment with the immune response checkpoint inhibitor as a single agent.

These results have significant implications with respect to combinations with immunotherapies other than immune checkpoint inhibitor treatments as well. This is because adoptive T-cell transfer therapies exogenously add T(effector)-cells, which are, or are similar to, CD8+ T-cells, and since, in addition, certain subsets of CD4+ (specifically excluding CD4+/CD25+/FoxP3) T-cells are believed to be important in achieving good response with adoptive T-cell transfer therapies. Accordingly, as GC4419 increases CD4+ and/or CD8+ T-cell numbers, it is believed that GC4419 and other pentaaza macrocyclic ring complexes may also be beneficial in increasing the anti-tumor response to an adoptive T-cell transfer therapy.

Further, the results described herein are relevant to immunotherapies such as treatments with cancer vaccines because the administration of a vaccine for treatment of cancer results in the generation of CD8+ and/or CD4+ T-cells. Accordingly, as GC4419 increases CD8+ and/or CD4+ T-cell numbers, it is believed that GC4419 and other macrocyclic ring complexes may also be beneficial in increasing the anti-tumor response to a therapeutic cancer vaccine.

Further, since therapeutic vaccines, T-cell transfer therapies and immune response checkpoint inhibitors may also be used to treat viral infections, both acute and chronic, by increasing CD8+ and/or CD4+ and/or similar T-cell numbers, and since GC4419 also increases CD8+ and/or CD4+ and/or similar T-cell numbers, it is believed that GC4419 and other pentaaza macrocyclic ring complexes may also be beneficial in increasing the anti-viral response to therapeutic vaccines, T cell transfer therapies and immune response checkpoint inhibitors and be useful for the treatment viral disease in which increasing the immune system response is effective for treatment.

Example 1

GC4419 was administered in combination with the T-cell checkpoint inhibitor anti-PD-1 (RMP1-14) to female Balb/C mice implanted with the mouse colon cancer cell line, Colon 26 beginning on day 3 post-implantation. Tumors were allowed to grow for up to 52 days or until they exceeded 1000 mm3.

Treatments with the antibody and GC4419 are described in Table 1.

TABLE 1

| | | Dosing Regimen for Colon 26 Syngeneic Tumor Model | | | | | | | |
|---|---|---|---|---|---|---|---|---|---|
| Group | n | Treatment Regimen 1 Agent | mg/kg | Route | Schedule | Treatment Regimen 2 Agent | mg/kg | Route | Schedule |
| 1 | 10 | vehicle | — | ip | bid × 21 (start on day 3) | — | — | — | — |
| 2 | 10 | GC4419 | 10 | ip | bid × 21 (start on day 3) | — | — | — | — |
| 3 | 10 | anti-PD1 RMP1-14 | 5 | ip | biwk × 2 (start on day 3) | — | — | — | — |
| 4 | 10 | GC4419 | 1 | ip | bid × 21 (start on day 3) | anti-PD1 RMP1-14 | 5 | ip | biwk × 2 (start on day 3) |
| 5 | 10 | GC4419 | 3 | ip | bid × 21 (start on day 3) | anti-PD1 RMP1-14 | 5 | ip | biwk × 2 (start on day 3) |
| 6 | 10 | GC4419 | 10 | ip | bid × 21 (start on day 3) | anti-PD1 RMP1-14 | 5 | ip | biwk × 2 (start on day 3) |

Tumor volumes were assessed and median and mean values are shown in FIGS. 1 (Median Tumor Volumes in Colon 26 Model) and 2 (Mean Tumor Volumes in Colon 26 Model).

Anti-PD1 monoclonal antibody treatment caused a modest decrease in tumor growth, and the addition of 1 and 3 mg/kg bid GC4419 caused a further decrease.

Example 2

GC4419 was administered in combination with the T-cell checkpoint inhibitor anti-PDL-1 (10F.9G2) to female Balb/C mice implanted with the mouse colon cancer cell line CT26 beginning on day 3 post-implantation. Tumors were allowed to grow for 17 days post-implantation and then collected.

Treatments with the antibody and GC4419 are described in Table 2.

TABLE 2

Dosing Regimen for CT26 Syngeneic Model

| Group | N= | Treatment | Dose (mg/kg/inj) | Schedule (start Day 3) |
|---|---|---|---|---|
| 1 | 5 | Control | — | Days 3, 6, 10, 13 |
| 2 | 5 | Anti-PD-L1 (10F.9G2) | 10 | Days 3, 6, 10, 13 |
| 3 | 5 | GC4419 | 3 | gd × 14 |
| 4 | 5 | Anti-PD-L1 | 10 | Days 3, 6, 10, 13 |
|   |   | GC4419 | 10 | qd × 14 |
| 5 | 5 | Anti-PD-L1 | 10 | Days 3, 6, 10, 13 |
|   |   | GC4419 | 3 | gd × 14 |
| 6 | 5 | Anti-PD-L1 | 10 | Days 3, 6, 10, 13 |
|   |   | GC4419 | 1 | gd × 14 |

Figure 3A:
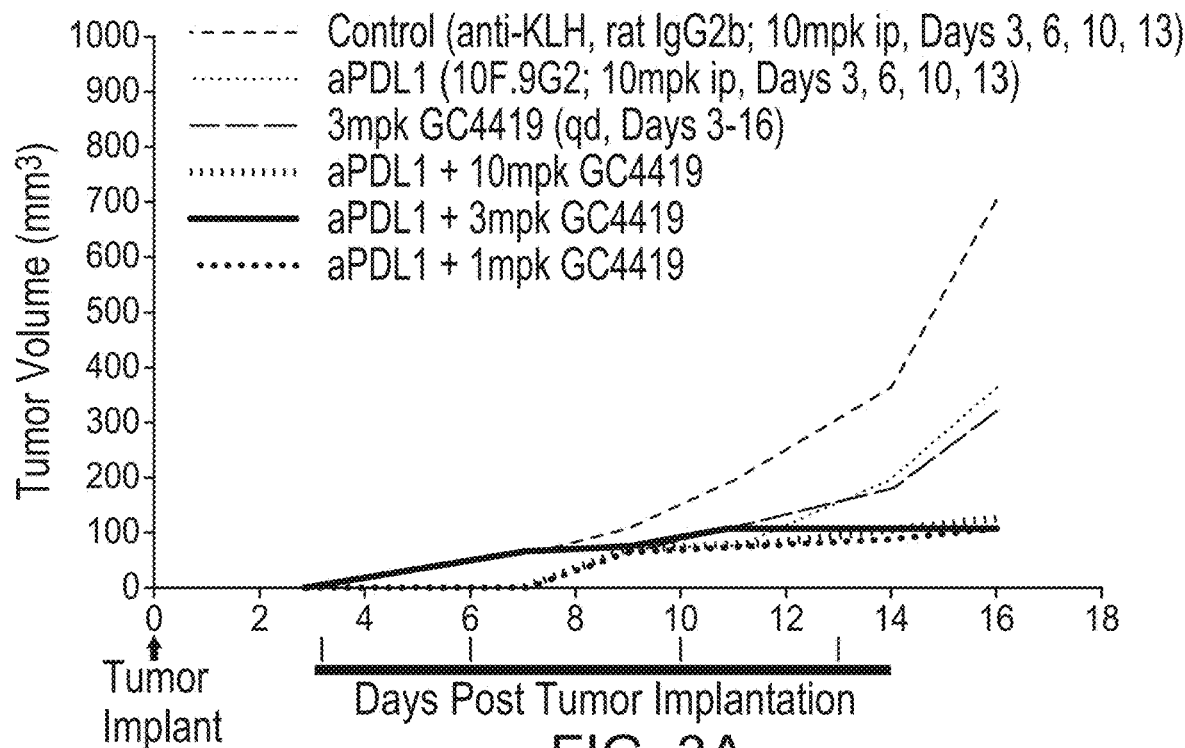
FIG. 3A shows median tumor volumes during treatment in a CT26 cancer model using GC4419 and anti-PDL1 through day 16 post-implantation.

The mice were sacrificed on day 17 for analysis of the tumor for tumor infiltrating leukocytes and other immunologic cells by flow cytommetry. The median tumor volumes are shown in FIG. 3A (Median Tumor Volume Through Day 16 Post-Implantation).

Figure 3B:
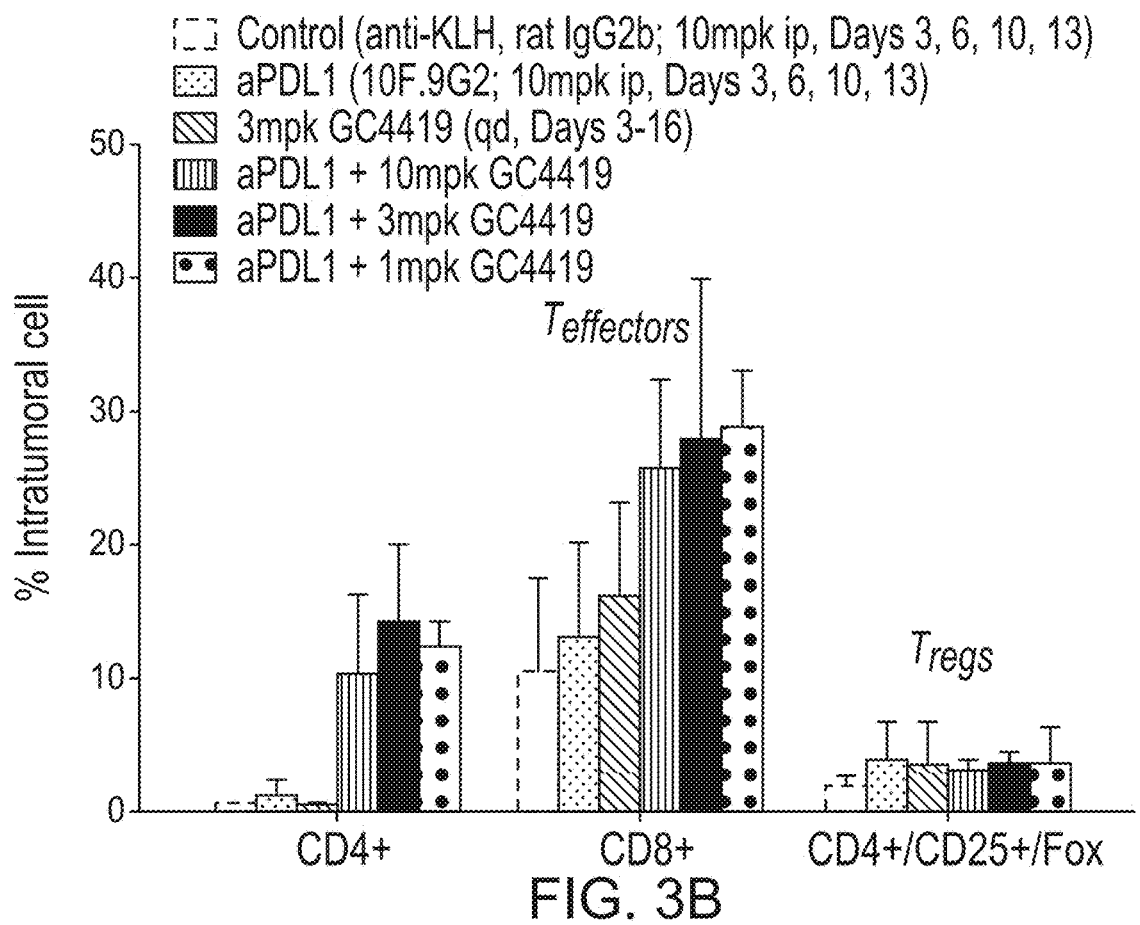
FIG. 3B depicts intratumoral leukocytes assessed by flow cytommetry for treatment in a CT26 cancer model using GC4419 and anti-PDL1.

To assess whether GC4419 was amplifying immune mediated tumor reduction, dissociated tumor cells were stained for markers of tumor infiltrating leukocytes and other immunologic cells, such as CD4+ (T helper class) and CD8+ (cytotoxic) T-cells, myeloid derived suppressor Cells (MDSC) and Treg cells, with the results shown in FIG. 3B (Intratumoral Leukocytes Assessed by Flow Cytommetry).

When administered together, GC4419 and anti-PDL-1 antibody significantly increased CD4+ and CD8+ T-cells (but not CD4+/CD25+/FoxP3+ T(regulatory) cells) as compared to either GC4419 or anti-PDL-1 antibody alone, consistent with the hypothesis that GC4419, either increased the recruitment, survival or proliferation of T-cells produced as a result of checkpoint inhibition and involved in mounting an effective immune response to tumors.

Example 3

GC4419 enhances anti-tumor response in animals treated with ionizing radiation (IR). It is also shown herein that in immune competent animal models, GC4419 enhances the anti-tumor immune response to IR. The findings also show that the radiation therapy is enhanced by providing GC4419, even when radiation therapy is being used in combination with the immune checkpoint inhibitor anti-CTLA4. Other findings have indicated that GC4419 is suitable as a normal tissue radiation protector, and the above findings thus indicate the added advantage of enhancing radiation therapy.

Figure 4A:
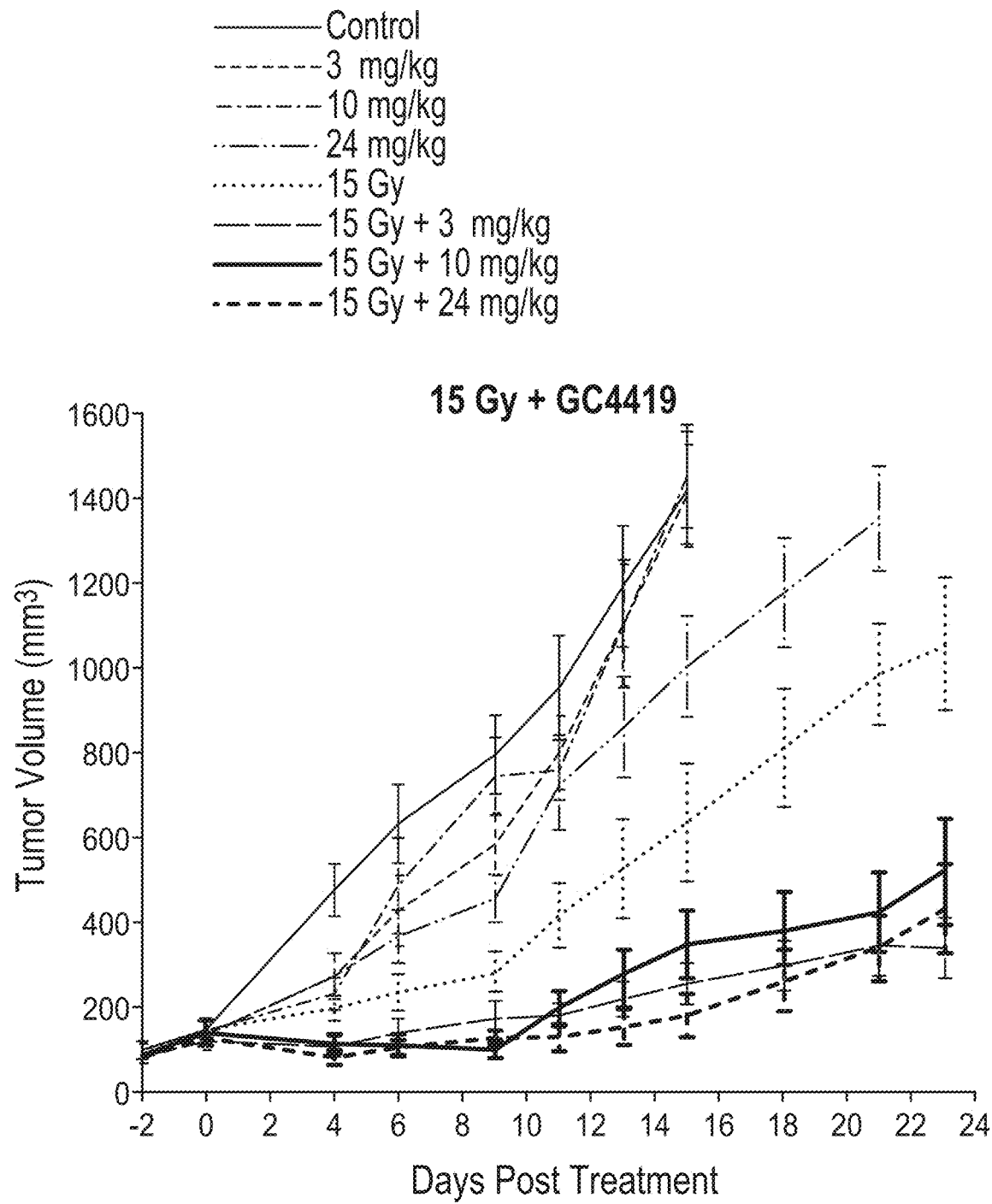
FIG. 4A shows average tumor volumes over a duration of treatment in a 4T1 breast metastatic cancer model with GC4419 in radiation therapy.
Figure 4B:
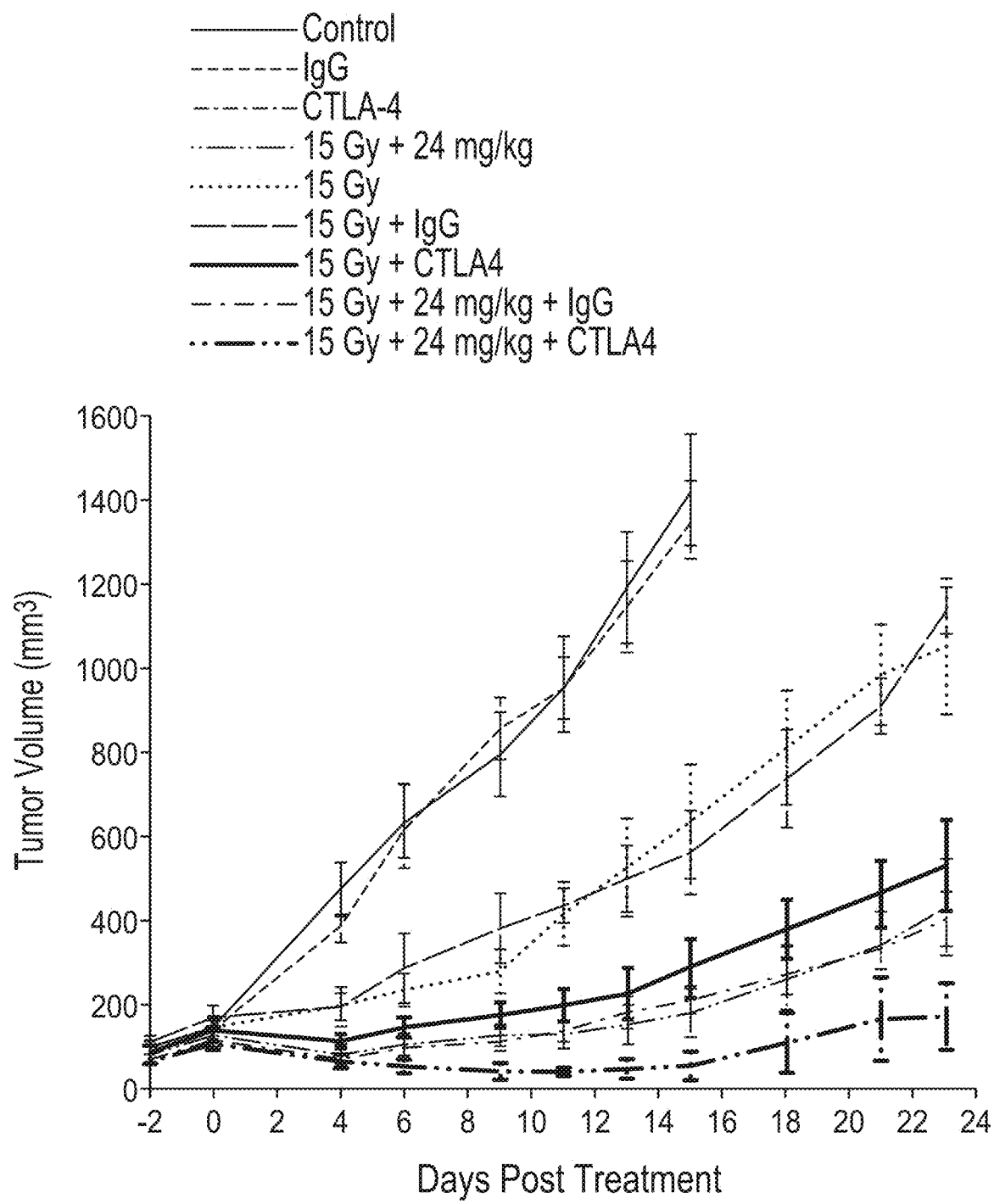
FIG. 4B shows average tumor volumes over a duration of treatment in a 4T1 metastatic breast cancer model with radiation therapy, GC4419 and anti-CTLA4.
Figure 4C:
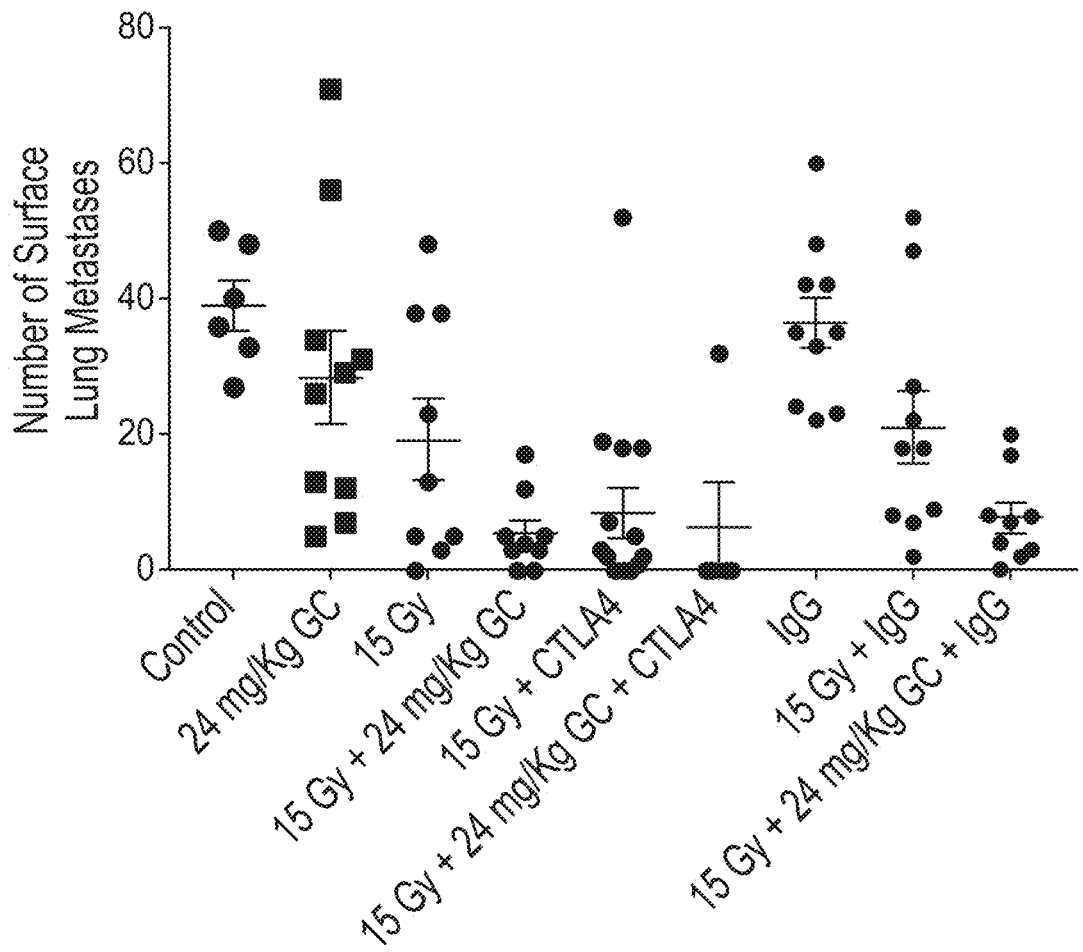
FIG. 4C shows a number of surface lung metastases for treatment in a 4T1 metastatic breast cancer model with radiation therapy, GC4419 and anti-CTLA4.

Specifically, as shown in FIGS. 4A-4C, GC4419 decreases metastasis and enhances the efficacy of the combination of radiation and T-cell checkpoint inhibitor anti-CTLA4 (9D9) in the 4T1 metastatic breast cancer model. Syngeneic animals were subcutaneously implanted with 4T1 cells to form a xenograft. On day 12, when no lung metastasis is present, animals were treated with GC4419 (24 mg/kg), 15 Gy of 250 kVp X-rays, and/or anti CTLA-4 antibodies (10 mg/kg) or IgG control antibodies, as described in Table 3 below. Tumor growth was tracked as a function of time and at day 35 post implantation (day 24 post start of treatment), animals were euthanized and lungs collected to count metastases.

TABLE 3

Dosing Regimen

| Group | n | Treatment (s) | Dose | Schedule |
|---|---|---|---|---|
| 1 | 10 | Control | 0 | D12, 13, 14, 15, 16 |
| 2 | 10 | GC4419 | 24 mg/kg | D12, 13, 14, 15, 16 |
| 3 | 10 | RT | 15 Gy | D12 × 1 |
| 4 | 10 | GC4419 | 24 mg/kg | D12, 13, 14, 15, 16 |
|   |   | RT | 15 Gy | D12 × 1 |
| 5 | 15 | Anti-CTLA4 (9D9) | 10 mg/kg | D10, 13, 16 |
|   |   | RT | 15 Gy | D12 × 1 |
| 6 | 5 | GC4419 | 24 mg/kg | D12, 13, 14, 15, 16 |
|   |   | Anti-CTLA4 (9D9) | 10 mg/kg | D10, 13, 16 |
|   |   | RT | 15 Gy | D12 × 1 |

GC4419 sensitized 4T1 tumors to radiation regardless of GC4419 dose (FIG. 4A), enhanced the efficacy of combination anti CTLA-4 therapy and radiation therapy (FIG. 4B), and significantly decreased the number of metastases (FIG. 4C).

Triple combination therapy of radiation, GC4419 and anti-CTLA-4, decreased the number of metastases per animal so much that it produced a significant number of animals without any lung metastases, as shown in Table 4 below.

TABLE 4

% Mice without lung metastases

| Treatment | % Mice without Lung Metastases |
|---|---|
| Control | 0 |
| GC4419 | 0 |
| RT | 11 |
| GC4419 + RT | 22 |
| aCTLA4 + RT | 25 |
| GC4419 + aCTLA4 + RT | 80 |

Accordingly, the results shown in FIGS. 4A-4C and Table 4 demonstrate that GC4419 can be used favorably in triple combination therapies with radiation treatment and cancer immune therapies such as immune checkpoint inhibitor treatment with anti-CTLA-4.

In separate studies, either syngeneic Balb/c mice or immunodeficient nu/nu mice were subcutaneously implanted with 4T1 cells to form a xenograft. On day 11 after transplant, animals were treated with GC4419 (24 mg/kg) and/or 15 Gy of 250 kVp X-rays, as described in Table 5 below.

TABLE 5

Dosing Regimen in nu/nu and Balb/c Mice

| | Group | n | Treatment (s) | Dose | Schedule |
|---|---|---|---|---|---|
| Balb/c Mice | 1 | 9 | Control | 0 | D11, 12, 13, 14, 15 |
| | 2 | 6 | GC4419 | 24 mg/kg | D11, 12, 13, 14, 15 |
| | 3 | 7 | RT | 15 Gy | D11 × 1 |
| | 4 | 6 | GC4419 RT | 24 mg/kg 15 Gy | D11, 12, 13, 14, 15 D11 × 1 |
| nu/nu Mice | 1 | 6 | Control | 0 | D11, 12, 13, 14, 15 |
| | 2 | 5 | GC4419 | 24 mg/kg | D11, 12, 13, 14, 15 |
| | 3 | 5 | RT | 15 Gy | D11 × 1 |
| | 4 | 5 | GC4419 RT | 24 mg/kg 15 Gy | D11, 12, 13, 14, 15 D11 × 1 |

Tumor volume was tracked as a function of time, and Day 17 (the last common day of measurement between the two studies given the rapid growth of tumors in the nu/nu mice) mean tumor volumes are described in Table 6 below. Additional measures such as Tumor Growth Delay and Tumor Doubling Time also showed similar trends.

TABLE 6

Mean Tumor Volume on Day 17

| | Group | Treatment (s) | Day 17 Tumor Volume, V | V(x)/V(Group 3) |
|---|---|---|---|---|
| Balb/c Mice | 1 | Control | 2263 mm$^3$ | 1.47 |
| | 2 | GC4419 | 1923 mm$^3$ | 1.25 |
| | 3 | RT | 1535 mm$^3$ | 1.00 |
| | 4 | GC4419 + RT | 673 mm$^3$ | 0.47 |
| nu/nu Mice | 1 | Control | All sac'd at Day 10 | |
| | 2 | GC4419 | All sac'd at Day 13 | |
| | 3 | RT | 1424 mm$^3$ | 1.00 |
| | 4 | GC4419 + RT | 902 mm$^3$ | 0.73 |

Both immunocompetent Balb/c mice and immunodeficient nu/nu mice treated with radiation alone showed reduced tumor growth after treatment and further tumor growth reduction was seen in both strains of mice treated with both radiation and GC4419. Further, this increase in response to combined radiation and GC4419 treatment was greater in immunocompetent mice than in immunodeficient mice, consistent with an immunologic role for GC4419 being at least part of this increased response.

Example 4

Figure 6A:
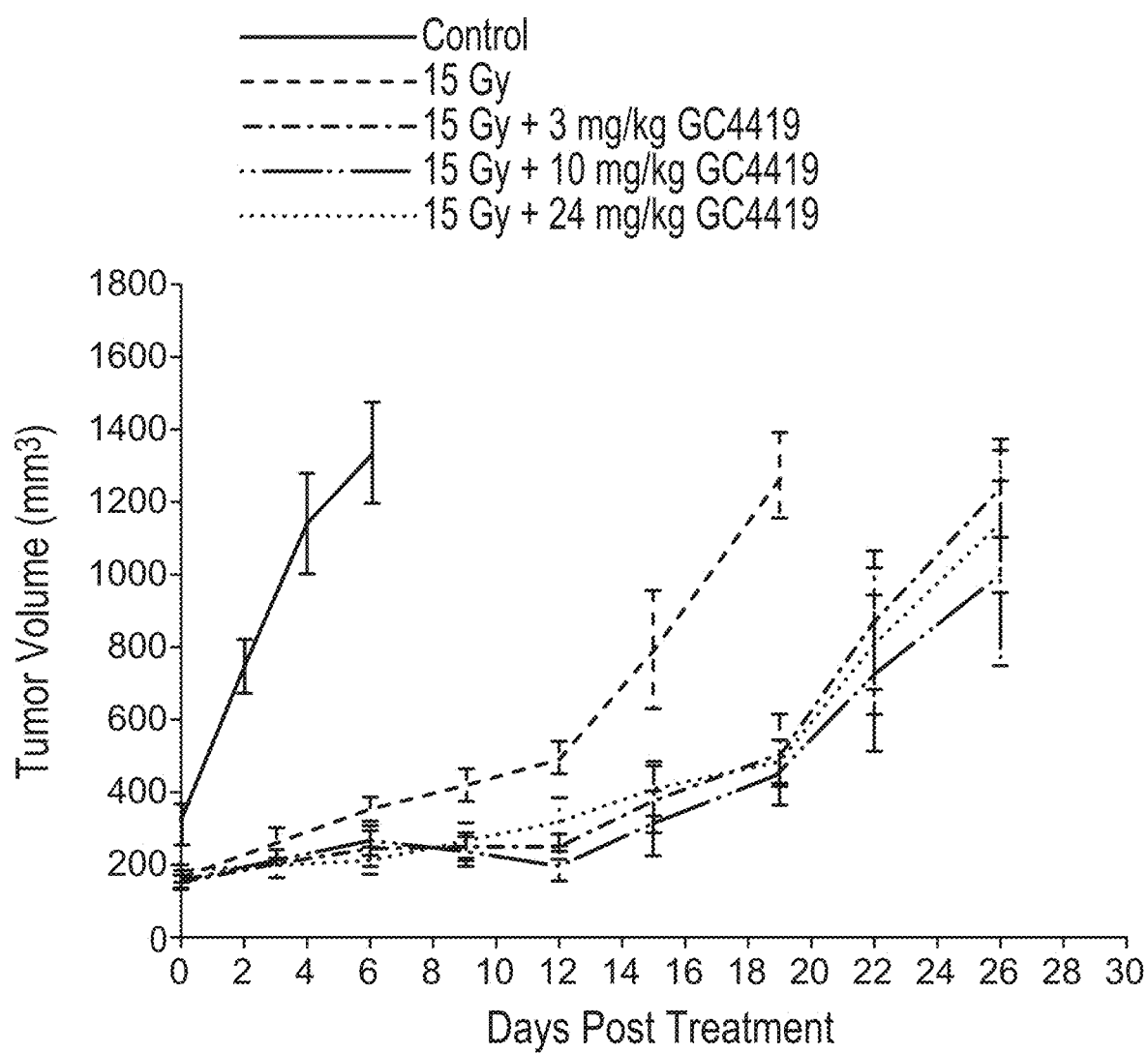
FIG. 6A shows the sensitizing effect of GC4419 on Lewis Lung Carcinoma tumors to ionizing radiation
Figure 6B:
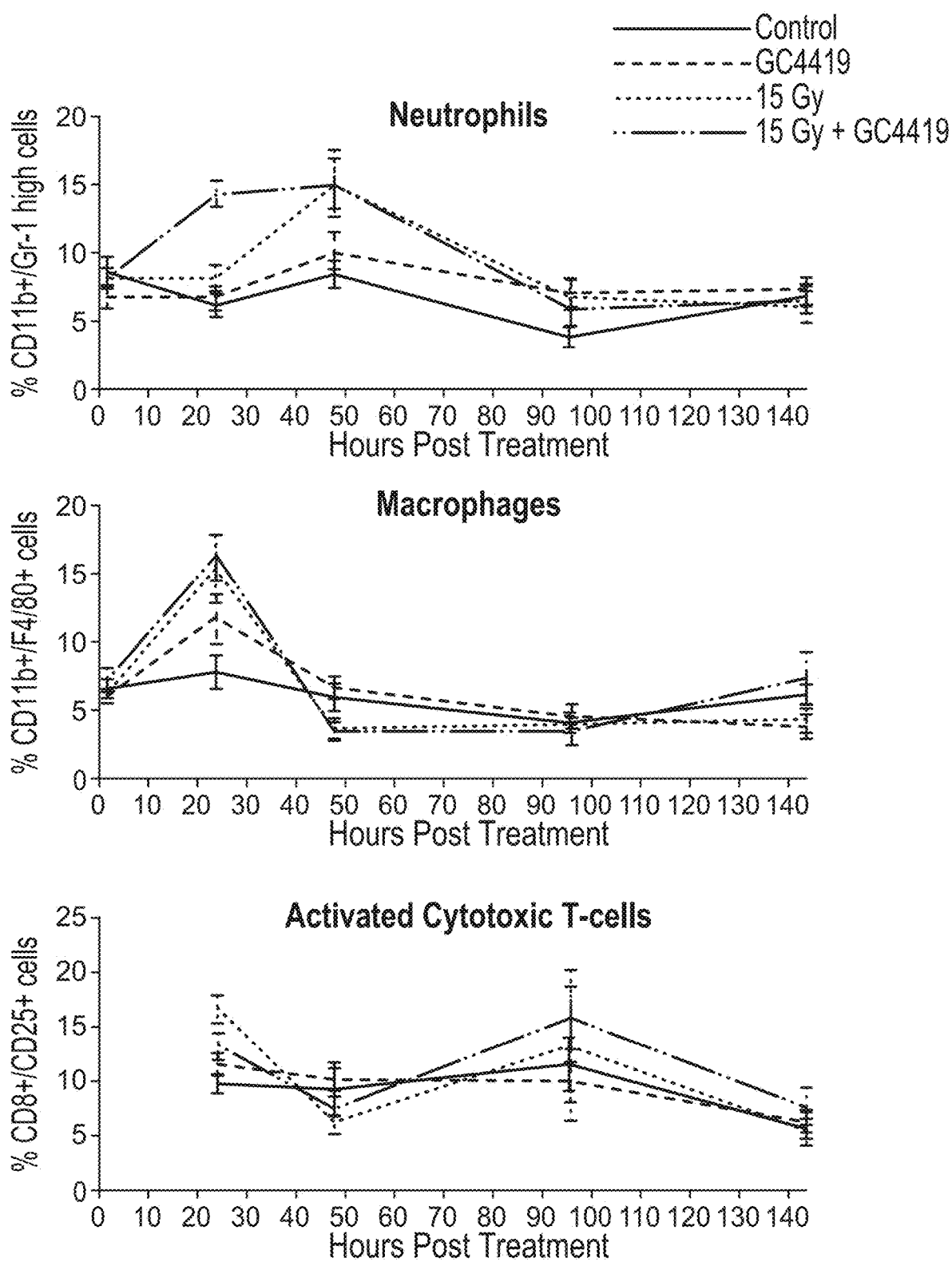
FIG. 6B shows changes in tumor infiltrating lymphocyte populations in Lewis Lung Carcinoma tumors post ionizing radiation and GC4419.

The effects of GC4419 plus IR on intratumoral levels of key immune cell populations were tested in Lewis lung carcinoma (LLC) tumors. In the study, 4 week old C57.CL/6 mice were injected with LLC cells to form tumors. At 13 days post-injection, animals were treated with GC4419 at doses of 3, 10 and 24 mg/kg and 15 Gy of 250 kVp X-rays. Tumor growth was tracked until tumor size exceeded 2 cm in any one direction. GC4419 sensitized tumors to ionizing radiation regardless of dose, as shown in FIG. 6A. In addition, tumor infiltrating lymphocyte populations were assessed in separate animals via flow cytometry at various time points post IR (15 Gy) in combination with 10 mg/kg GC4419 treatment. Intratumoral populations of neutrophils, macrophages and activated cytotoxic T-cells were altered due to the presence of GC4419 either with or without ionizing radiation, as shown in FIG. 6B. However, it is unclear from this study alone whether these transient alterations in the immune cell populations caused by GC4419 contribute to improved results for the combination of GC4419 with checkpoint inhibitor therapy combined or in the absence of radiation therapy.

Example 5

GC4419 was administered in combination with the T-cell checkpoint inhibitor anti-CTLA-4 (9D9) to female Balb/C mice implanted subcutaneously with the mouse breast cancer cell line, 4T1. Tumors were allowed to grow for up to 45 days or until they exceeded 3000 mm$^3$ (or Group mean of 2000 mm$^3$).

Treatments with the antibody and GC4419 are described in Table 7.

TABLE 7

Dosing Regimen for 4T1 Syngeneic Tumor Model

| Group | n | Treatment(s) | Dose (mg/kg) | Schedule |
|---|---|---|---|---|
| 1 | 10 | Vehicle (10 mM NaHCO3) | 0 | From D0; QD × 21 |
| 2 | 10 | GC4419 | 3 | From D0; QD × 21 |
| 3 | 10 | Anti-CTLA4 (9D9) | 10 | BiW × 3 wk |
| 4 | 10 | Anti-CTLA4 (9D9) GC4419 | 10 3 | BiW × 3 wk From D0; QD × 21 |
| 5 | 10 | Anti-CTLA4 (9D9) GC4419 | 10 3 | BiW × 3 wk From D3; QD × 21 |
| 6 | 10 | Anti-CTLA4 (9D9) GC4419 | 10 3 | BiW × 3 wk From D6; QD × 21 |

Figure 5A:
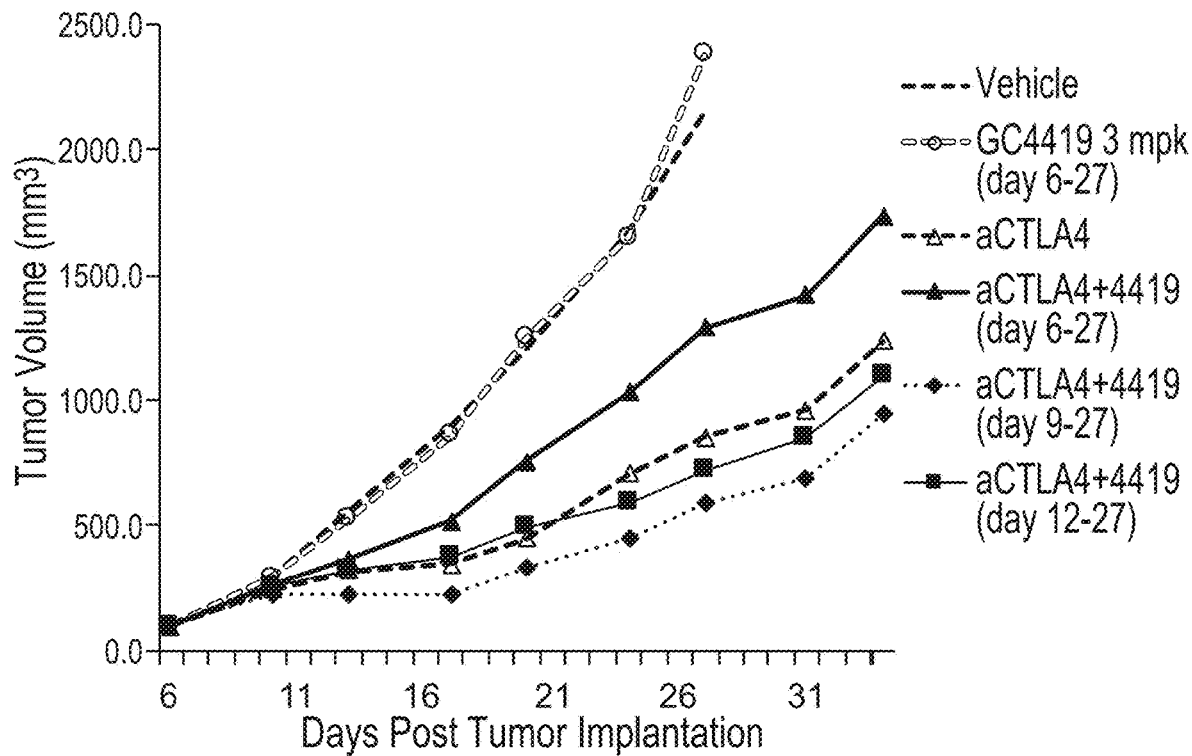
FIG. 5A shows mean tumor volumes over a duration of treatment in a 4T1 metastatic breast cancer model with GC4419 and anti-CTLA4.

Tumor volumes were assessed and mean values are shown in FIG. 5A (Mean Tumor Volumes in 4T1 Model).

Anti-CTLA4 monoclonal antibody treatment caused a significant decrease in tumor growth, and the addition of 3 mg/kg GC4419 started at least 3 days after antibody treatment caused a further decrease.

Notably, the results depicted for treatment with anti-CTLA4 alone are somewhat inconsistent with prior experience with this therapy, as the tumor growth decrease with anti-CTLA4 alone was somewhat higher than prior experience, and was also higher than in other arms with anti-CTLA4 up until the point where GC4419 was added. In addition, the tumor growth decrease as compared to control when treating with anti-CTLA4 alone appeared to be improved even over a combination therapy with GC4419 where started on the same day as anti-CTLA4 treatment onset. This is despite the fact that combination of GC4419 with other checkpoint inhibitors, such as the anti-PD1 and anti-PDL1 therapies described above, demonstrate improved results when combined with GC4419 even for a same day start (or even the day prior). Accordingly, it is believed that the magnitude of this particular result for anti-CTLA4 treatment alone may be somewhat anomalous, and while not wishing to be limited by any theory, it is believed that treatment in combination with GC4419 provides good results over anti-CTLA4 alone, even for a same day start. Nonetheless, the results clearly demonstrate that the combination of GC4419 with anti-CTLA4 provided improved results over anti-CTLA4 alone, when a start of GC4419 treatment is delayed after the anti-CTLA4 treatment onset to a start on day 3 or day 6 after the first day of anti-CTLA4 treatment. That is, delaying the start of administration of GC4419, such as until day 3 or day 6, or even day 10 or day 13 after a start of anti-CTLA4 administration (such as, in this example until a day following the second, third, fourth or even fifth anti-CTLA4 dose), significantly improves treatment over anti-CTLA4 alone, as well as over a same-day start combination of anti-CTLA4 with GC4419.

Figure 5B:
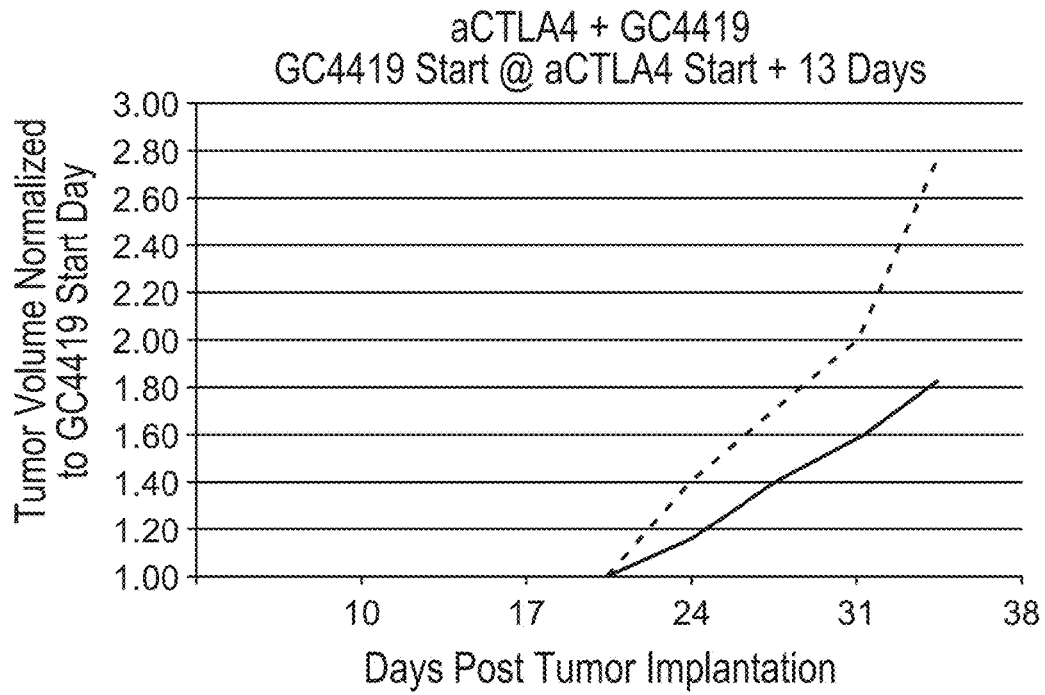
FIG. 5B shows normalized mean tumor volumes for treatment in a 4T1 metastatic breast cancer model with GC4419 and anti-CTLA4, where the GC4419 start date is day 13 after the initial anti-CTLA4 treatment.

FIG. 5B depicts such an improvement occurring for dosing of GC4419 that is delayed until day 13 after a start of anti-CTLA4 administration (i.e., after the 5$^{th}$ dose of anti-CTLA4). In comparison of arms treated with (a) combination of GC4419 with anti-CTLA4 treatment and (b) anti-CTLA4 treatment alone, no difference should be apparent between the two arms before addition of GC4419 treatment. As a result tumor control was assessed by normalizing the tumor growth curves of each arm with respect to the day on which treatment with GC4419 was started in the combination arm (i.e., day 13 in FIG. 5B). Such analysis shows the reduced tumor growth occurring after addition of GC4419 treatment as compared to anti-CTLA4 alone.

Accordingly, FIGS. 5A and 5B demonstrate the improved results in terms of tumor growth decrease that can be achieved with combinations of anti-CTLA4 and GC4419, including in dosing regimens where dosing with GC4419 is delayed for a period of time after dosing with anti-CTLA4 has begun, such as 3 to 6 days, and even 10 to 13 days after an anti-CTLA4 treatment onset (such as after the second, third or even fourth anti-CTLA4 dose).

Example 6

GC4419 was administered in combination with the T-cell checkpoint inhibitor anti-CTLA-4(9D9) to female Balb/mice implanted subcutaneously with the mouse breast cancer cell line, 4T1. Tumors were allowed to grow for up to 35 days or until they exceeded 3000 mm$^3$ (or Group mean of 2000 mm).

Treatments with the antibody and GC4419 are described in Table 8.

TABLE 8

Dosing Regimen for 4T1 Syngeneic Model

| Group | N | Treatment | Dose (mg/kg) | Dosing days | Schedule |
|---|---|---|---|---|---|
| 1 | 10 | Vehicle (10 mM NaHCO$_3$) | 0 | day 4~21 | QD |
| 2 | 10 | GC4419 | 10 | day 4~21 | QD |
| 3 | 10 | Anti-CTLA4 (9D9) | 10 | day 1, 4, 8, 11, 15, 18 | BIW × 3 weeks |
| 4 | 10 | Anti-CTLA4 (9D9) | 10 | day 1, 4, 8, 11, 15, 18 | BIW × 3 weeks |
|   |   | GC4419 | 10 | day 4~21 | QD |
| 5 | 10 | Anti-CTLA4 (9D9) | 10 | day 1, 4, 8, 11, 15, 18 | BIW × 3 weeks |
|   |   | GC4419 or | 3 | day 5, 6, 7, 9, 10, 12, 13, 14, 16, 17, 19, 20, 21 | QD |
|   |   | Vehicle (10 mM NaHCO$_3$) | 0 | day 4, 8, 11, 15, 18 | QD |
| 6 | 10 | Anti-CTLA4 (9D9) | 10 | day 1, 4, 8, 11, 15, 18 | BIW × 3 weeks |
|   |   | GC4419 or | 10 | day 5, 6, 7, 9, 10, 12, 13, 14, 16, 17, 19, 20, 21 | QD |
|   |   | Vehicle (10 mM NaHCO$_3$) | 0 | day 4, 8, 11, 15, 18 | QD |

Figure 5C:
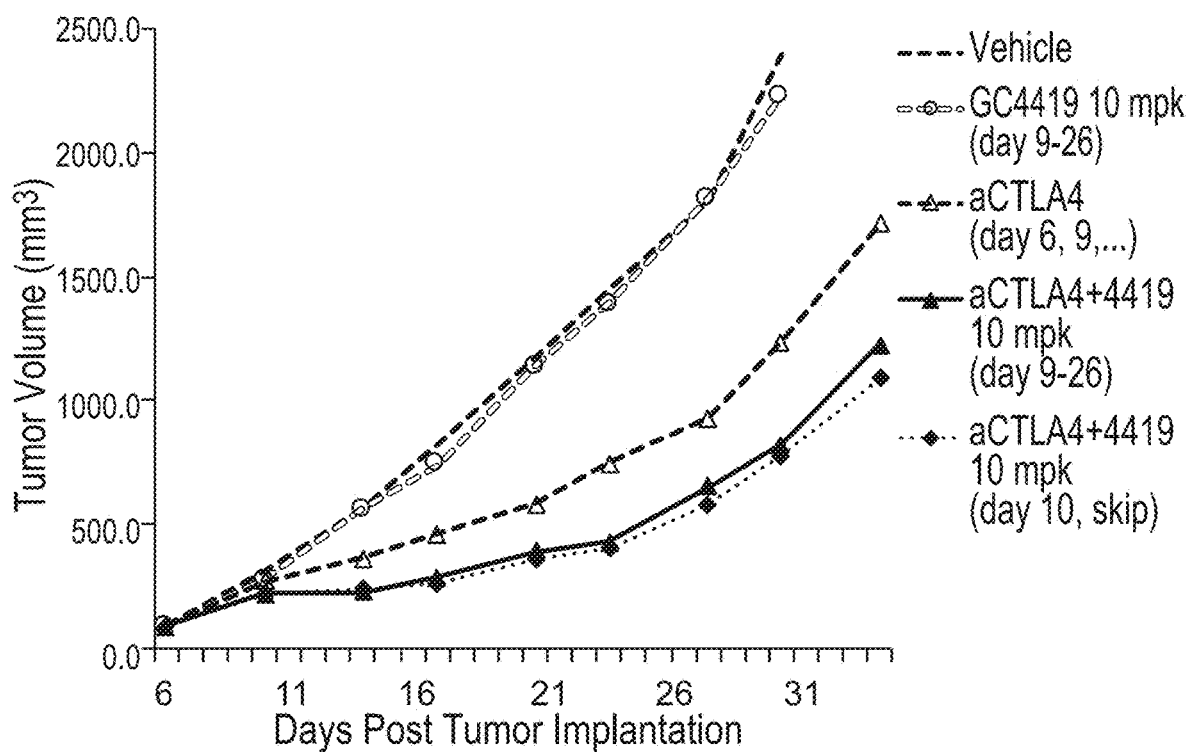
FIGS. 5C-5D show mean tumor volumes over a duration of treatment in a 4T1 metastatic breast cancer model with GC4419 and anti-CTLA4.
Figure 5D:
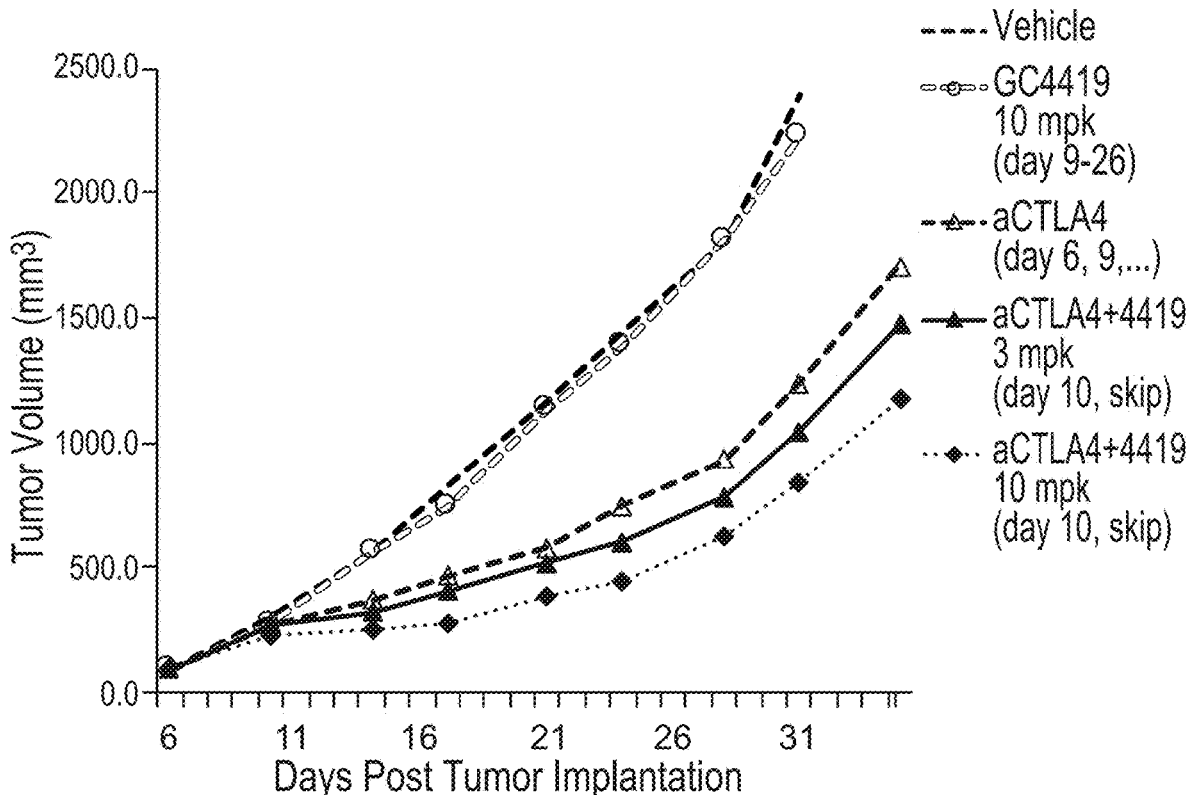

Tumor volumes were assessed and mean values are shown in FIGS. 5C and 5D (Mean Tumor Volumes in 4T1 Model).

FIG. 5C shows that the combination of anti-CTLA4 with GC4419 provided improved results in terms of decreased tumor volume both when administration of GC4419 started 3 days (day 9-26) and 4 days (day 10) following anti-CTLA administration onset, over anti-CTLA4 treatment alone. FIG. 5C further shows that skipping administration of GC4419 on those days when anti-CTLA4 was administered (day 10, skip) further improved the results, albeit slightly. FIG. 5D further demonstrates that delaying administration of GC4419 until 4 days (day 10) after the first anti-CTLA4 administration provides improved results over anti-CTLA4 administration alone, including when administration of GC4419 is skipped on those days when anti-CTLA4 is administered. Also, the increased dose of 10 mg/kg of GC4419 provides improved results over a dose of 3 mg/kg, although significant improvements in treatment as compared to anti-CTLA4 alone are seen with both dose levels.

Accordingly, while anti-CTLA4 monoclonal antibody treatment caused a significant decrease in tumor growth, the addition of 3 mg/kg or 10 mg/kg GC4419, particularly when started at least 3 days after antibody treatment, caused a significant further decrease in tumor volumes, and skipping GC4419 administration on those days when anti-CTLA4 was administered further improved the results.

Example 7

In this example, the effects of treatment with GC4419 in combination with the immune checkpoint inhibitor anti-PD-1 (RMP1-14) were tested. 4T1 mouse breast cancer tumors were implanted subcutaneously in female mice. Dosing with controls, GC4419 and the anti-PD-1 antibodies was started on day 7, except where dosing with GC4419 was begun on day 6 or day 10, and continued until the time point as indicated in Table 9 below. Tumor volumes were measured approximately every 3 days through day 16.

TABLE 9

| Group | N | Treatment | Dose (mg/kg) | Planned Dosing Schedule/Days |
|---|---|---|---|---|
| Group-1 | 10 | Vehicle (10 mM NaHCO$_3$) | 10 | QD × 3 weeks |
| Group-2 | 10 | GC4419 | 10 | QD × 3 weeks (start 1 day before first anti-PD-1; Day 6) |
| Group-3 | 10 | Anti-PD-1 (RMP1-14) | 10 | BIW × 3 weeks (start day 7) |
| Group-4 | 10 | GC4419 | 10 | QD × 3 weeks (start 1 day before first anti-PD-1) |
|   |   | Anti-PD-1 (RMP1-14) | 10 | BIW × 3 weeks |
| Group-5 | 10 | GC4419 | 10 | QD × 3 weeks (start 3 days post first anti-PD-1) |
|   |   | Anti-PD-1 (RMP1-14) | 10 | BIW × 3 weeks |

Figure 7:
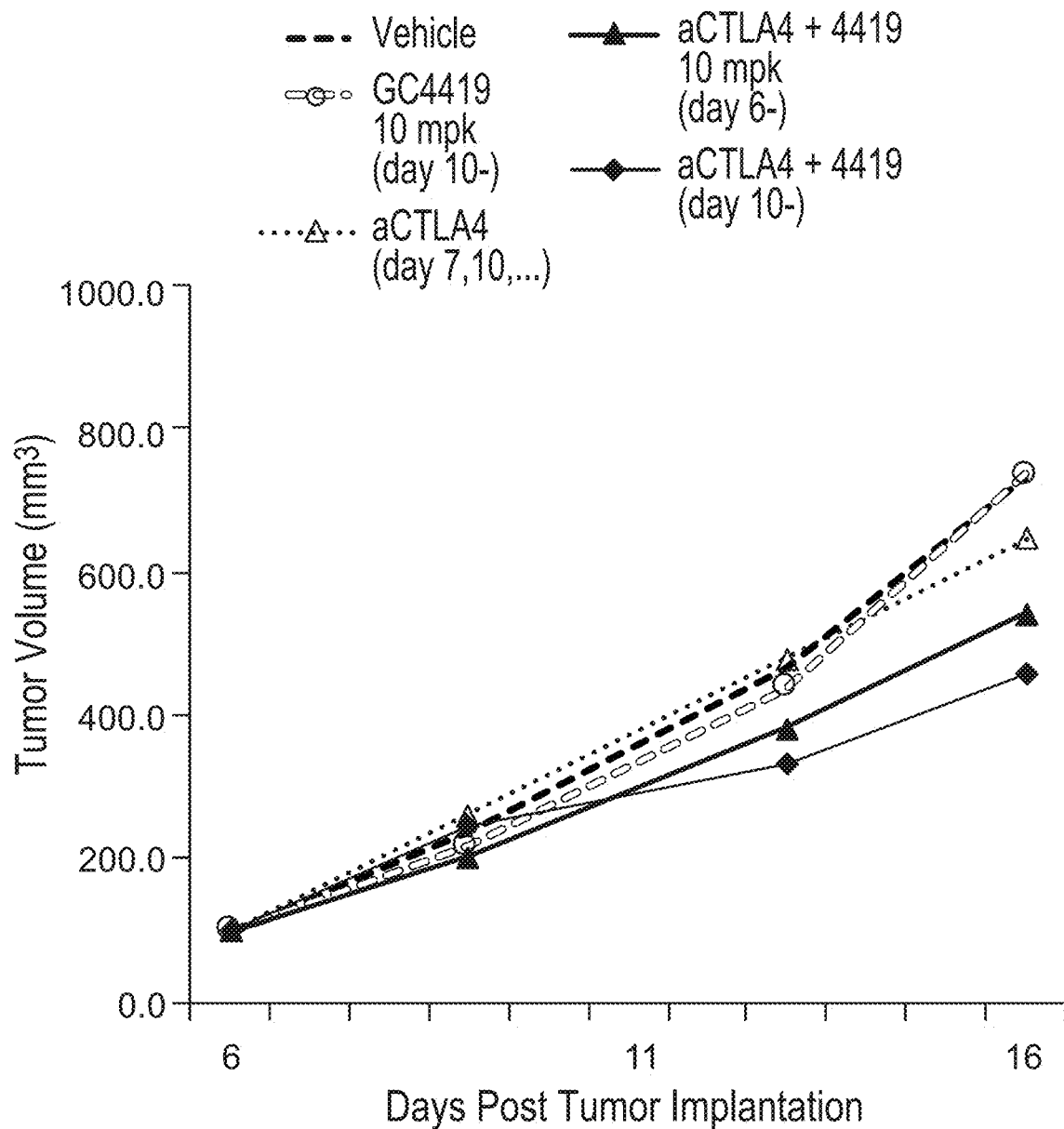
FIG. 7 shows mean tumor volumes over a duration of treatment in a 4T1 metastatic breast cancer model with GC4419 and anti-PD-1.
Figure 8A:
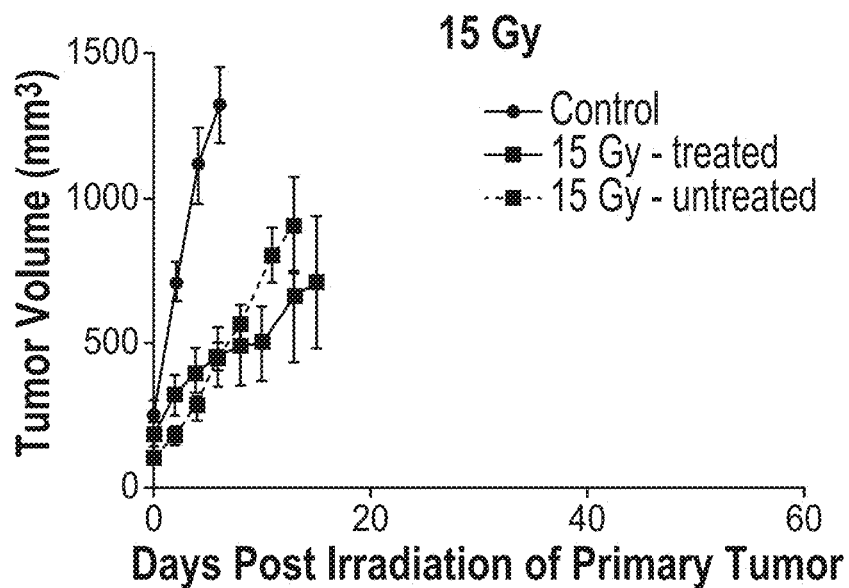
FIGS. 8A-8E show tumor volumes for an abscopal study.
Figure 8B:
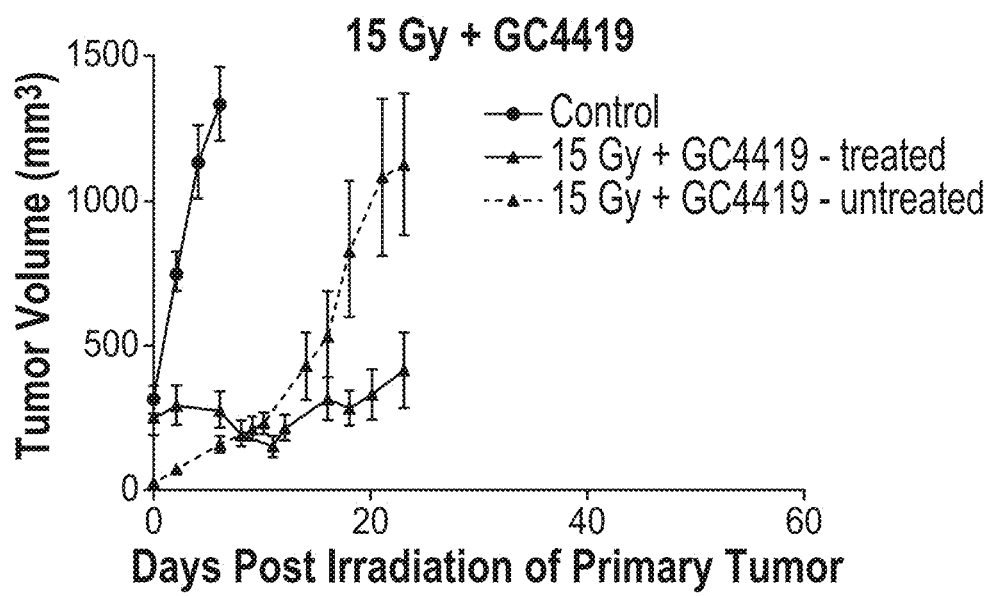
Figure 8C:
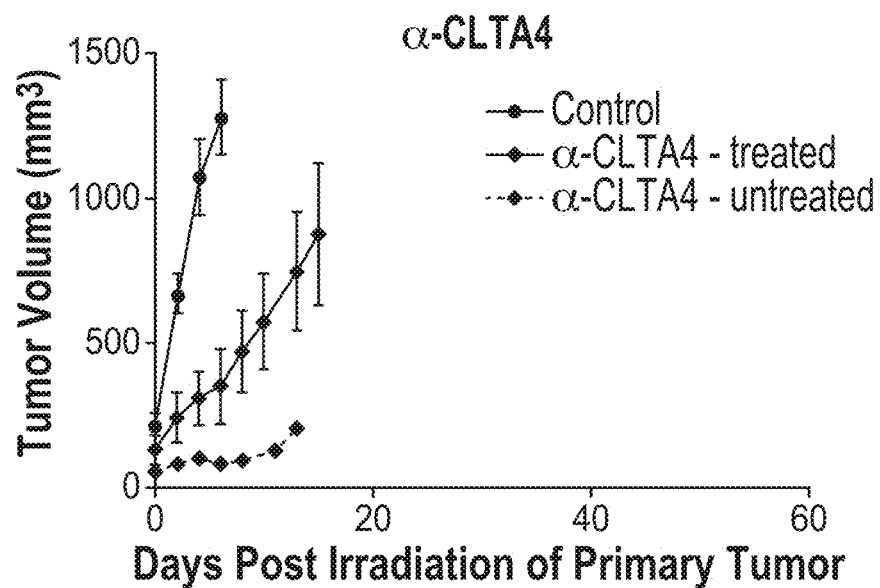
Figure 8D:
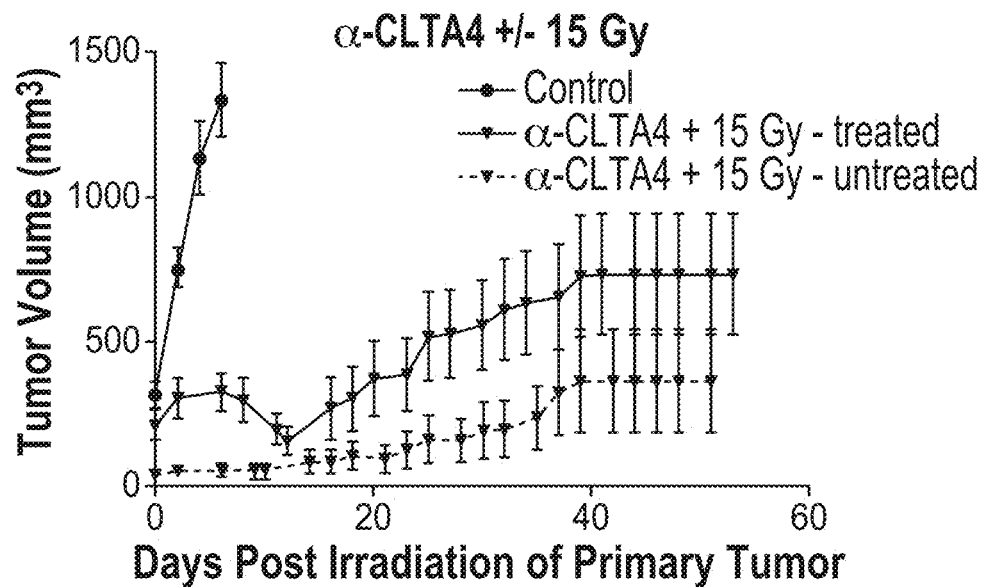
Figure 8E:
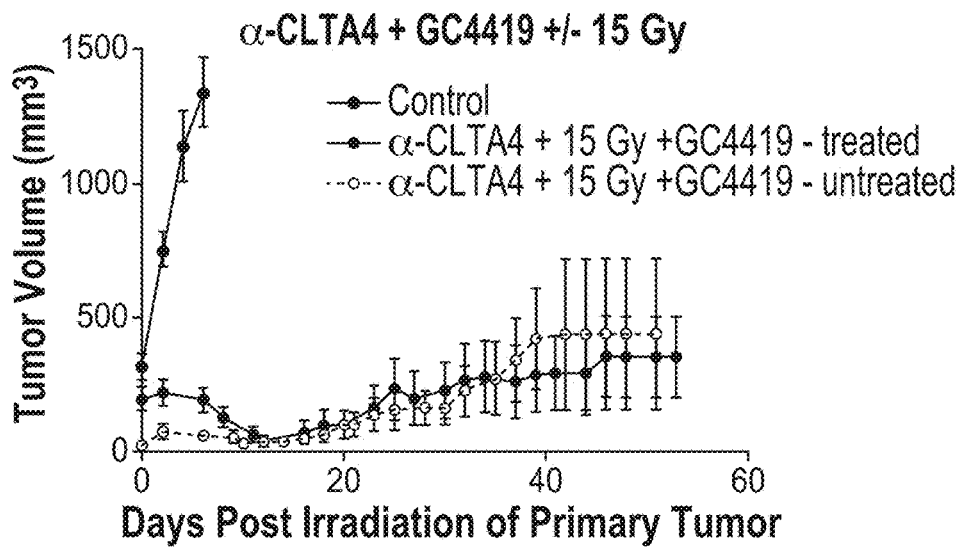
Figure 9:
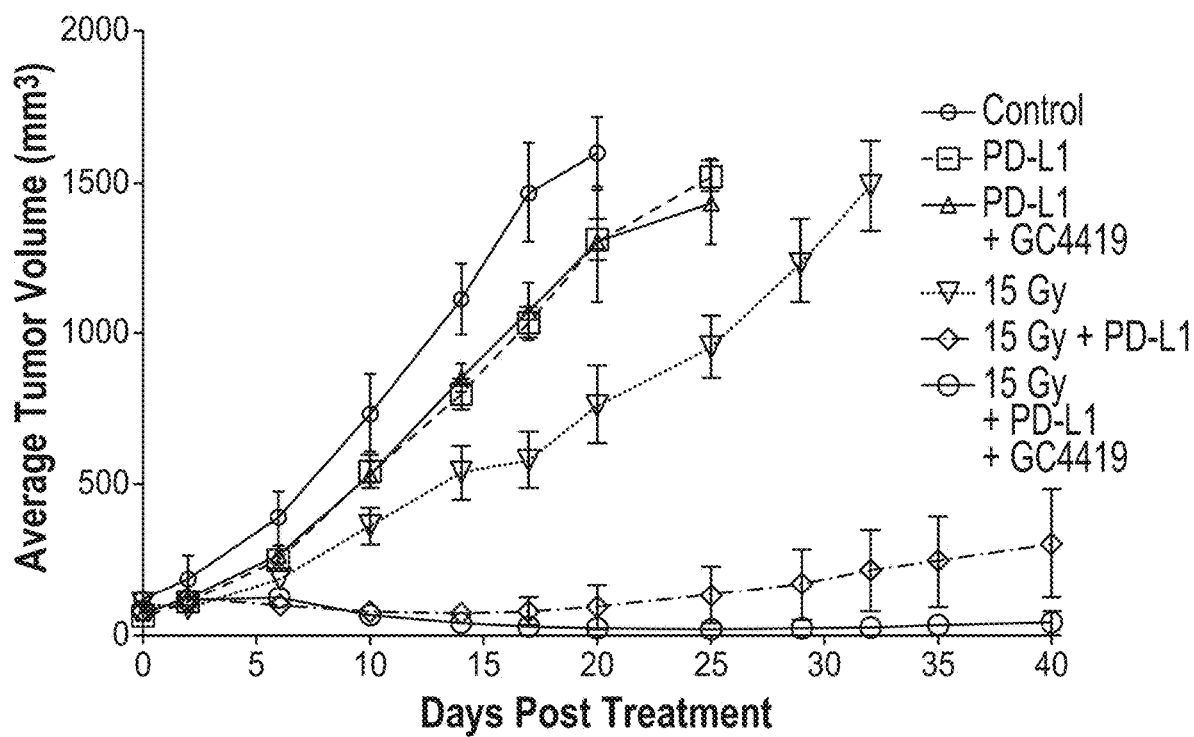
FIG. 9 shows average tumor volumes over a duration of treatment with GC4419 and anti-PDL-1.
Figure 10A:
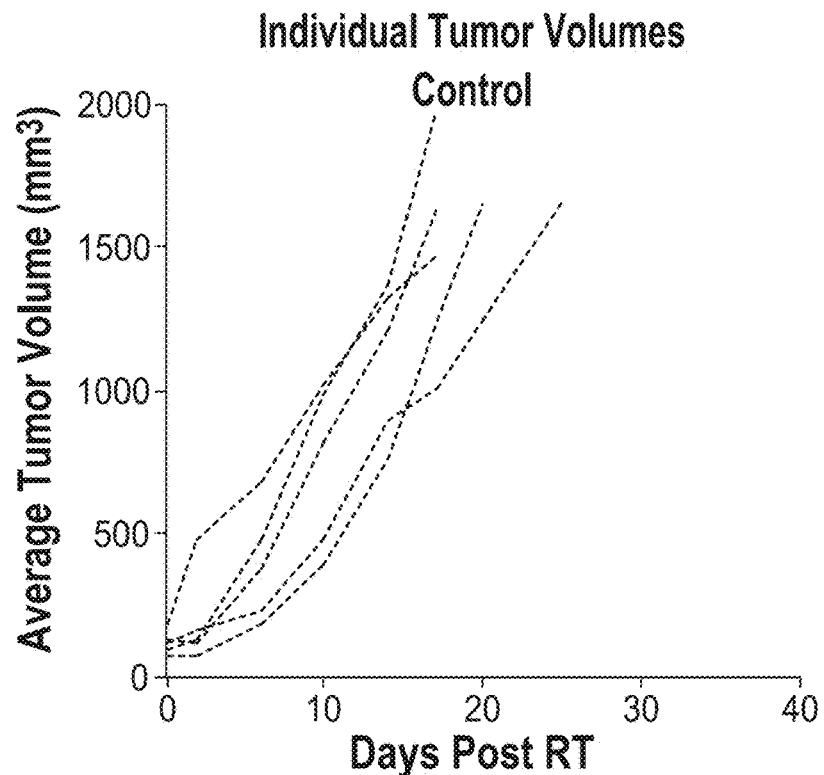
FIGS. 10A-10E show individual tumor volumes over a duration of treatment with GC4419 and anti-PDL-1
Figure 10B:
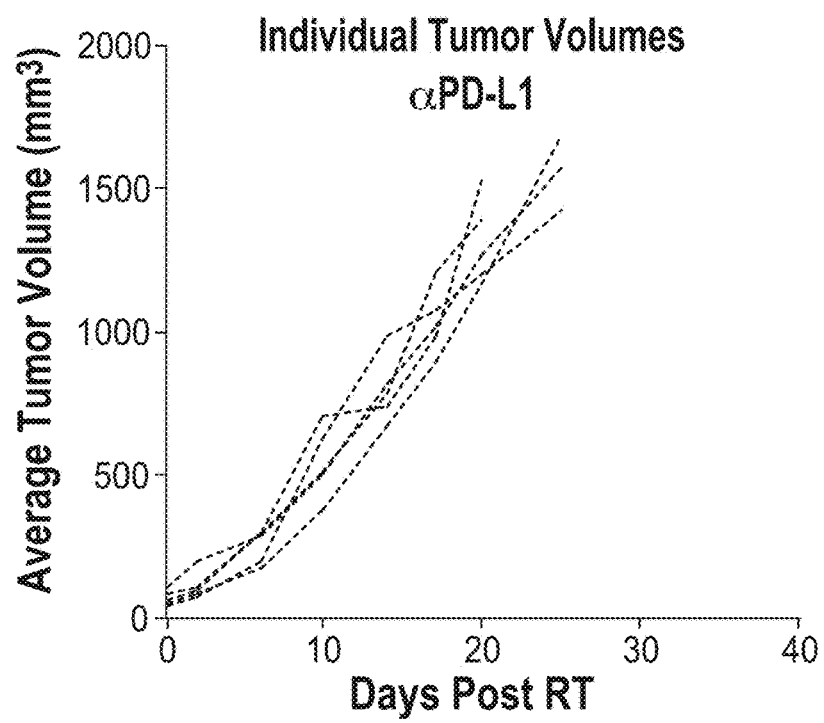
Figure 10C:
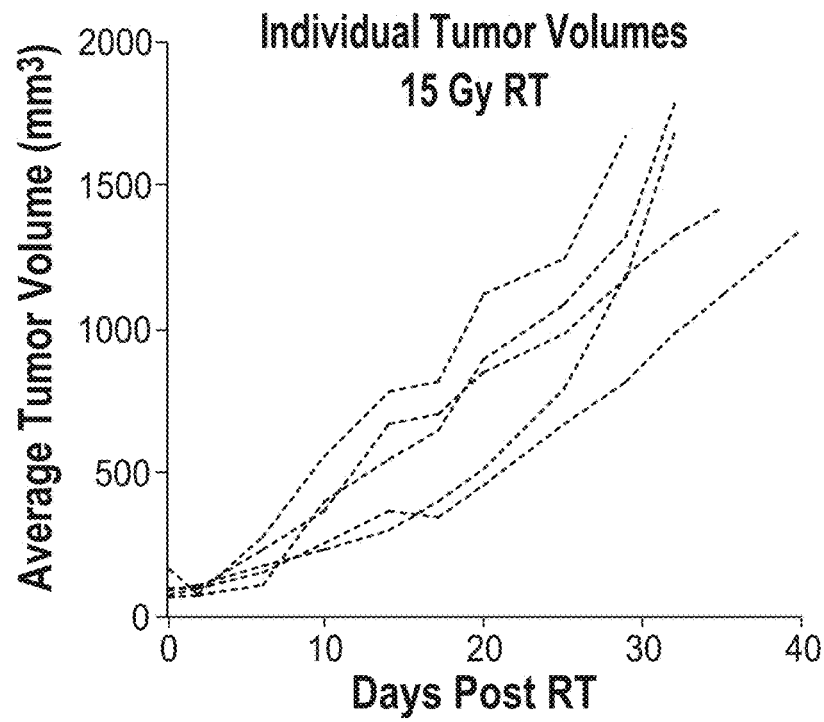
Figure 10D:
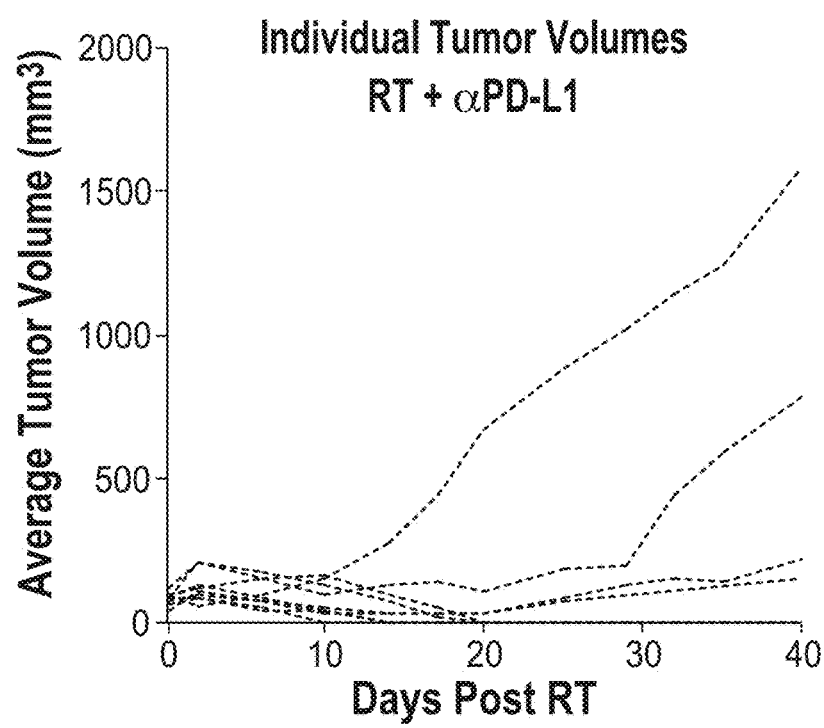
Figure 10E:
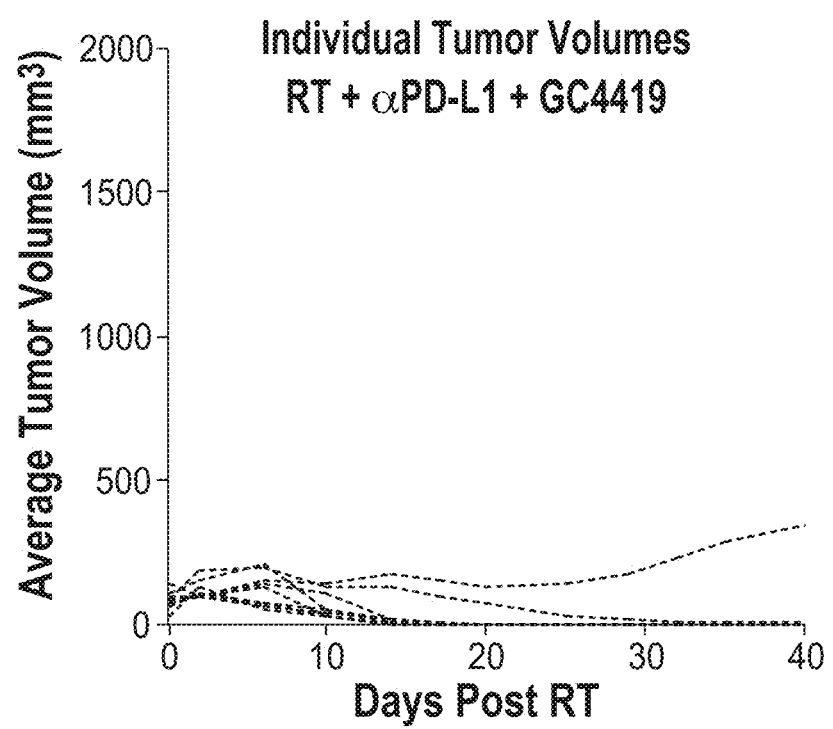

FIG. 7 shows the result on mean tumor volume for the treatment regimens in Table 9 above. The Group 5 combination of anti-PD-1 antibody and GC4419 (started 3 days after first antibody injection) was the most effective in slowing 4T1 growth. However, the Group 4 combination of anti-PD-1 antibody and GC4419 started 1 day before the first anti-PD-1 treatment also provided good results. Accordingly, while not wishing to be limited by any theory, it is believed that treatment with the combination of GC4419 and anti-PD-1 provides good results over anti-PD-1 alone, even for a same day start, as good results are shown for both delaying administration of GC4419 after the anti-PD-1 start (such as 3 days as in Group 5), and for administration closer to the start of anti-PD-1 (e.g., on the day before administration as in Group 4), although the results further appear to show that delaying administration of GC4419 after the start of anti-PD-1 administration can provide improvements over administration closer to the start of anti-PD-1 administration (e.g., compare Group 5 and Group 4).

Example 8

Similar to the findings in Example 3, another experiment also showed that the radiation therapy is enhanced by providing GC4419, even when radiation therapy is being used in combination with the immune checkpoint inhibitor anti-CTLA4.

Specifically, as shown in FIGS. 8A-8E, GC4419 enhanced the efficacy of the combination of radiation and T-cell checkpoint inhibitor anti-CTLA4 (9D9) in the LLC squamous cell carcinoma breast cancer model. In addition to enhancing efficacy against the irradiated primary tumor implanted in one flank of the animal, GC4419 also enhanced efficacy against an unirradiated second tumor implanted in the opposite flank.

Syngeneic animals (C57Bl/6 mice) were subcutaneously implanted with LLC cells in the right flank to form a xenograft (primary tumor). On day 2, the same animals were subcutaneously implanted with LLC cells in the left flank for form another xenograft (secondary tumor). On day 8, some animals began treatment with anti CTLA-4 antibodies (200 µg) as indicated below. On day 11, when both primary and secondary tumors were palpable, all animals were treated with GC4419 (24 mg/kg), 15 Gy of 250 kVp X-rays, and/or anti CTLA-4 antibodies (10 mg/kg), as described in Table 10 below. Tumor growth was tracked as a function of time for both primary and secondary tumors.

TABLE 10

Dosing Regimen

| Group | n | Treatment (s) | Dose | Schedule |
|---|---|---|---|---|
| 1 | 10 | Control | 0 | D11, 12, 13, 14, 15 |
| 2 | 10 | RT | 15 Gy | D11 × 1 |
| 3 | 10 | GC4419 | 10 mg/kg | D11, 12, 13, 14, 15 |
|   |   | RT | 15 Gy | D11 × 1 |
| 4 | 10 | Anti-CTLA4 (9D9) | 200 µg | D8, 11, 13 |
|   |   | RT | 15 Gy | D11 × 1 |
| 5 | 9 | GC4419 | 10 mg/kg | D11, 12, 13, 14, 15 |
|   |   | Anti-CTLA4 (9D9) | 200 µg | D8, 11, 13 |
|   |   | RT | 15 Gy | D11 × 1 |

GC4419 sensitized primary and secondary tumors to radiation and primary tumors to the combination of anti CTLA-4 therapy and radiation therapy, delaying their growth (FIGS. 8A-8E). It also appeared to enhance the efficacy of the combination of anti CTLA-4 therapy and radiation therapy against secondary tumors, increasing the number of animals whose secondary tumors either stopped growing or disappeared at Day 73 post-implantation as described in Table 11 below.

TABLE 11

Secondary Tumor Responses at Day 73

| Group | n | Treatment (s) | Complete Response + Stable Disease, n |
|---|---|---|---|
| 1 | 10 | Control | 0 |
| 2 | 10 | RT | 0 |
| 3 | 10 | GC4419 + RT | 0 |
| 4 | 10 | Anti-CTLA4 + RT | 3 |
| 5 | 9 | GC4419 + RT + Anti-CTLA4 | 6 |

The occasional ability of radiation treatment of one or more targeted tumors to produce an anti-tumor response in a distant unirradiated tumors is commonly known as the "abscopal" effect. This abscopal effect is widely believed due to a radiation-induced immune response against the unirradiated tumors. The combination of immunotherapy, such as anti CTLA4 therapy, and radiation therapy has been shown to increase the number of such abscopal effects. In the study described here the combination of anti CTLA-4 therapy and radiation therapy both slowed the growth of the unirradiated secondary tumors (FIG. 8D) and generated apparent long-term responses (stable disease or better) in secondary tumors in some animals. Addition of GC4419 to the combination of anti CTLA-4 therapy and radiation therapy also slowed the growth of secondary tumors (FIG. 8E) and resulted in a greater number of long-term responses (Table 11).

Accordingly, the results shown in FIGS. 8A-8E and Table 11 demonstrate that GC4419 can be used favorably in triple combination therapies with radiation treatment and cancer immune therapies such as immune checkpoint inhibitor treatment with anti-CTLA-4, to both increase efficacy in irradiated tumors and potentially generate efficacy in unirradiated tumors.

Example 9

Similar to the findings in Examples 3 and 8, another experiment showed that GC4419 enhances the combination of the immune checkpoint inhibitor anti-PD-L1 with radiation therapy.

Specifically, as shown in FIGS. 9 and 10A-10E and Table 12 below, G4419 enhanced the efficacy of the combination of radiation and T-cell checkpoint inhibitor anti-PD-L1 (10F.9G2) in the LLC squamous cell carcinoma breast cancer model.

Syngeneic animals (C57Bl/6 mice) were subcutaneously implanted with LLC cells in the left flank to form a xenograft. On day 8, some animals began treatment with anti PD-L1 antibodies (200 µg) as indicated below. On day 11, all animals were treated with GC4419 (24 mg/kg), 15 Gy of 250 kVp X-rays, and/or anti-PD-L1 antibodies (200 µg), as described in Table 12 below. Tumor growth was tracked as a function of time.

TABLE 12

Dosing Regimen

| Group | n | Treatment (s) | Dose | Schedule |
|---|---|---|---|---|
| 1 | 5 | Control | 0 | D11, 12, 13, 14, 15 |
| 2 | 5 | RT | 15 Gy | D11 × 1 |
| 3 | 5 | GC4419 | 10 mg/kg | D11, 12, 13, 14, 15 |
|   |   | RT | 15 Gy | D11 × 1 |
| 4 | 5 | GC4419 | 10 mg/kg | D11, 12, 13, 14, 15 |
|   |   | Anti-PD-L1 (10F.9G2) | 200 µg | D8, 11, 14 |
| 5 | 9 | Anti-PD-L1 (10F.9G2) | 200 µg | D8, 11, 14 |
|   |   | RT | 15 Gy | D11 × 1 |
| 6 | 9 | GC4419 | 10 mg/kg | D11, 12, 13, 14, 15 |
|   |   | Anti-PD-L1 (10F.9G2) | 200 µg | D8, 11, 14 |
|   |   | RT | 15 Gy | D11 × 1 |

Through Day 31 post-implantation, the triple combination of GC4419 with anti PD-L1 therapy and radiation therapy, delayed tumor growth at least as well as the dual combination of anti PD-L1 therapy and radiation therapy (FIGS. 9 and 10A-10E). It also appeared to increase the number of animals whose tumors were "cured" (disappeared) as described in FIGS. 10A-10E and Table 13 below.

TABLE 13

| % Animals Cured at Day 51 | | | |
|---|---|---|---|
| Group | n | Treatment (s) | Cures, n | % Cures |
| 1 | 5 | Control | 0 | 0 |
| 2 | 5 | RT | 0 | 0 |
| 3 | 5 | GC4419 + RT | 0 | 0 |
| 4 | 5 | GC4419 + Anti-PD-L1 | 0 | 0 |
| 5 | 9 | Anti-PD-L1 + RT | 5 | 56% |
| 6 | 9 | GC4419 + RT + Anti-PD-L1 | 7 | 78% |

What is claimed is:

1. A method of treating a cancer in a mammalian subject afflicted with the cancer, the method comprising:
    administering to the subject an immune checkpoint inhibitor, wherein the checkpoint inhibitor is at least one of an anti-CTLA4 antibody, an anti-PD-1 antibody and an anti-PDL-1 antibody; and
    administering to the subject a pentaaza macrocyclic ring complex corresponding to the formula (II) below, prior to, concomitantly with, or after administration of the immune checkpoint inhibitor, to increase the response of the cancer to the immune checkpoint inhibitor:

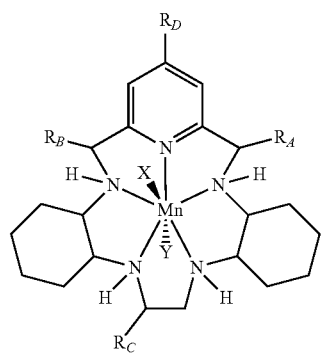

(II)

wherein
X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting
of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl, and wherein
substituted hydrocarbyl means a hydrocarbyl group that is substituted with one, two or three substitutents independently selected from alkyl, alkoxy, alkoxyalkyl, halo, hydroxy, hydroxyalkyl, or organosulfur.

2. The method according to claim 1, wherein the pentaaza macrocyclic ring complex is represented by formula (III) or formula (IV):

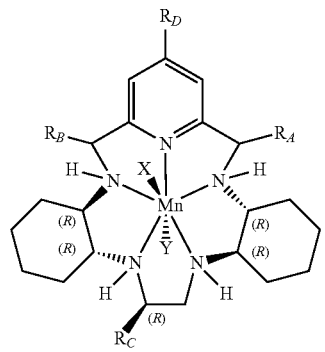

(III)

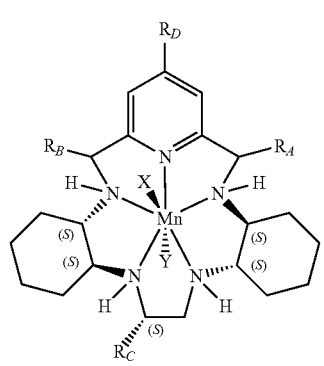

(IV)

wherein
X and Y represent suitable ligands which are derived from any monodentate or polydentate coordinating ligand or ligand system or the corresponding anion thereof; and
$R_A$, $R_B$, $R_C$, and $R_D$ are independently hydrogen, hydrocarbyl, substituted hydrocarbyl, heterocyclyl, an amino acid side chain moiety, or a moiety selected from the group consisting
of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl.

3. The method according to claim 1, wherein the pentaaza macrocyclic ring complex is a compound represented by a formula selected from the group consisting of formulae (V)-(XVI):

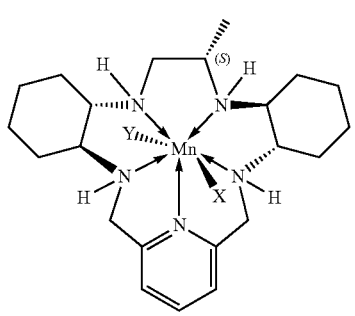

(V)

(VI)
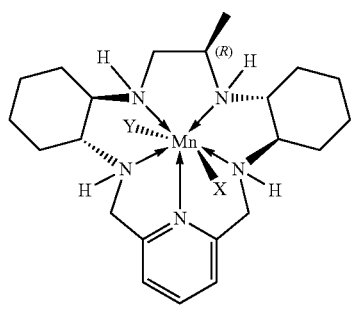
(VII)
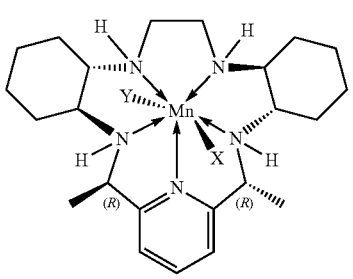
(VIII)
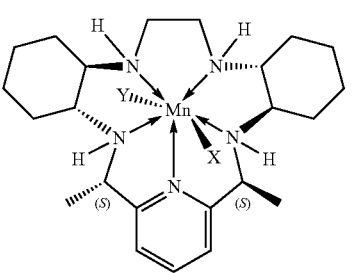
(IX)
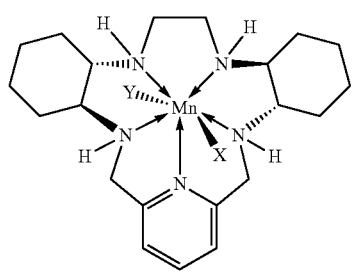
(X)
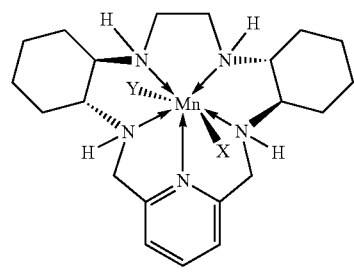
(XI)
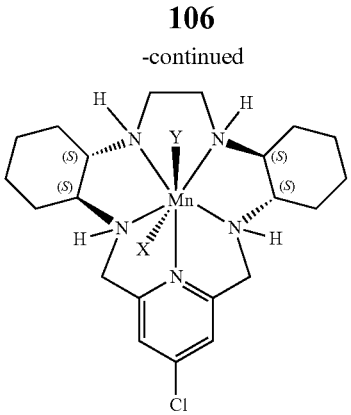
(XII)
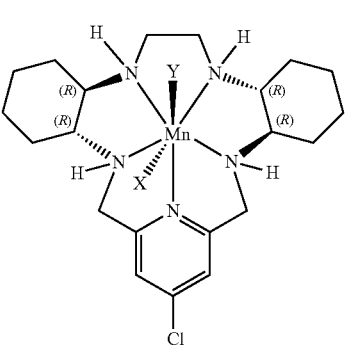
(XIII)
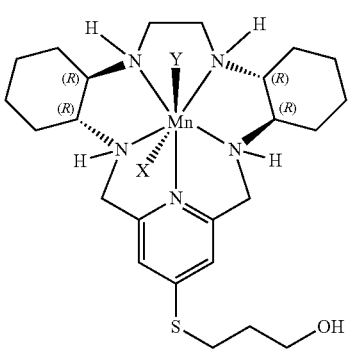
(XIV)
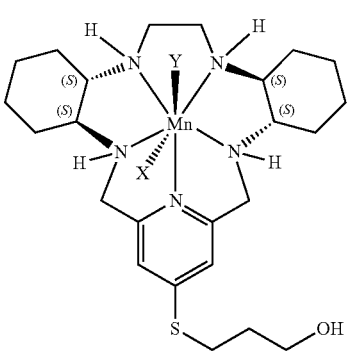
(XV)
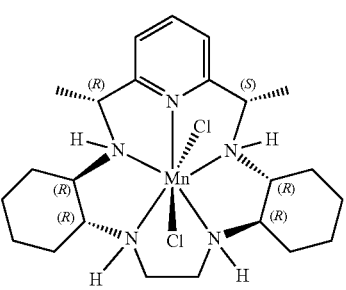

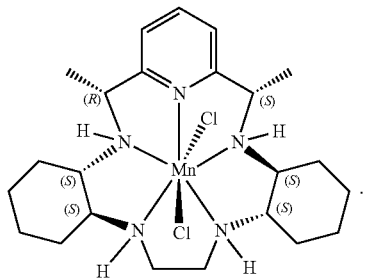

(XVI)

4. The method according to claim 1, wherein X and Y are independently selected from the group consisting of fluoro, chloro, bromo, and iodo anions.

5. The method according to claim 1, wherein X and Y are independently selected from the group consisting of alkyl carboxylates, aryl carboxylates and arylalkyl carboxylates.

6. The method according to claim 1, wherein X and Y are independently amino acids.

7. The method according to claim 1, wherein the pentaaza macrocyclic ring complex is a compound represented by a formula selected from the following group:

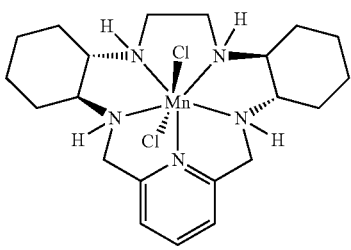

(4419)

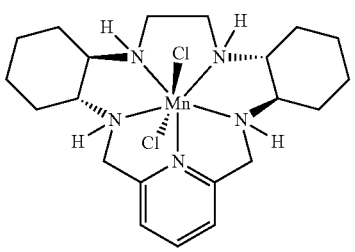

(4403)

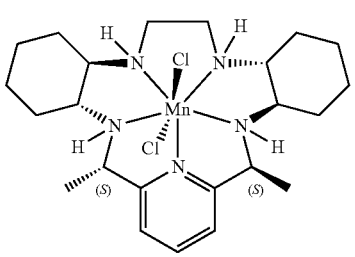

(4401)

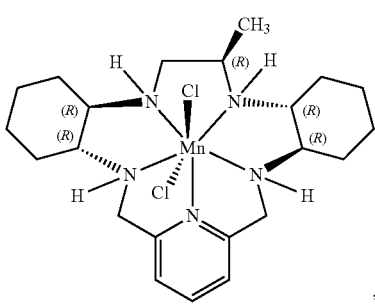

GC4444

GC4702

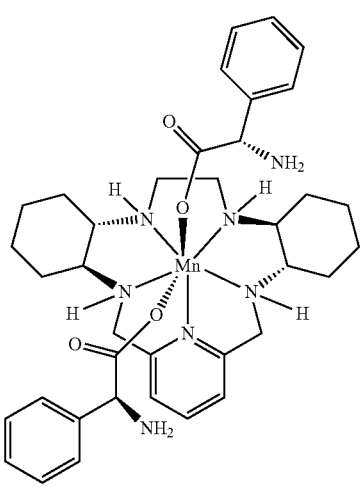

, and

[Bis-(L)-Phenylglycinato(GC4419)]
$C_{31}H_{31}MnN_2O_4$
MW 712.80

GC4711

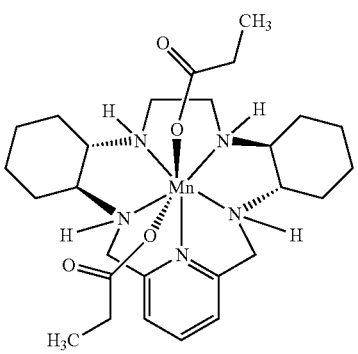

[Bis-Propionato(GC4419)]
$C_{27}H_{48}MnN_5O_4$
MW 558.63

8. The method according to claim 1, wherein:
  i) initial administration of the pentaaza macrocyclic ring complex in the course of therapy is no less than 3 days after initial administration of the immune checkpoint inhibitor; and/or
  ii) initial administration of the pentaaza macrocyclic ring complex in the course of therapy follows two doses of the immune checkpoint inhibitor; and/or
  iii) a further checkpoint inhibitor is administered that comprises one or more of a small molecular inhibitor, an antibody, an antigen binding fragment, and an Ig fusion protein.

9. The method according to claim 1:
i) comprising administering a further checkpoint inhibitor selected from the group consisting of areluman, IMP321, INCB024360, NLG-919, indoximod, galiximab, varlilumab, mogamulizumab, CP-870,893, MEDI-6469, IPH2101, urelumab, lirilumab, MGA271, anti-OX40, and BY55; and/or
ii) comprising administering a checkpoint inhibitor selected from the group consisting of ipilimumab, tremelimumab, nivolumab, pembrolizumab, pidilizumab, AMP-224, MDX-1106, AUNP 12, BMS-986016, MK-3475, CT-011, AMP224, BGB-A317, atezolizumab, MPDL3280A, MDX-1105, MEDI-4736, avelumab, BMS-936559, MSB0010718C; and/or
iii) further comprising administering one or more of an adoptive T-cell transfer and cancer vaccine to the subject, either prior to, concomitantly with, or after administration of one or more of the immune checkpoint inhibitor and pentaaza macrocyclic ring complex.

10. The method according to claim 1, wherein the cancer is selected from the group consisting of breast cancer, non-small-cell lung cancer, melanoma, renal cell carcinoma, urothelial carcinoma, bladder cancer, pancreatic cancer, head and neck cancers, colorectal cancer, prostate cancer, brain cancer, spindle cell carcinoma, and oral squamous cell carcinoma.

11. The method according to claim 1, wherein the pentaaza macrocyclic ring complex is administered:
i) to the subject in a dose in a range of from 0.2 mg/kg to 40 mg/kg; and/or
ii) parenterally, orally, intraperitoneally, subcutaneously, or intravenously.

12. The method according to claim 1, wherein the immune checkpoint inhibitor is an anti-PD-1 antibody.

13. The method according to claim 1, wherein the immune checkpoint inhibitor is an anti-CTLA4 antibody.

14. The method according to claim 1, wherein the immune checkpoint inhibitor is an anti-PDL-1 antibody.

* * * * *